United States Patent
Taylor et al.

(10) Patent No.: US 11,890,281 B2
(45) Date of Patent: Feb. 6, 2024

(54) SHP2 PHOSPHATASE INHIBITORS AND METHODS OF MAKING AND USING THE SAME

(71) Applicant: Relay Therapeutics, Inc., Cambridge, MA (US)

(72) Inventors: Alexander M. Taylor, Cambridge, MA (US); André Lescarbeau, Somerville, MA (US); Jing Wang, Shanghai (CN); Yanyan Zhang, Shanghai (CN); Gaodeng Lian, Shanghai (CN)

(73) Assignee: Relay Therapeutics, Inc., Cambridge, MA (US)

( * ) Notice: Subject to any disclaimer, the term of this patent is extended or adjusted under 35 U.S.C. 154(b) by 70 days.

(21) Appl. No.: 17/029,376

(22) Filed: Sep. 23, 2020

(65) Prior Publication Data
US 2021/0085677 A1     Mar. 25, 2021

Related U.S. Application Data

(60) Provisional application No. 62/904,986, filed on Sep. 24, 2019.

(51) Int. Cl.
| | |
|---|---|
| A61K 31/4985 | (2006.01) |
| A61K 45/06 | (2006.01) |
| C07D 519/00 | (2006.01) |
| C07D 401/14 | (2006.01) |
| C07D 221/20 | (2006.01) |
| C07D 491/107 | (2006.01) |

(52) U.S. Cl.
CPC .......... *A61K 31/4985* (2013.01); *A61K 45/06* (2013.01); *C07D 401/14* (2013.01); *C07D 519/00* (2013.01); *C07B 2200/13* (2013.01); *C07D 221/20* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 5,466,823 A | 11/1995 | Talley et al. | |
| 10,280,171 B2 | 5/2019 | Jones et al. | |
| 10,934,302 B1 | 3/2021 | Taylor et al. | |
| 10,988,466 B2 | 4/2021 | Ma et al. | |
| 11,529,347 B2 | 12/2022 | Albrecht et al. | |
| 11,591,336 B2 | 2/2023 | Taylor et al. | |
| 11,629,145 B2 | 4/2023 | Giordanetto et al. | |
| 11,701,354 B2 | 7/2023 | Taylor et al. | |
| 2011/0130396 A1 | 6/2011 | Hoelzemann et al. | |
| 2017/0001975 A1 | 1/2017 | Chen et al. | |
| 2017/0015680 A1 | 1/2017 | Chen et al. | |
| 2017/0204080 A1 | 7/2017 | Chen et al. | |
| 2017/0342078 A1 | 11/2017 | Jones et al. | |
| 2018/0186770 A1 | 7/2018 | Chen et al. | |
| 2018/0251471 A1 | 9/2018 | Chen et al. | |
| 2019/0077792 A1 | 3/2019 | Volkmann et al. | |
| 2019/0127378 A1 | 5/2019 | Ma et al. | |
| 2019/0185475 A1 | 6/2019 | Bagdanoff et al. | |
| 2019/0210977 A1 | 7/2019 | Jogalekar et al. | |
| 2019/0270746 A1 | 9/2019 | Jones et al. | |
| 2019/0290649 A1 | 9/2019 | Xie et al. | |
| 2019/0307745 A1 | 10/2019 | Albrecht et al. | |
| 2019/0389867 A1 | 12/2019 | Jones et al. | |
| 2020/0002330 A1 | 1/2020 | Chen et al. | |
| 2020/0017511 A1 | 1/2020 | Blank et al. | |
| 2020/0017517 A1 | 1/2020 | Gill et al. | |
| 2020/0048249 A1 | 2/2020 | Jones et al. | |
| 2020/0062760 A1 | 2/2020 | Giordanetto et al. | |
| 2020/0108071 A1 | 4/2020 | Chin et al. | |
| 2020/0115389 A1 | 4/2020 | Fu et al. | |
| 2020/0172546 A1 | 6/2020 | Taylor et al. | |
| 2020/0253969 A1 | 8/2020 | Taylor et al. | |
| 2020/0392128 A1 | 12/2020 | Ma et al. | |
| 2020/0392161 A1 | 12/2020 | Walters et al. | |
| 2021/0069188 A1 | 3/2021 | Taylor et al. | |
| 2021/0393623 A1 | 12/2021 | Han et al. | |
| 2022/0340576 A1 | 10/2022 | Taylor et al. | |
| 2023/0234958 A1 | 7/2023 | Taylor et al. | |

FOREIGN PATENT DOCUMENTS

| | | |
|---|---|---|
| CN | 103570622 A | 2/2014 |
| CN | 107286150 A | 10/2017 |
| CN | 110143949 A | 8/2019 |
| CN | 111153899 | 5/2020 |
| MX | 2019011330 A | 2/2020 |
| RU | 2379303 C2 | 10/2010 |
| TW | 201840553 A | 11/2018 |
| TW | 201925186 A | 7/2019 |
| WO | WO 2004/096139 | 11/2004 |
| WO | WO 2004/111060 A1 | 12/2004 |
| WO | WO 2010/011666 A2 | 1/2010 |

(Continued)

OTHER PUBLICATIONS

Morissette et al, Advanced Drug Delivery Reviews, vol. 56, pp. 275-300 (Year: 2004).*
Hackam, et al., "Translation of Research Evidence from Animals to Humans," JAMA, 296(14):1731-1732, (2006).
Jordan, V.C., "Tamoxifen: A Most Unlikely Pioneering Medicine," Nature Reviews: Drug Discovery, 2:205-213, (2003).
U.S. Appl. No. 16/651,733, Non-Final Office Action dated Jul. 23, 2021.
Bollu et al., "Molecular Pathways: Targeting Protein Tyrosine Phosphatases in Cancer," Clin Cancer Res. 23(9): 2136-2142, (May 1, 2017).

(Continued)

*Primary Examiner* — Zinna Northington Davis
(74) *Attorney, Agent, or Firm* — Alston & Bird LLP

(57) ABSTRACT

The disclosure is in part directed to crystalline forms of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine, its salt, and variants thereof.

27 Claims, 41 Drawing Sheets

(56) References Cited

FOREIGN PATENT DOCUMENTS

| WO | WO 2010/097798 A1 | 9/2010 |
|---|---|---|
| WO | WO 2010/121212 A2 | 10/2010 |
| WO | WO 2011/130396 A1 | 10/2011 |
| WO | WO 2017/156397 A1 | 9/2014 |
| WO | WO 2015/107493 A1 | 7/2015 |
| WO | WO 2015/107494 A1 | 7/2015 |
| WO | WO 2015/107495 A1 | 7/2015 |
| WO | WO 2016/203404 A1 | 12/2016 |
| WO | WO 2016/203406 A1 | 12/2016 |
| WO | WO 2017/210134 A1 | 12/2017 |
| WO | WO 2017/211303 A1 | 12/2017 |
| WO | WO 2018/013597 A1 | 1/2018 |
| WO | WO 2018/057884 A1 | 3/2018 |
| WO | WO 2018/081091 A1 | 5/2018 |
| WO | WO 2018/172984 A1 | 9/2018 |
| WO | WO 2018/218133 A1 | 11/2018 |
| WO | WO 2019/051084 A1 | 3/2019 |
| WO | WO 2019/067843 A1 | 4/2019 |
| WO | WO 2019/075265 A1 | 4/2019 |
| WO | WO 2019/118909 A1 | 6/2019 |
| WO | WO 2019/158019 A1 | 8/2019 |
| WO | WO 2019/165073 A1 | 8/2019 |
| WO | WO 2019/167000 A1 | 9/2019 |
| WO | WO 2019/183364 A1 | 9/2019 |
| WO | WO 2019/183367 A1 | 9/2019 |
| WO | WO 2019/199792 A1 | 10/2019 |
| WO | WO 2019/233810 A1 | 12/2019 |
| WO | WO 2020/022323 A1 | 1/2020 |
| WO | WO 2020/063760 A1 | 4/2020 |
| WO | WO 2020/065452 A1 | 4/2020 |
| WO | WO 2020/065453 A1 | 4/2020 |
| WO | WO 2020/073945 A1 | 4/2020 |
| WO | WO 2020/073949 A1 | 4/2020 |
| WO | WO 2020/076723 A1 | 4/2020 |
| WO | WO 2020/081848 A1 | 4/2020 |
| WO | WO 2020/094018 A1 | 5/2020 |
| WO | WO 2020/094104 A1 | 5/2020 |

OTHER PUBLICATIONS

Copin et al. "Snar Versus Buchwald-Hartwig Amination/Amidation in the Imidazo[2,1-b] [1,3,4]thiadiazole Series," European Journal of Organic Chemistry, vol. 2015, No. 31, pp. 6932-6942, (Sep. 29, 2015).

Fortanet et al. "Allosteric Inhibition of SHP2: Identification of a Potent, Selective, and Orally Efficacious Phosphatase Inhibitor," J. Med. Chem. 2016, 59, 17, pp. 7773-7782.

Hellmuth et al., Specific inhibitors of the protein tyrosine phosphatase Shp2 identified by high-throughput docking, PNAS, 105(20), 7275-7280, (2008).

Horig et al., "From bench to clinic and back: Perspective on the 1st IQPC Translational Research Conference" Journal of Translational Medicine, 2, 44, (Dec. 2004).

Krasavin et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.

Larochelle et al. "Identification of An Allosteric Benzothiazolopyrimidone Inhibitor of the Oncogenic Protein Tyrosine Phosphatase SHP2," Bioorganic & Medicinal Chemistry, vol. 25, No. 24, pp. 6479-6485, (Oct. 20, 2017).

Lazo et al., "New Approaches to Difficult Drug Targets: the Phosphatase Story," SLAS Discovery, vol. 22(9), 1071-1083, (2017).

Safarov et al. "Preparation of 5-Bromo-6-phenylimidazo(2,1-b)(1,3,4)thiadiazol-2-ylamines," Journal of Heterocyclic Chemistry, Wiley-Blackwell Publishing, Inc, Us, vol. 45, No. 1, Jan. 1, 2008, pp. 299-302.

Schafer et al., "Failure is an option: learning from unsuccessful proof-of-concept trials," Drug Discovery Today, 13, 913-916, (Nov. 2018).

Shen et al. "3-Aminopyrazolopyrazine Derivatives as Spleen Tyrosine Kinase Inhibitors," Hemical Biology & Drug Design, vol. 88, No. 5, 2016, pp. 690-698.

Temple et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11, pp. 5481-5486, ( Oct. 11, 2016).

Yokoi et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, pp. 5305-5309, (Oct. 13, 2017).

U.S. Appl. No. 16/335,933, Non-Final Office Action dated Jan. 8, 2020.

U.S. Appl. No. 16/355,061, Non-Final Office Action dated Feb. 19, 2021.

U.S. Appl. No. 16/355,061, Requirement for Restriction/Election dated Jul. 31, 2020.

U.S. Appl. No. 16/616,361, Non-Final Office Action dated May 13, 2021.

U.S. Appl. No. 16/616,361, Requirement for Restriction/Election dated Oct. 30, 2020.

U.S. Appl. No. 16/886,105, Notice of Allowance dated Sep. 9, 2020.

U.S. Appl. No. 16/886,105, Notice of Allowance dated Nov. 4, 2020.

U.S. Appl. No. 16/335,933, Final Office Action dated Aug. 26, 2020.

WIPO Application No. PCT/US2017/052950, PCT International Preliminary Report on Patentability dated Mar. 26, 2019.

WIPO Application No. PCT/US2017/052950, PCT International Search Report and Written Opinion of the International Searching Authority dated Mar. 29, 2018.

WIPO Application No. PCT/US2017/058048, PCT International Preliminary Report on Patentability dated Apr. 30, 2019.

WIPO Application No. PCT/US2017/058048, PCT International Search Report and Written Opinion of the International Searching Authority dated May 3, 2018.

WIPO Application No. PCT/US2018/034614, PCT International Preliminary Report on Patentability dated Nov. 26, 2019.

WIPO Application No. PCT/US2018/034614, PCT International Search Report and Written Opinion of the International Searching Authority dated Nov. 29, 2018.

WIPO Application No. PCT/US2018/053322, PCT International Preliminary Report on Patentability dated Mar. 31, 2020.

WIPO Application No. PCT/US2018/053322, PCT International Search Report and Written Opinion of the International Searching Authority dated Apr. 4, 2019.

WIPO Application No. PCT/US2019/023389, PCT International Search Report and Written Opinion of the International Searching Authority dated May 10, 2019.

WIPO Application No. PCT/US2019/023389, PCT International Preliminary Report on Patentability dated Sep. 22, 2020.

WIPO Application No. PCT/US2020/052118, PCT International Search Report and Written Opinion of the International Searching Authority dated Dec. 14, 2020.

Aceto, N. et al., "Tyrosine phosphatase SHP2 promotes breast cancer progression and maintains tumor-initiating cells via activation of key transcription factors and a positive feedback signaling loop," Nature Medicine, 18(4):529-538, (2012).

Bastin et al., "Salt selection and optimization procedures for pharmaceutical new chemical entities," Organic process research and development, 4(5):427-435, (2000) (abstract).

Bentires-Alj, M. et al., "Activating Mutations of the Noonan Syndrome-Associated SHP2/PTPN11 Gene in Human Solid Tumors and Adult Acute Myelogenous Leukemia," Cancer Res., 64:8816-8820, (2004).

Berge, et al., "Pharmaceutical Salts," J. Pharm. Sci., 66(1):1, (1977).

Cai, P. et al., "Expression and clinical significance of tyrosine phosphatase SHP-2 in colon cancer," Biomedicine & Pharmacotherapy, 68:285-290, (2014).

Chen, Y.-N.P. et al., "Allosteric inhibition of SHP2 phosphatase inhibits cancers driven by receptor tyrosine kinases," Nature, 535:158-152, (2016).

(56) References Cited

OTHER PUBLICATIONS

Chou, "Drug Combination studies and their synergy quantification using the Chou-Talalay method," Cancer Research, 70(2):440-446, (2010).
Furcht, C.M. et al., "Diminished functional role and altered localization of SHP2 in non-small cell lung cancer cells with EGFR-activating mutations," Oncogene, 32:2346-2355, (2013).
Gould, P.L., "Salt selection for basic drugs," Int J. Pharmaceutics, 33:201-217, (1986).
Grossman, K.S. et al., "The tyrosine phosphatase Shp2 in development and cancer," Adv. Cancer Res., 106:53-89, (2010).
Kümmerer, "Pharmaceuticals in the environment," Annual Review of Environment and Resources, 35:57-75, (2010).
Schneeberger, V.E. et al., "Inhibition of Shp2 suppresses mutant EGFR-induced lung tumors in transgenic mouse model of lung adenocarcinoma," Oncotarget, 6:6191-6202, (2015).
Wang, J. et al., "Inhibition of SHP2 ameliorates the pathogenesis of systemic lupus erythematosus," The Journal of Clinical Invest. 126:2077-2092, (2016).
RU Application No. 2020134302, Official Action and Search Report dated Sep. 9, 2022.
U.S. Appl. No. 16/335,933, Non-Final Office Action dated Sep. 16, 2021.
U.S. Appl. No. 16/335,933, Notice of Allowance dated Apr. 15, 2022.
U.S. Appl. No. 16/335,933, Notice of Allowance dated Aug. 25, 2022.
U.S. Appl. No. 16/335,933, Supplemental Notice of Allowability dated Sep. 14, 2022.
U.S. Appl. No. 16/344,061, Final Office Action dated Aug. 25, 2021.
U.S. Appl. No. 16/344,061, Non-Final Office Action dated Mar. 31, 2022.
U.S. Appl. No. 16/344,061, Notice of Allowance dated Nov. 16, 2022.
U.S. Appl. No. 16/616,361, Final Office Action dated Sep. 30, 2021.
U.S. Appl. No. 16/616,361, Notice of Allowance dated Apr. 26, 2022.
U.S. Appl. No. 16/616,361, Notice of Allowance dated Oct. 18, 2022.
U.S. Appl. No. 16/950,576, Non-Final Office Action dated Dec. 20, 2022.
Dardaei et al., "SHP2 inhibition restores sensitivity in ALK-rearranged non-small-cell lung cancer resistant to ALK inhibitors," Nat Med. 24(4):512-517, (2018).
Fedele et al., "SHP2 Inhibition Abrogates MEK inhibitor Resistance in Multiple Cancer Models," BioRxiv, 307876, (2018).
Hill et al., "PTPN11 Plays Oncogenic Roles and Is a Therapeutic Target for BRAF Wild-Type Melanomas," Mol. Cancer Res., 17:583-593, (2019).
Hu et al., "Overexpression of SHP2 tyrosine phosphatase promotes the tumorigenesis of breast carcinoma," Oncol Rep., 32(1):205-212, (2014).
Nichols et al., "RAS nucleotide cycling underlies the SHP2 phosphatase dependence of mutant BRAF-, NF1- and RAS-driven cancers," Nat. Cell Biol, 20:1064-1073, (2018).
Prahallad et al., "PTPN11 Is a Central Node in Intrinsic and Acquired Resistance to Targeted Cancer Drugs," Cell Rep, 12:1978-1985, (2015).
Qi et al., "Shp2 Inhibits Proliferation of Esophageal Squamous Cell Cancer via Dephosphorylation of Stat3," Int. J. Mol. Sci., 18:134, (2017).
Sausgruber et al., "Tyrosine phosphatase SHP2 increases cell motility in triple-negative breast cancer through the activation of SRC-family kinases," Oncogene, 34:2272-2278, (2015).
Sun et al., Synergistic effects of SHP2 and PI3K pathway inhibitors in GAB2-overexpressing ovarian cancer,: Am J Cancer Res, 9(1):145-159, (2019).
Wong et al., "SHP-2 phosphatase contributes to KRAS-driven intestinal oncogenesis but prevents colitis-associated cancer development," Oncotarget, 7(40):65676-65695, (Oct. 4, 2016).
Yu et al., "Targeting Protein Tyrosine Phosphatase SHP2 for the Treatment of PTPN11-Associated Malignancies," Mol. Cancer Ther., 12:1738-1748, (2013).
Zhao et al., "Conditional knockout of SHP2 in ErbB2 transgenic mice or inhibition in HER2-amplified breast cancer cell lines blocks oncogene expression and tumorigenesis," Oncogene, 38:2275-2290, (2019).
CN Application No. 201980034042.8, Office Action and Search Report dated Jan. 19, 2023.
MX Application No. MX/a/2020/009782, Office Action dated dated Apr. 24, 2023.
ROC (Taiwan) Application No. 108109755, Office Action and Search Report dated Jan. 4, 2023.

* cited by examiner

SHP2 PHOSPHATASE INHIBITORS AND METHODS OF MAKING AND USING THE SAME

CROSS REFERENCE TO RELATED APPLICATIONS

This application claims the benefit of, and priority to, U.S. Provisional application Ser. No. 62/904,986, filed Sep. 24, 2019; the contents of which are hereby incorporated by reference herein in its entirety.

BACKGROUND

Src homology region 2 (SH2)-containing protein tyrosine phosphatase 2 (SHP2) is a protein tyrosine phosphatase encoded by the PTPN11 gene. SHP2 contains two Src homology 2 (SH2) $NH_2$-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g., K. S. Grossman et al., *Adv. Cancer Res.* 2010, 106, 53-89; and references cited therein.)

In the basal state, SHP2 is normally auto-inhibited due to intramolecular interactions between its N-terminal SH2 (N-SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N-SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Thus, there is a need for SHP2 phosphatase inhibitor compounds and methods for treating cancer and other disorders with these compounds.

Polymorphism is the ability of a substance to crystallize in more than one crystal lattice arrangement. Crystallization, or polymorphism, can influence many aspects of solid state properties of a drug substance. A crystalline substance may differ considerably from an amorphous form, and different crystal modifications of a substance may differ considerably from one another in many respects including solubility, dissolution rate and/or bioavailability. Generally, it is difficult to predict whether or not a given compound will form various crystalline solid state forms. It is even more difficult to predict the physical properties of these crystalline solid state forms. Further, it can be advantageous to have a crystalline form of a therapeutic agent for certain formulations, e.g., formulations suitable for subcutaneous use.

SUMMARY

This disclosure is generally directed to, among other things, (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine and salts thereof. Additionally, this disclosure is generally directed to, among other things, to the crystalline forms of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine and salts thereof.

For example, provided herein is a compound of Formula (I)

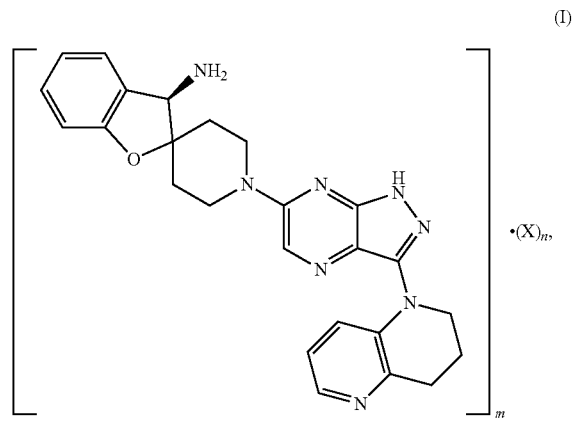

or a solvate thereof;
wherein,
m is 1-9;
n is 0-3; and
X is hydrochloric acid, hydrobromic acid, sulfuric acid, methane sulfonic acid, phosphoric acid, p-toluene sulfonic acid, benzene sulfonic acid, oxalic acid, L-aspartic acid, maleic acid, malonic acid, L-tartaric acid, fumaric acid, citric acid, succinic acid, or glutaric acid.

A pharmaceutical composition comprising a disclosed compound or crystalline form provided herein and a pharmaceutically acceptable excipient is contemplated, for example, a composition that is formulated for subcutaneous, intravenous or oral administration.

DETAILED DESCRIPTION

Figure 1A:
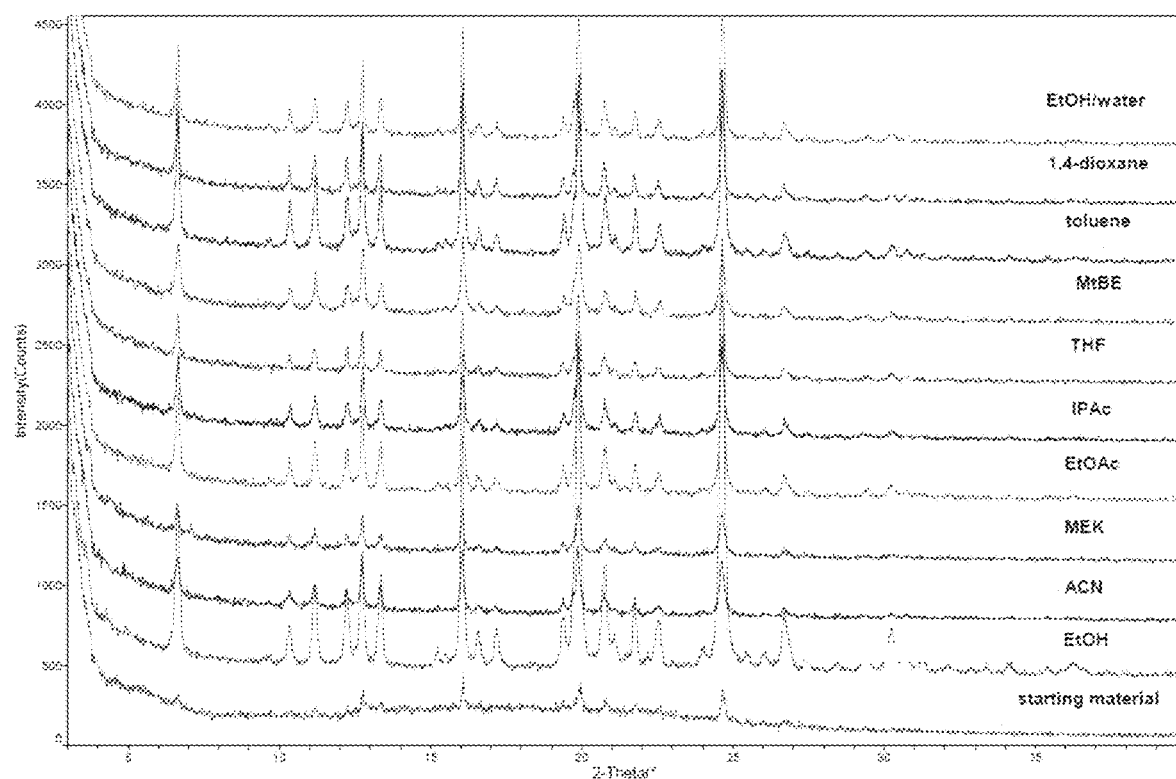
FIG. 1A depicts the X-ray diffraction pattern of Pattern A of Compound I-1 in various solvents after temperature cycle procedure.

At least in part, this disclosure is directed to (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine and salts thereof, its salts and crystalline forms thereof. The disclosure also provides for a pharmaceutical composition comprising (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine and salts thereof, its salts, and crystalline forms thereof, and a pharmaceutically acceptable carrier. The term "crystalline form" refers to a crystal form or modification that can be characterized by analytical methods such as, e.g., X-ray powder diffraction.

In one embodiment, provided herein is a compound of Formula (I)

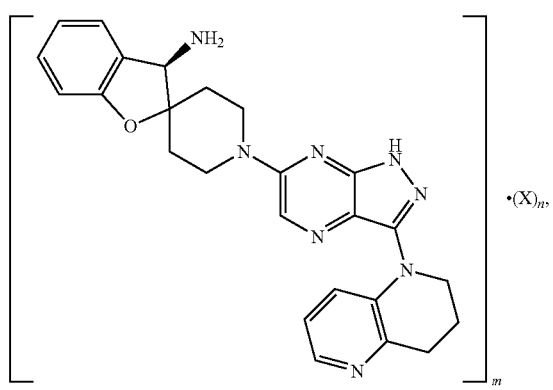

or a solvate thereof;
wherein,
m is 1-9;
n is 0-3; and
X is hydrochloric acid, hydrobromic acid, sulfuric acid, methane sulfonic acid, phosphoric acid, p-toluene sulfonic acid, benzene sulfonic acid, oxalic acid, L-aspartic acid, maleic acid, malonic acid, L-tartaric acid, fumaric acid, citric acid, succinic acid, or glutaric acid.

In some embodiments, provided herein is a compound of Formula (I)

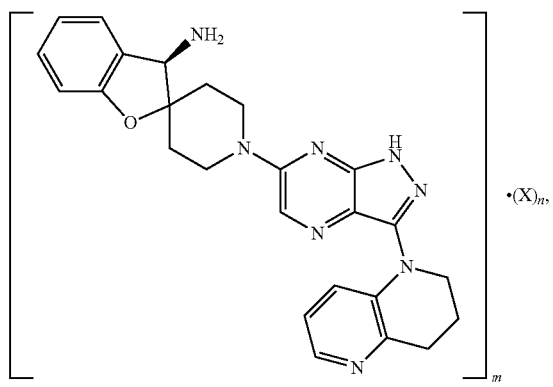

or a solvate thereof;
wherein,
m is 1-9;
n is 1-3; and
X is selected from a group consisting of hydrochloric acid, hydrobromic acid, sulfuric acid, methane sulfonic acid, phosphoric acid, p-toluene sulfonic acid, benzene sulfonic acid, oxalic acid, L-aspartic acid, maleic acid, malonic acid, L-tartaric acid, fumaric acid, citric acid, succinic acid, and glutaric acid.

It will be appreciated by one of ordinary skill in the art that the acid moiety indicated as "X" and (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine are ionically bonded to form a compound of Formula (I).

It is contemplated that a compound of Formula (I) can exist in a variety of physical forms. For example, a compound of Formula (I) can be in solution, suspension, or in solid form. In certain embodiments, a compound of Formula (I) is in solid form. When a compound of Formula (I) is in solid form, said compound may be amorphous, crystalline, or a mixture thereof. Exemplary solid forms are described in more detail below.

In some embodiments, Formula (I), may be in a hydrate form. In some embodiments, Formula (I), may be in a hemi-hydrate form.

In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9.

In some embodiments, n is 0. In some embodiments, n is 1. In some embodiments, n is 2. In some embodiments, n is 3. In some embodiments, n is 0.5. In some embodiments, n is 1.5. In some embodiments, n is 2.5.

In some embodiments, X is hydrochloric acid. In some embodiments, X is hydrobromic acid. In some embodiments, X is sulfuric acid. In some embodiments, X is methane sulfonic acid. In some embodiments, X is phosphoric acid. In some embodiments, X is p-toluene sulfonic acid. In some embodiments, X is benzene sulfonic acid. In some embodiments, X is oxalic acid. In some embodiments, X is L-aspartic acid. In some embodiments, X is maleic acid. In some embodiments, X is malonic acid. In some embodiments, X is L-tartaric acid. In some embodiments, X is fumaric acid. In some embodiments, X is citric acid. In some embodiments, X is succinic acid. In some embodiments, X is glutaric acid.

In one aspect, provided herein is (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine. In some embodiments, a compound of Formula (I) is compound I-1:

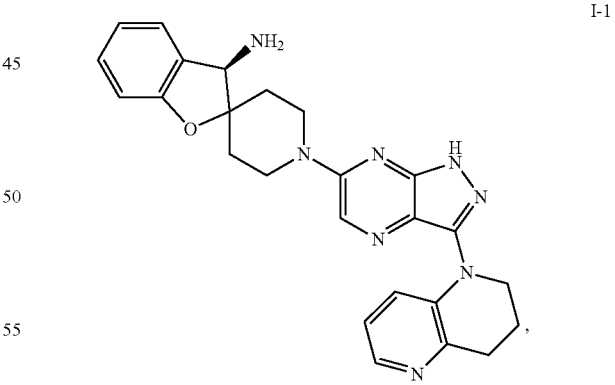

or a solvate thereof.

In some embodiments, compound I-1 is an amorphous solid. In other embodiments, compound I-1 is a crystalline solid. For example, the solid, crystalline form of compound I-1 may be characterized by a powder X-ray diffraction pattern with at least two characteristic peaks, in degrees 2θ, each selected from the group consisting of about 24.6 2θ, about 19.9 2θ and about 16.0 2θ. For example, the solid, crystalline form of compound I-1 may be characterized by a powder X-ray diffraction pattern with at least two characteristic peaks, in degrees 2θ, each selected from the group consisting of about 24.6 2θ, about 19.9 2θ, about 16.0 2θ, about 6.7 2θ, about 12.8 2θ, about 13.4 2θ and about 20.7 2θ. In some embodiments the solid, crystalline form of compound I-1 may be characterized by a powder X-ray diffraction pattern with at least three characteristic peaks, in degrees 2θ, each selected from the group consisting of about 24.6 2θ, about 19.9 2θ, about 16.0 2θ, about 6.7 2θ, about 12.8 2θ, about 13.4 2θ and about 20.7 2θ. In some embodiments the solid, crystalline form of compound I-1 may be characterized by a powder X-ray diffraction pattern with at least four characteristic peaks, in degrees 2θ, each selected from the group consisting of about 24.6 2θ, about 19.9 2θ, about 16.0 2θ, about 6.7 2θ, about 12.8 2θ, about 13.4 2θ and about 20.7 2θ. According to another aspect, compound I-1 has an X-Ray diffraction pattern substantially similar to that depicted in FIG. 1A. In some embodiments the solid, crystalline form of compound I-1 may be characterized by a powder X-ray diffraction pattern with at least two characteristic peaks, in degrees 2θ, each selected from the group consisting of the peaks listed in Table 2. In some embodiments the solid, crystalline form of compound I-1 may be characterized by a powder X-ray diffraction pattern with at least three characteristic peaks, in degrees 2θ, each selected from the group consisting of the peaks listed in Table 2. In some embodiments the solid, crystalline form of compound I-1 may be characterized by a powder X-ray diffraction pattern with at least four characteristic peaks, in degrees 2θ, each selected from the group consisting of the peaks listed in Table 2.

The term "about" in the context of peaks at degrees 2θ means that there is an uncertainty in the measurements of the 2θ of ±0.5 (expressed in 2θ) or, for example, means that that there is an uncertainty in the measurements of the 2θ of ±0.2 (expressed in 2θ).

Figure 1B:
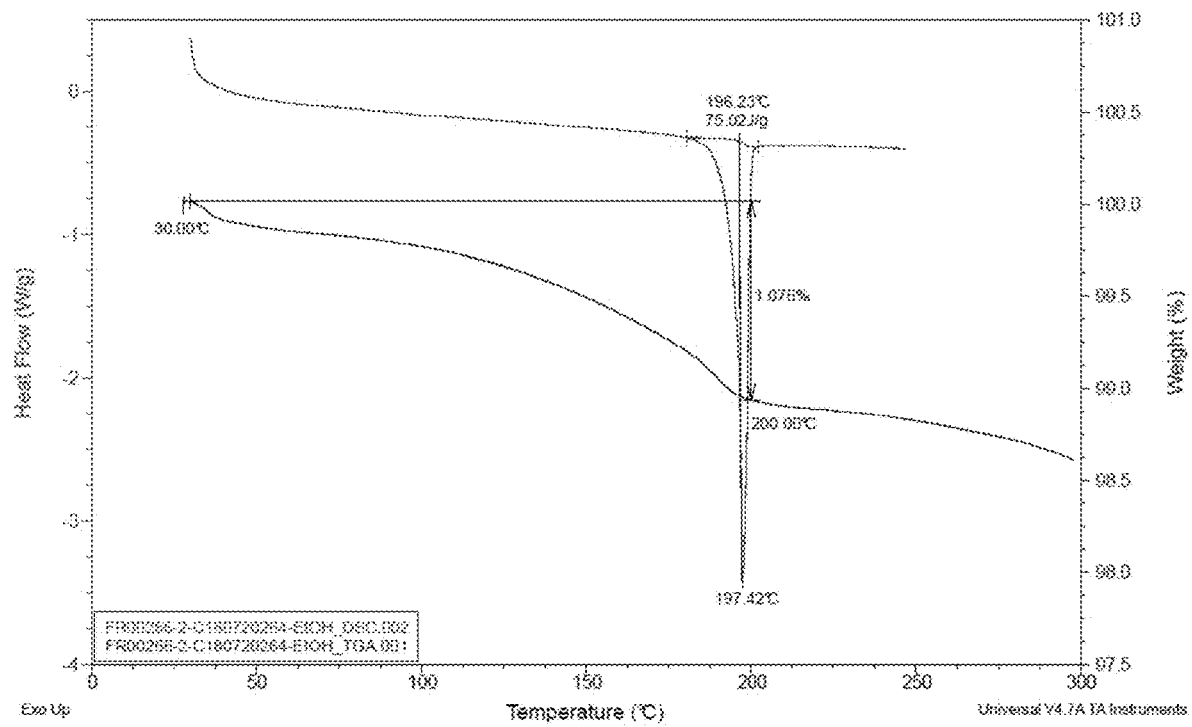
FIG. 1B depicts the characterization of Pattern A of Compound I-1 by differential scanning calorimetry (DSC) (green) and thermogravimetric analysis (TGA) (blue).

According to another aspect, compound I-1 has a thermogravimetric analysis pattern substantially similar to that depicted in FIG. 1B. According to yet another aspect, compound I-1 has a differential scanning calorimetry pattern substantially similar to that depicted in FIG. 1B. For example, the contemplated solid, crystalline form of compound I-1 may be characterized by a differential scanning calorimetry (DSC) profile showing an endotherm with an onset of about 196° C., a peak of about 197° C. Compound I-1 can be characterized by substantial similarity to two or more of these figures simultaneously.

In another embodiment, a compound of Formula (I) is compound I-2 wherein, compound I-2 is a hydrobromide salt. In some embodiments, compound I-2 is a monohydrobromide salt. In some embodiments, compound I-2 is a bis-hydrobromide salt. In some embodiments, compound I-2 is a tris-hydrobromide salt. In some embodiments compound I-2 is a crystalline solid. In some embodiments, compound I-2 is a crystalline solid and is Pattern S1-I. According to another aspect, compound I-2 has an X-Ray diffraction pattern substantially similar to that depicted in FIG. 2A. According to another aspect, compound I-2 has an X-Ray diffraction pattern substantially similar to that depicted in FIG. 2B. According to another aspect, compound I-2 has a thermogravimetric analysis pattern substantially similar to that depicted in FIG. 2C. According to yet another aspect, compound I-2 has a differential scanning calorimetry pattern substantially similar to that depicted in FIG. 2C. Compound I-2 can be characterized by substantial similarity to two or more of these figures simultaneously.

Figure 3A:
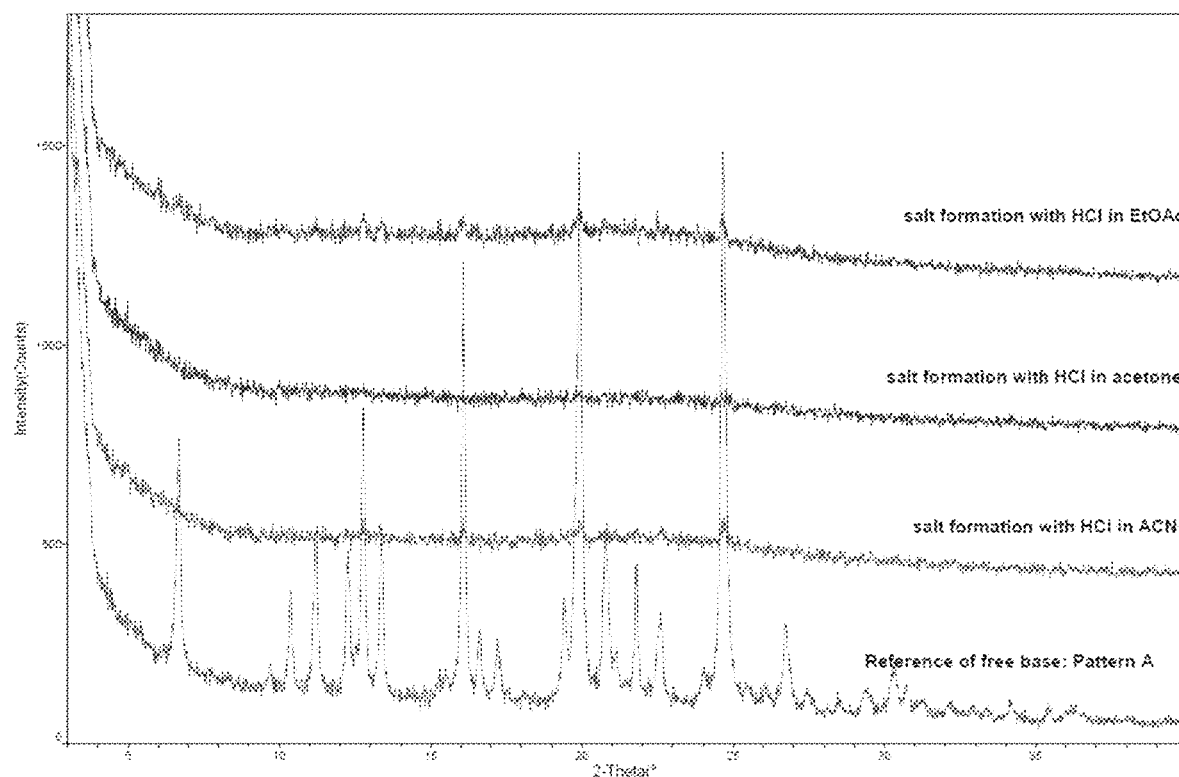
FIG. 3A depicts the characterization of X-ray diffraction pattern of Compound I-3 compared to the X-ray diffraction pattern of Pattern A of Compound I-1.
Figure 3B:
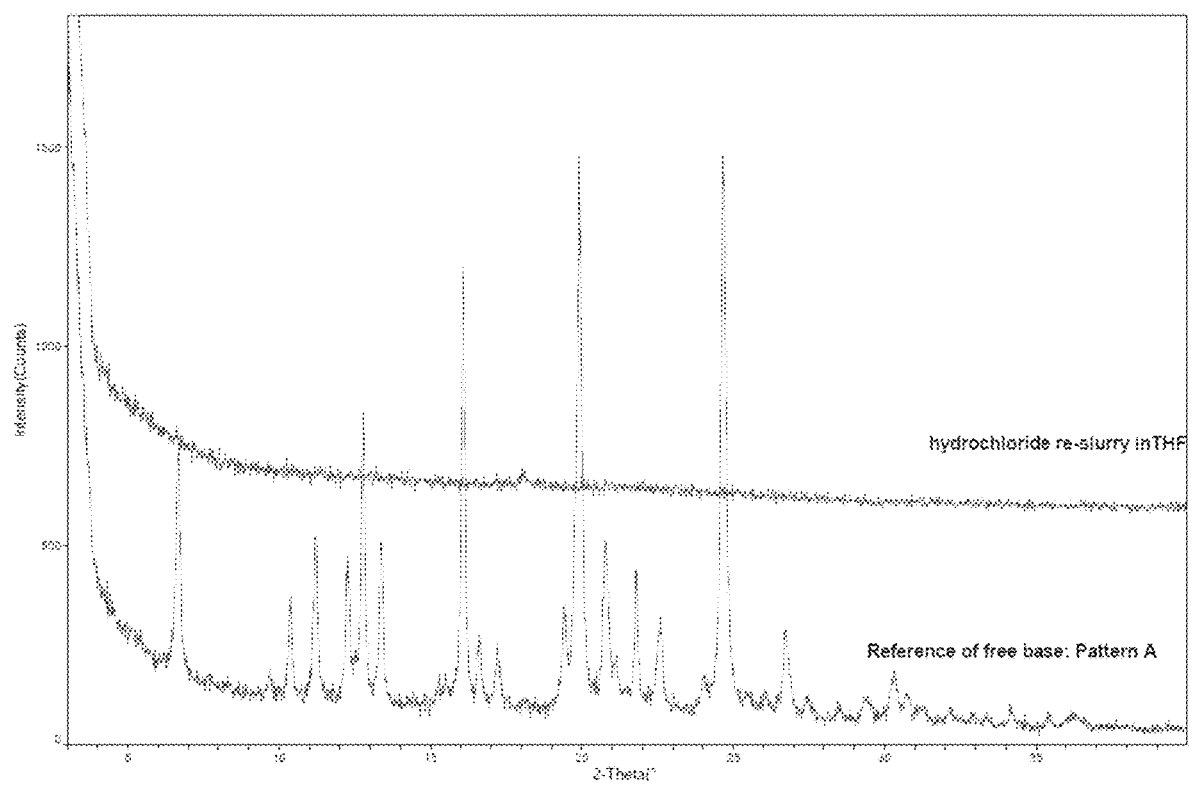
FIG. 3B depicts the characterization of X-ray diffraction pattern of Compound I-3 after re-slurry experiments compared to the X-ray diffraction pattern of Pattern A of Compound I-1.

In another embodiment, a compound of Formula (I) is compound I-3 wherein, compound I-3 is a hydrochloride salt. In some embodiments, compound I-3 is a monohydrochloride salt. In some embodiments, compound I-3 is a bis-hydrochloride salt. In some embodiments, compound I-3 is a tris-hydrochloride salt. In some embodiments compound I-3 is a solid. According to another aspect, compound I-3 has an X-Ray diffraction pattern substantially similar to that depicted in FIG. 3A. According to another aspect, compound I-3 has an X-Ray diffraction pattern substantially similar to that depicted in FIG. 3B. Compound I-3 can be characterized by substantial similarity to two of these figures simultaneously.

Figure 4A:
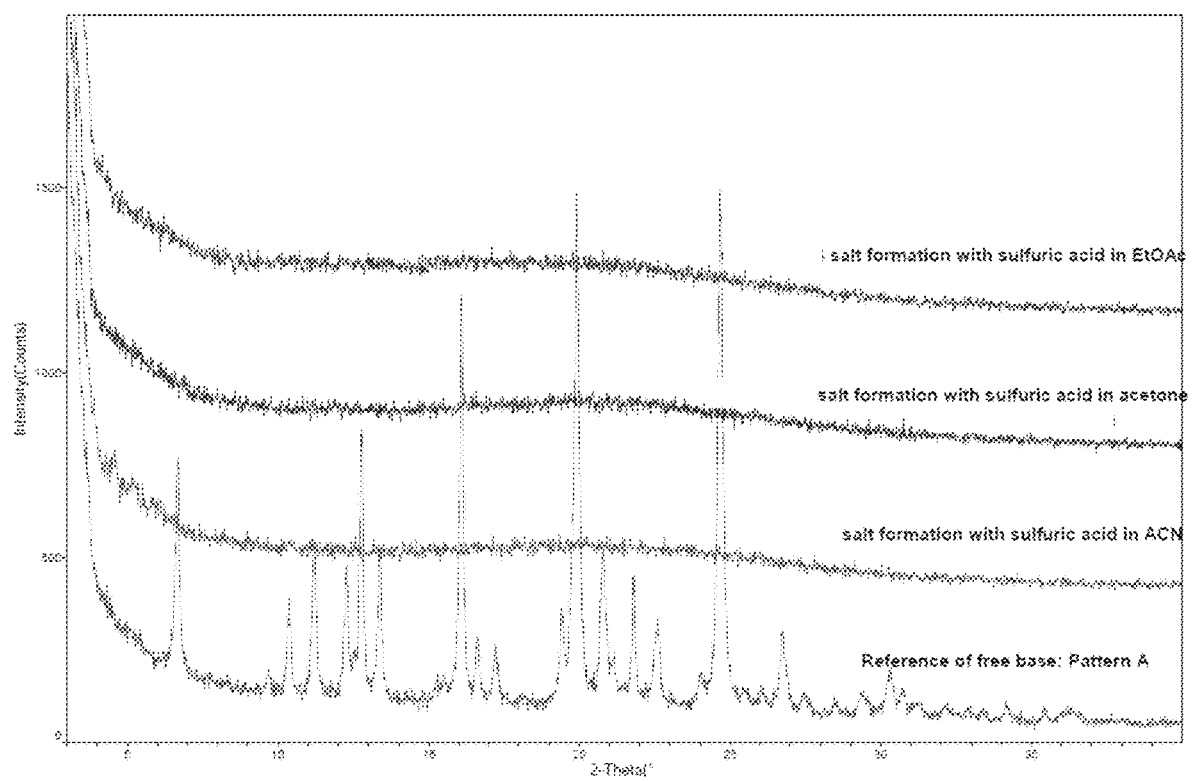
FIG. 4A depicts the characterization of X-ray diffraction pattern of Compound I-4 compared to the X-ray diffraction pattern of Pattern A of Compound I-1.
Figure 4B:
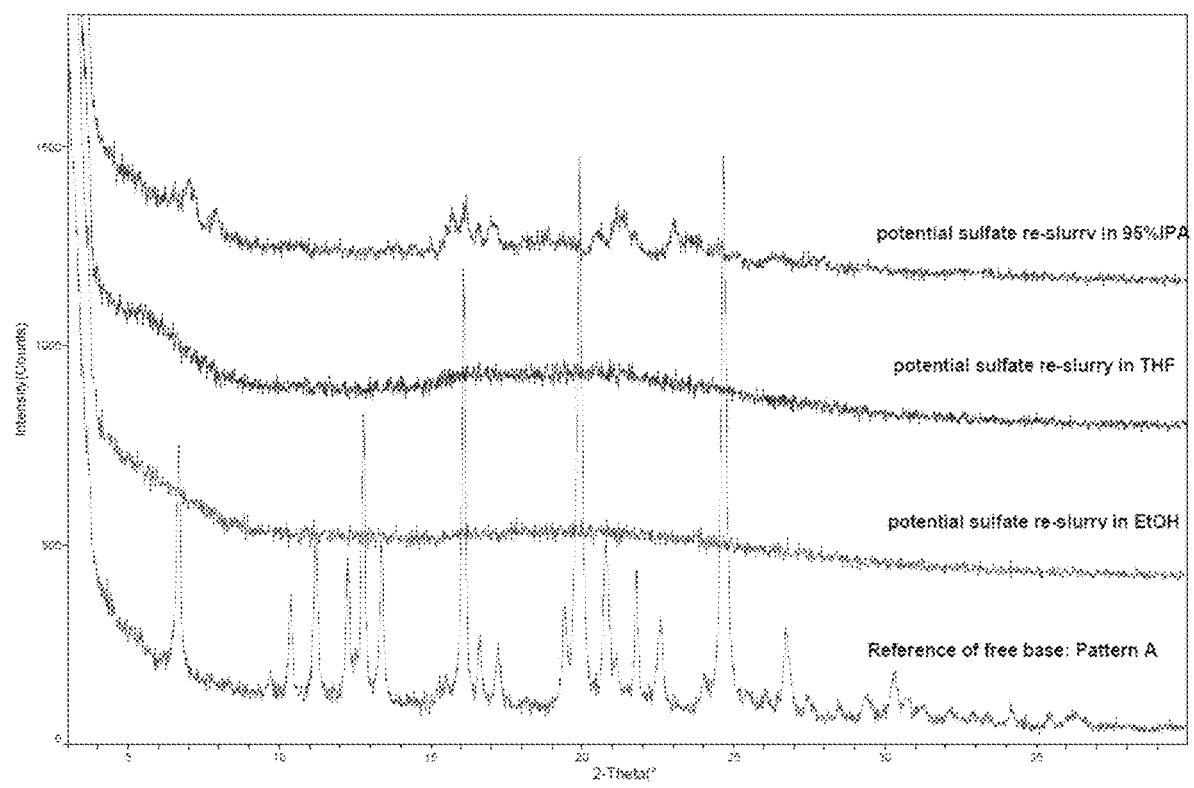
FIG. 4B depicts the characterization of X-ray diffraction pattern of Compound I-4 after re-slurry experiments compared to the X-ray diffraction pattern of Pattern A of Compound I-1.

In another embodiment, a compound of Formula (I) is compound I-4 wherein, compound I-4 is a sulfuric acid salt. In some embodiments compound I-4 is a solid. According to another aspect, compound I-4 has an X-Ray diffraction pattern substantially similar to that depicted in FIG. 4A. According to another aspect, compound I-4 has an X-Ray diffraction pattern substantially similar to that depicted in FIG. 4B. Compound I-4 can be characterized by substantial similarity to two of these figures simultaneously.

Figure 5A:
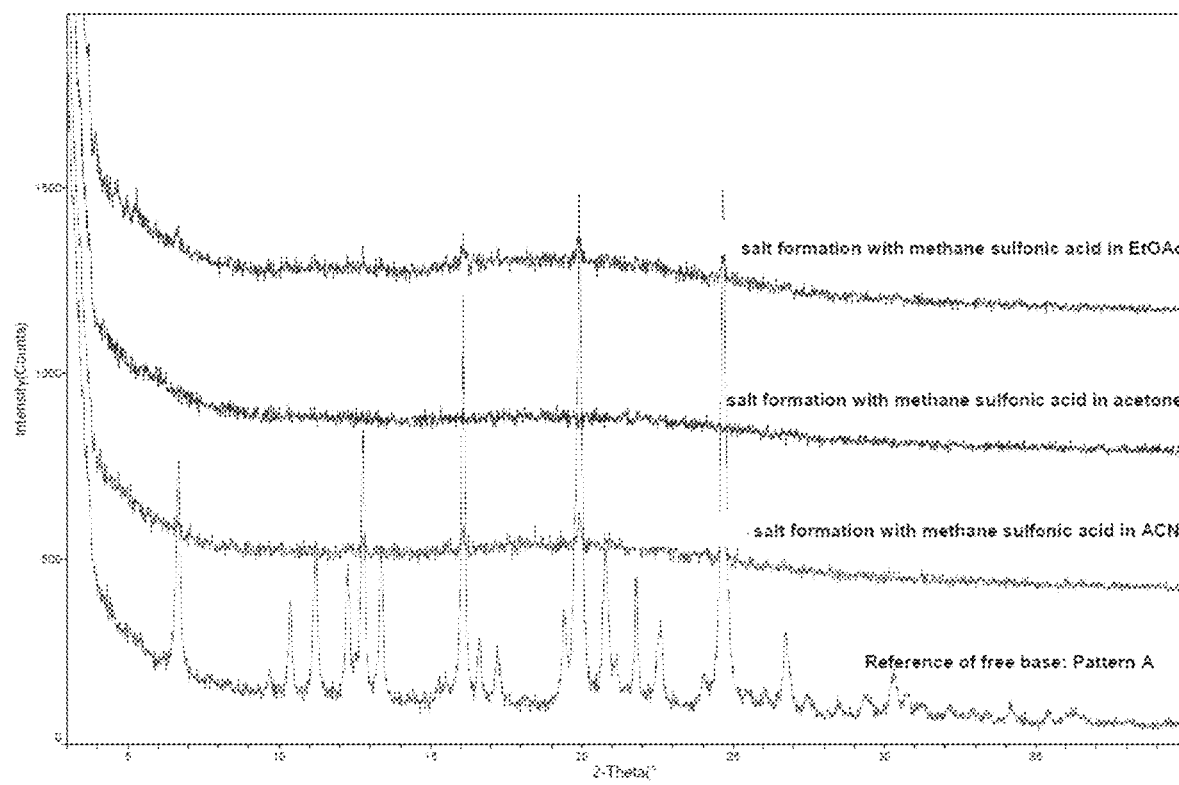
FIG. 5A depicts the characterization of X-ray diffraction pattern of Compound I-5 compared to the X-ray diffraction pattern of Pattern A of Compound I-1.
Figure 5B:
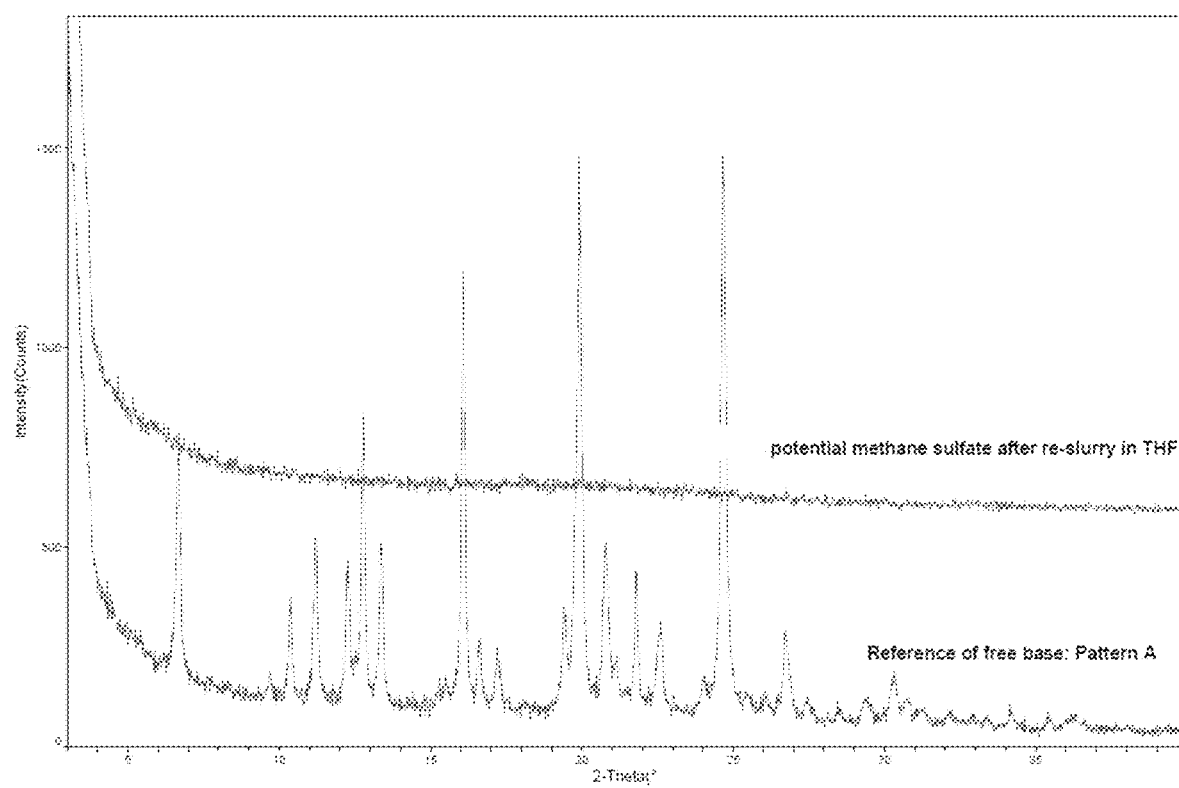
FIG. 5B depicts the characterization of X-ray diffraction pattern of Compound I-5 after re-slurry experiments compared to the X-ray diffraction pattern of Pattern A of Compound I-1.

In another embodiment, a compound of Formula (I) is compound I-5 wherein, compound I-5 is a methane sulfonic acid salt. In some embodiments compound I-5 is a solid. According to another aspect, compound I-5 has an X-Ray diffraction pattern substantially similar to that depicted in FIG. 5A. According to another aspect, compound I-5 has an X-Ray diffraction pattern substantially similar to that depicted in FIG. 5B. Compound I-5 can be characterized by substantial similarity to two of these figures simultaneously.

Figure 6A:
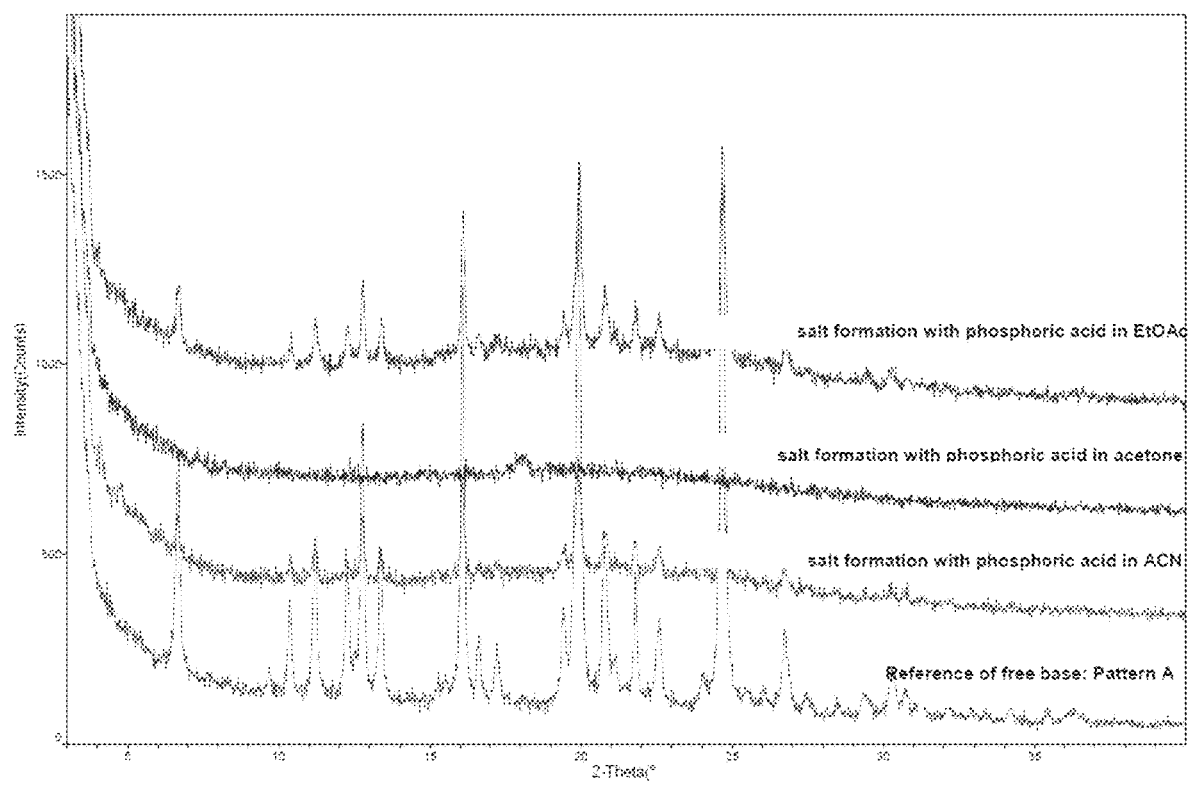
FIG. 6A depicts the characterization of X-ray diffraction pattern of Compound I-6 compared to the X-ray diffraction pattern of Pattern A of Compound I-1.
Figure 6B:
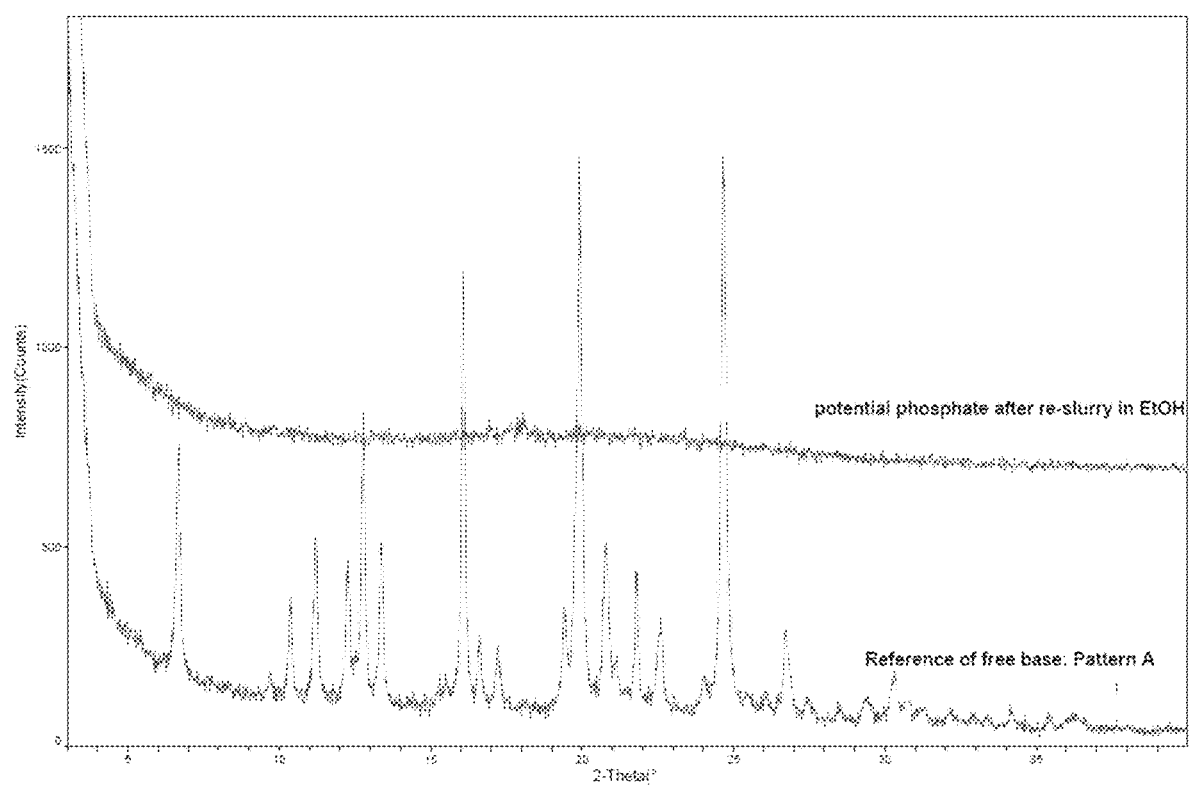
FIG. 6B depicts the characterization of X-ray diffraction pattern of Compound I-6 after re-slurry experiments compared to the X-ray diffraction pattern of Pattern A of Compound I-1.

In another embodiment, a compound of Formula (I) is compound I-6 wherein, compound I-6 is a phosphoric acid salt. In some embodiments compound I-6 is a solid. According to another aspect, compound I-6 has an X-Ray diffraction pattern substantially similar to that depicted in FIG. 6A. According to another aspect, compound I-6 has an X-Ray diffraction pattern substantially similar to that depicted in FIG. 6B. Compound I-6 can be characterized by substantial similarity to two of these figures simultaneously.

In another embodiment, a compound of Formula (I) is compound I-7 wherein, compound I-7 is a p-toluene sulfonic acid salt. In some embodiments compound I-7 is a crystalline solid. In some embodiments, compound I-7 is a crystalline solid and is Pattern S6-I. According to another aspect, compound I-7 has an X-Ray diffraction pattern substantially similar to that depicted in FIG. 7A. According to another aspect, compound I-7 has a thermogravimetric analysis pattern substantially similar to that depicted in FIG. 7B. According to yet another aspect, compound I-7 has a differential scanning calorimetry pattern substantially similar to that depicted in FIG. 7B. Compound I-7 can be characterized by substantial similarity to two or more of these figures simultaneously.

In another embodiment, a compound of Formula (I) is compound I-8 wherein, compound I-8 is a benzene sulfonic acid salt. In some embodiments compound I-8 is a crystalline solid. In some embodiments, compound I-8 is a crystalline solid and is Pattern S7-I. In some embodiments, compound I-8 is a crystalline solid and is Pattern S7-II. According to another aspect, compound I-8 has an X-Ray diffraction pattern substantially similar to that depicted in FIG. 8A. According to another aspect, compound I-8 has a thermogravimetric analysis pattern substantially similar to that depicted in FIG. 8B. According to yet another aspect, compound I-8 has a differential scanning calorimetry pattern substantially similar to that depicted in FIG. 8B. Compound I-8 can be characterized by substantial similarity to two or more of these figures simultaneously.

Figure 9A:
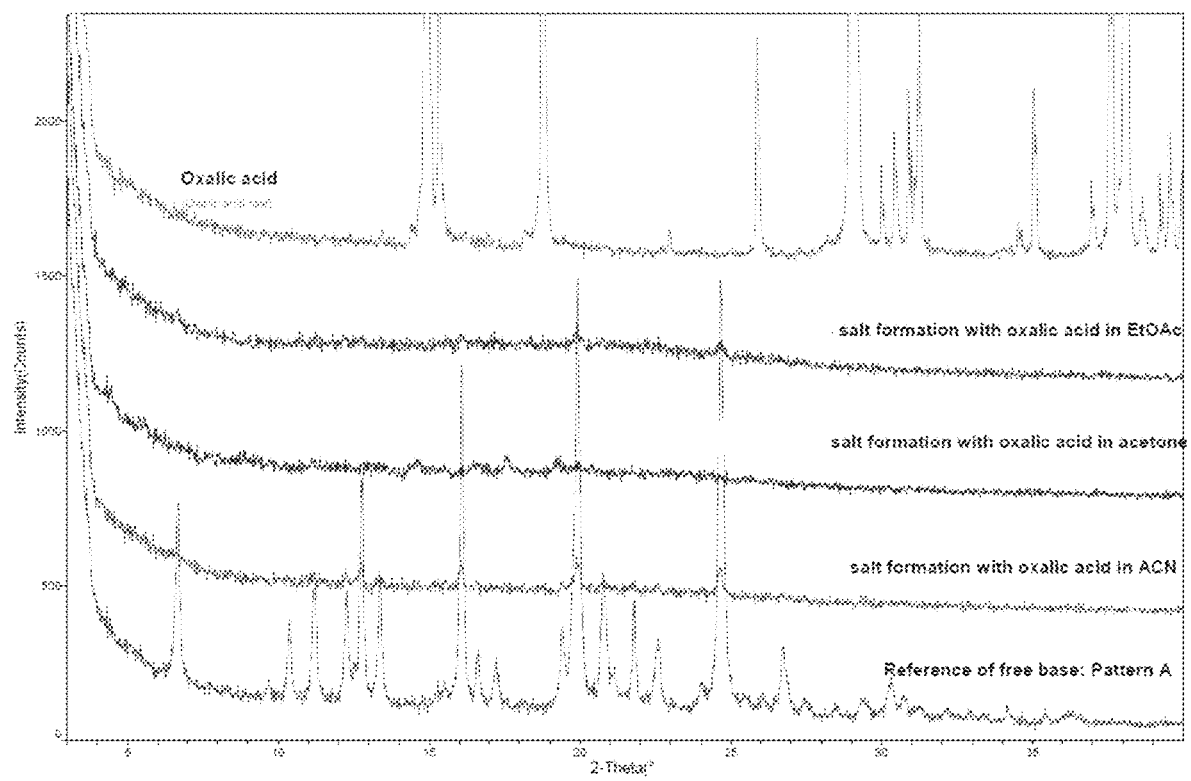
FIG. 9A depicts the characterization of X-ray diffraction pattern of Compound I-9 compared to the X-ray diffraction pattern of Pattern A of Compound I-1.
Figure 9B:
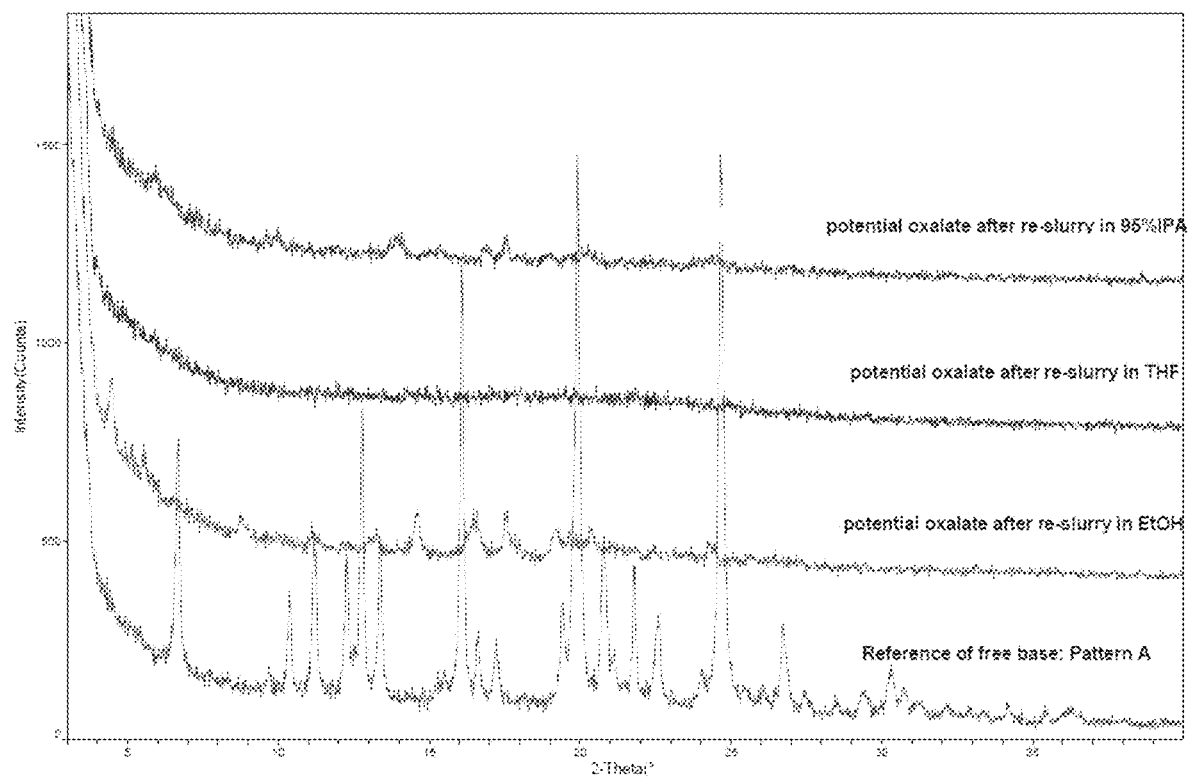
FIG. 9B depicts the characterization of X-ray diffraction pattern of Compound I-9 after re-slurry experiments compared to the X-ray diffraction pattern of Pattern A of Compound I-1.

In another embodiment, a compound of Formula (I) is compound I-9 wherein, compound I-9 is an oxalic acid salt. In some embodiments compound I-9 is a solid. According to another aspect, compound I-9 has an X-Ray diffraction pattern substantially similar to that depicted in FIG. 9A. According to another aspect, compound I-9 has an X-Ray diffraction pattern substantially similar to that depicted in FIG. 9B. Compound I-9 can be characterized by substantial similarity to two of these figures simultaneously.

Figure 10:
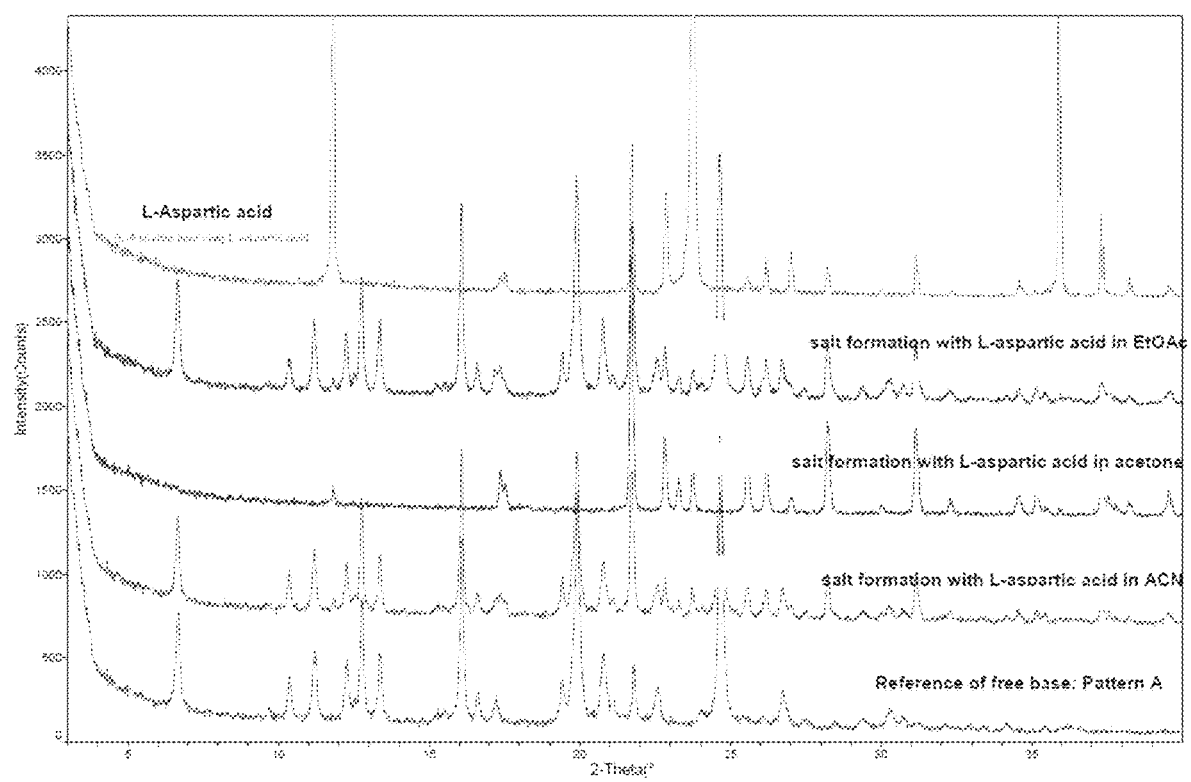
FIG. 10 depicts the characterization of X-ray diffraction pattern of Compound I-10 compared to the X-ray diffraction pattern of Pattern A of Compound I-1.

In another embodiment, a compound of Formula (I) is compound I-10 wherein, compound I-10 is an L-aspartic acid salt. In some embodiments compound I-10 is a solid. In some embodiments compound I-10 is a crystalline solid. According to another aspect, compound I-10 has an X-Ray diffraction pattern substantially similar to that depicted in FIG. 10.

Figure 11A:
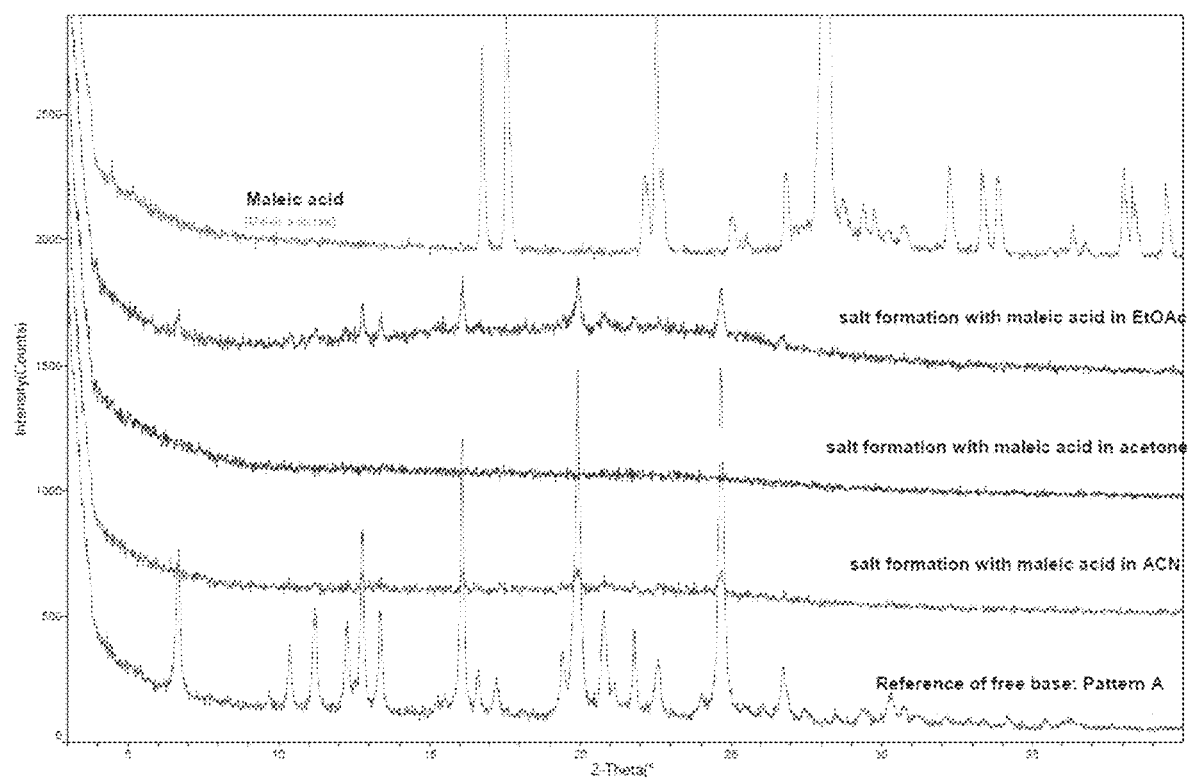
FIG. 11A depicts the characterization of X-ray diffraction pattern of Compound I-11 compared to the X-ray diffraction pattern of Pattern A of Compound I-1.
Figure 11B:
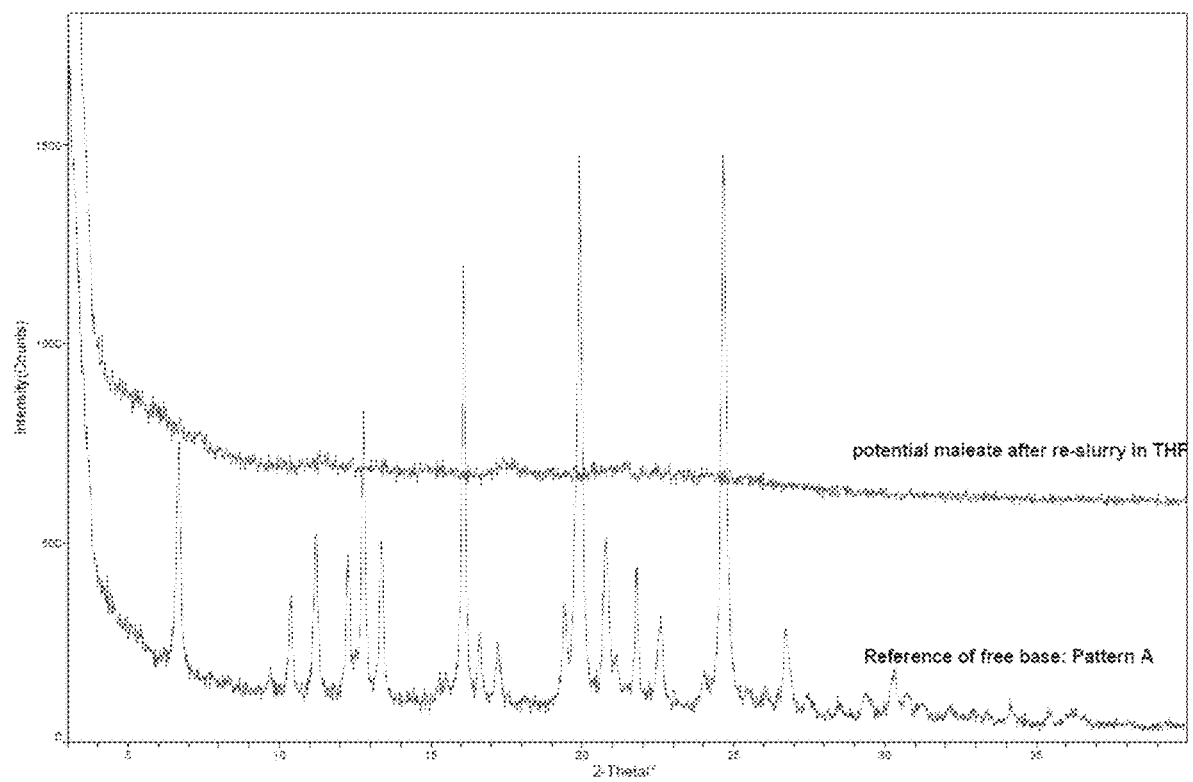
FIG. 11B depicts the characterization of X-ray diffraction pattern of Compound I-11 after re-slurry experiments compared to the X-ray diffraction pattern of Pattern A of Compound I-1.

In another embodiment, a compound of Formula (I) is compound I-11 wherein, compound I-11 is a maleic acid salt. In some embodiments compound I-11 is a solid. According to another aspect, compound I-11 has an X-Ray diffraction pattern substantially similar to that depicted in FIG. 11A. According to another aspect, compound I-11 has an X-Ray diffraction pattern substantially similar to that depicted in FIG. 11B. Compound I-11 can be characterized by substantial similarity to two of these figures simultaneously.

Figure 12A:
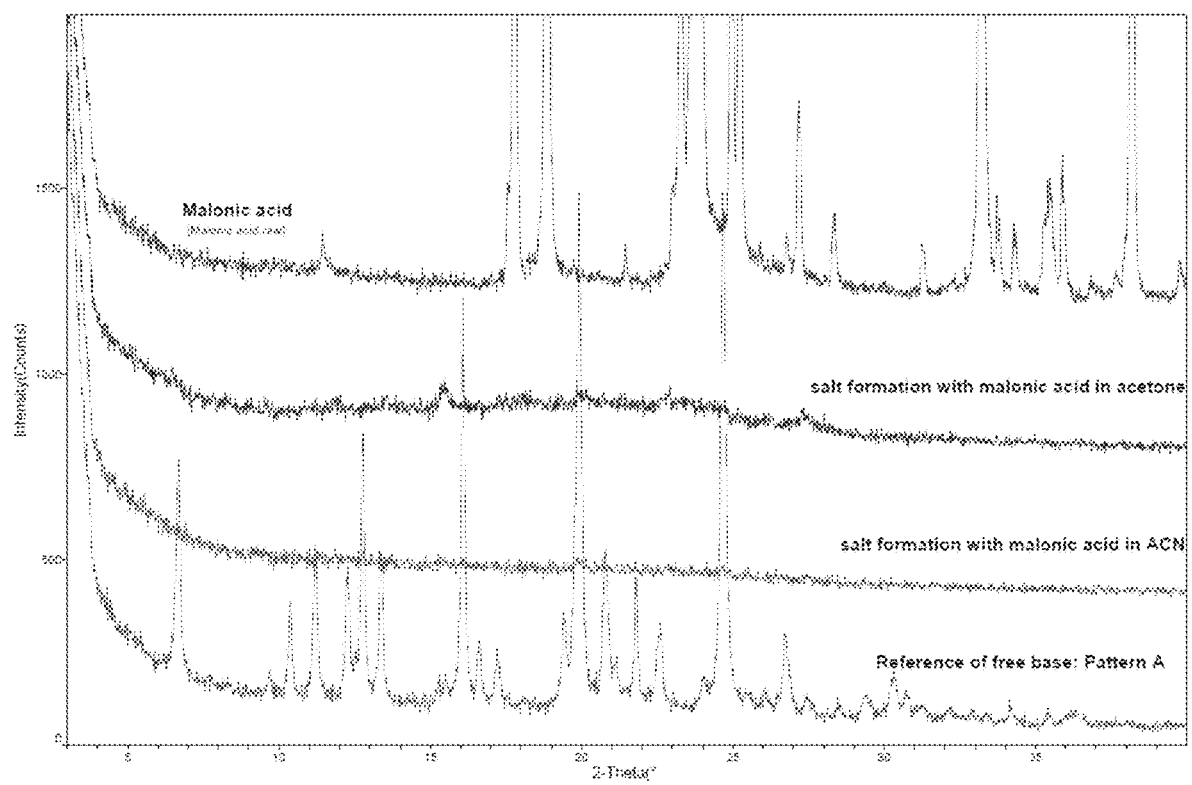
FIG. 12A depicts the characterization of X-ray diffraction pattern of Compound I-12 compared to the X-ray diffraction pattern of Pattern A of Compound I-1.

In another embodiment, a compound of Formula (I) is compound I-12 wherein, compound I-12 is a malonic acid salt. In some embodiments compound I-12 is a solid. In some embodiments compound I-12 is a crystalline solid. According to another aspect, compound I-12 has an X-Ray diffraction pattern substantially similar to that depicted in FIG. 12A. According to another aspect, compound I-12 has an X-Ray diffraction pattern substantially similar to that depicted in FIG. 12B. According to another aspect, compound I-12 has an X-Ray diffraction pattern substantially similar to that depicted in FIG. 12C. According to another aspect, compound I-12 has a thermogravimetric analysis pattern substantially similar to that depicted in FIG. 12D. According to yet another aspect, compound I-12 has a differential scanning calorimetry pattern substantially similar to that depicted in FIG. 12D. Compound I-12 can be characterized by substantial similarity to two or more of these figures simultaneously.

Figure 13A:
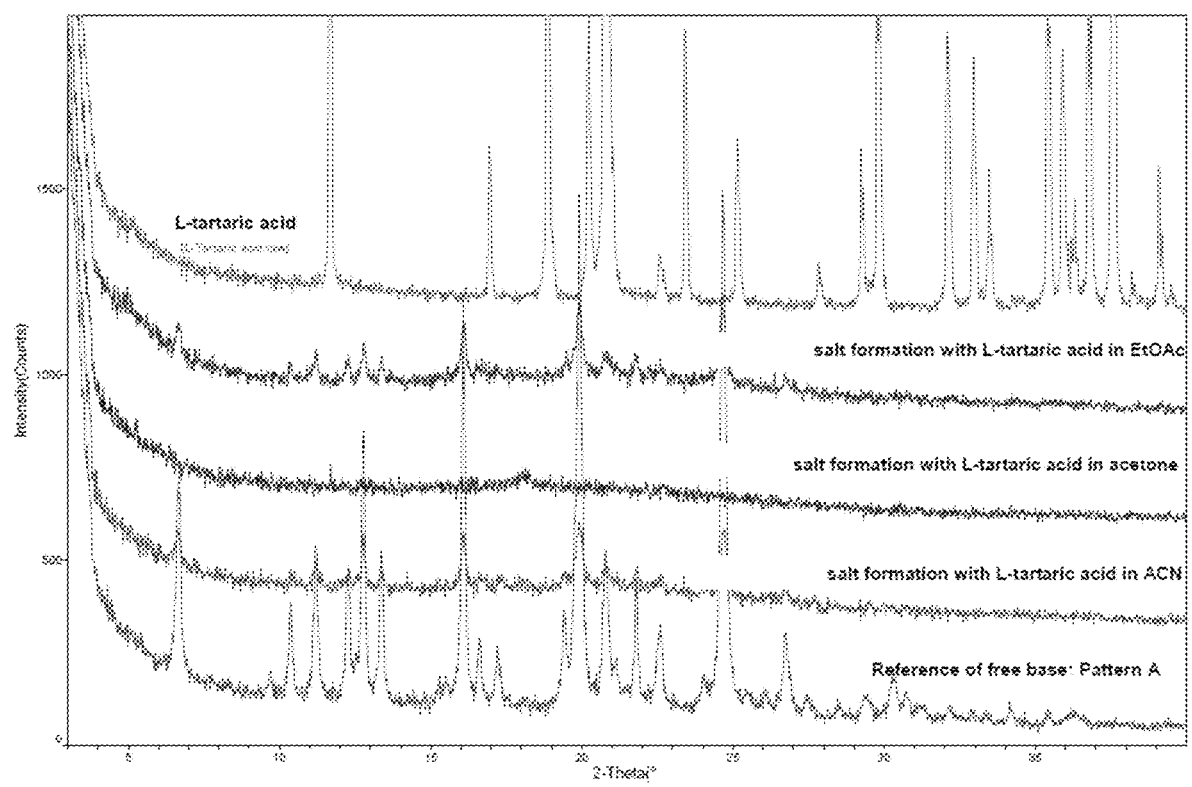
FIG. 13A depicts the characterization of X-ray diffraction pattern of Compound I-13 compared to the X-ray diffraction pattern of Pattern A of Compound I-1.
Figure 13B:
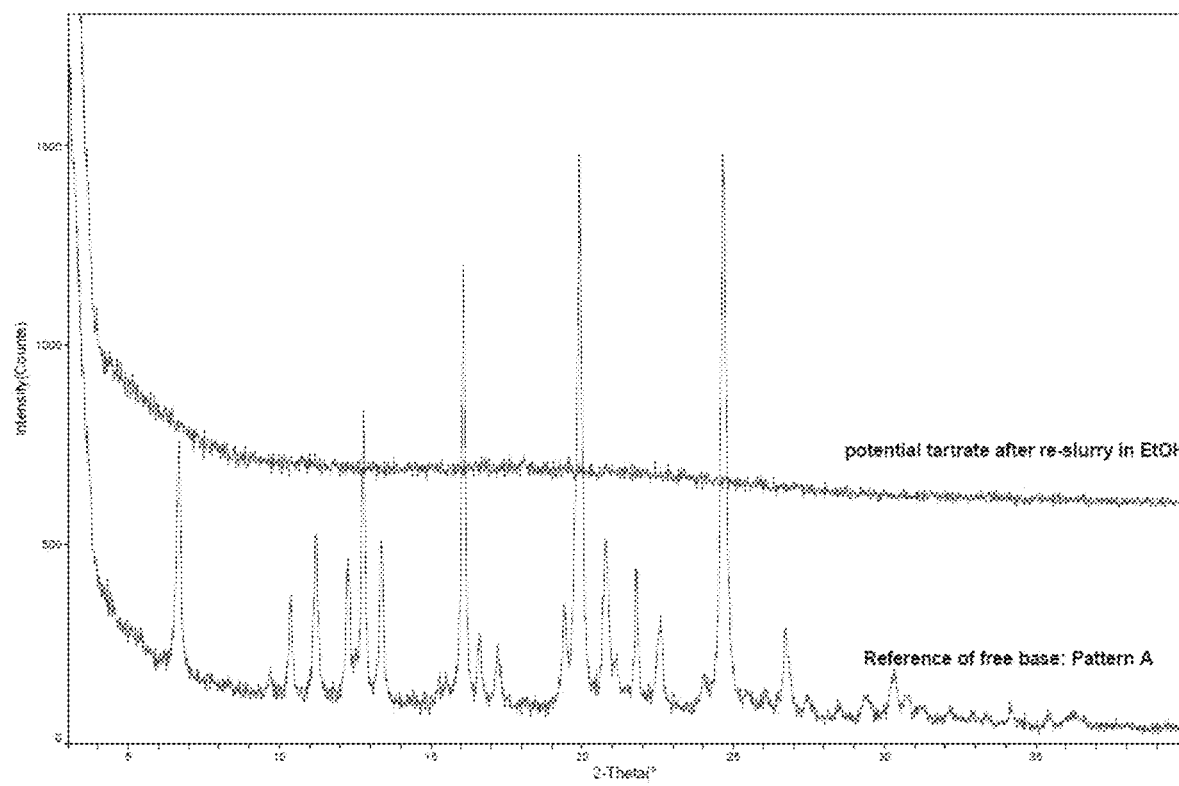
FIG. 13B depicts the characterization of X-ray diffraction pattern of Compound I-13 after re-slurry experiments compared to the X-ray diffraction pattern of Pattern A of Compound I-1.

In another embodiment, a compound of Formula (I) is compound I-13 wherein, compound I-13 is an L-tartaric acid salt. In some embodiments compound I-13 is a solid. According to another aspect, compound I-13 has an X-Ray diffraction pattern substantially similar to that depicted in FIG. 13A. According to another aspect, compound I-13 has an X-Ray diffraction pattern substantially similar to that depicted in FIG. 13B. Compound I-13 can be characterized by substantial similarity to two of these figures simultaneously.

Figure 14A:
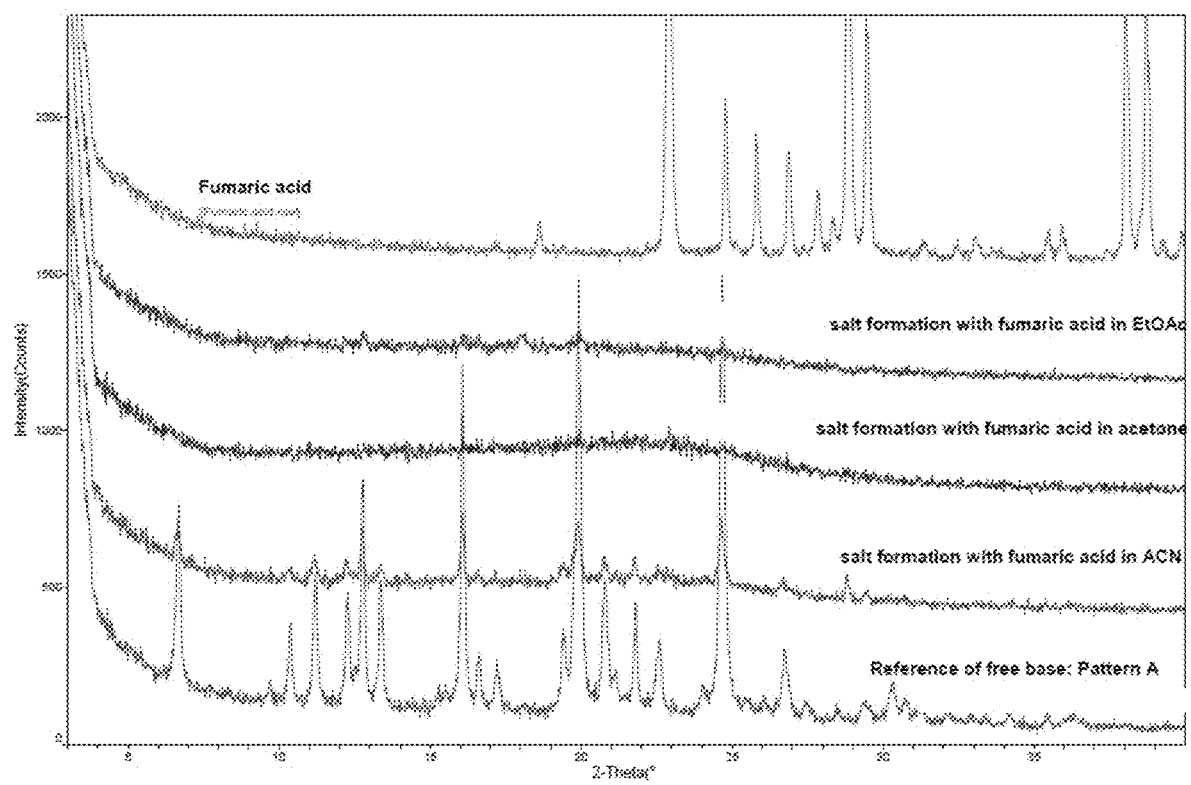
FIG. 14A depicts the characterization of X-ray diffraction pattern of Compound I-14 compared to the X-ray diffraction pattern of Pattern A of Compound I-1.
Figure 14B:
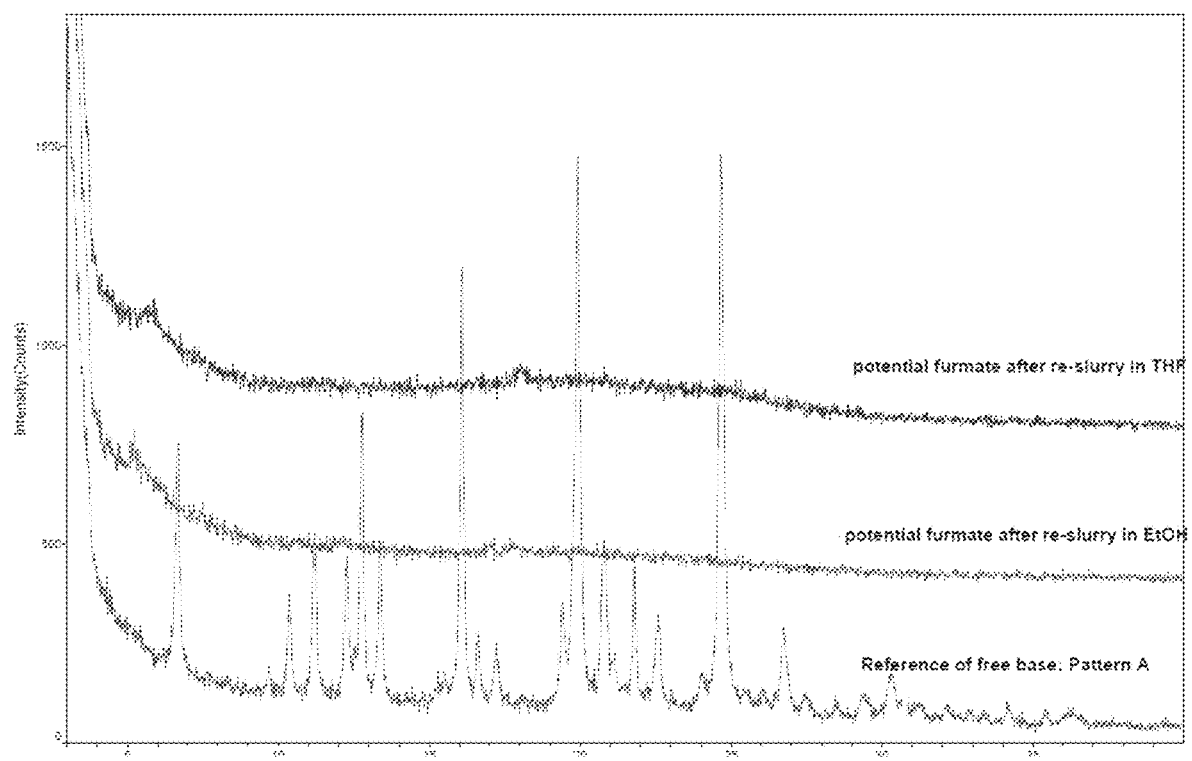
FIG. 14B depicts the characterization of X-ray diffraction pattern of Compound I-14 after re-slurry experiments compared to the X-ray diffraction pattern of Pattern A of Compound I-1.

In another embodiment, a compound of Formula (I) is compound I-14 wherein, compound I-14 is fumaric acid salt. In some embodiments compound I-14 is a solid. According to another aspect, compound I-14 has an X-Ray diffraction pattern substantially similar to that depicted in FIG. 14A. According to another aspect, compound I-14 has an X-Ray diffraction pattern substantially similar to that depicted in FIG. 14B. Compound I-14 can be characterized by substantial similarity to two of these figures simultaneously.

Figure 15A:
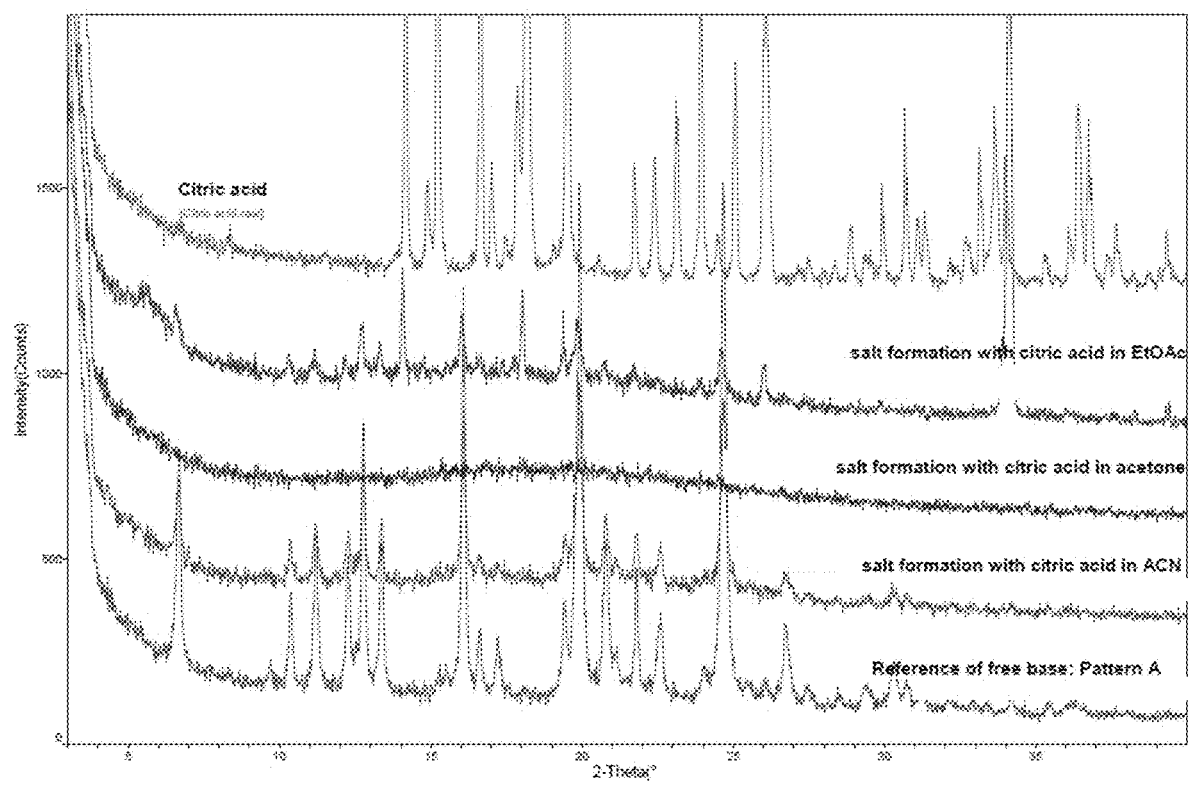
FIG. 15A depicts the characterization of X-ray diffraction pattern of Compound I-15 compared to the X-ray diffraction pattern of Pattern A of Compound I-1.
Figure 15B:
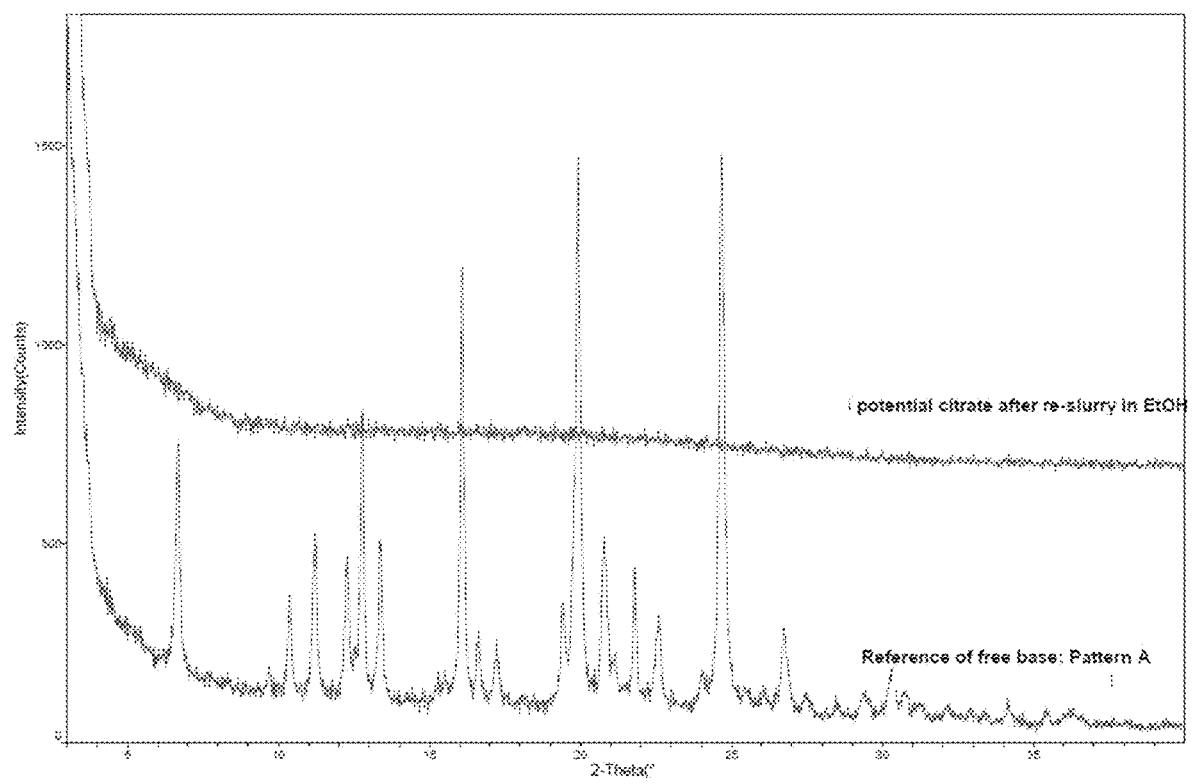
FIG. 15B depicts the characterization of X-ray diffraction pattern of Compound I-15 after re-slurry experiments compared to the X-ray diffraction pattern of Pattern A of Compound I-1.

In another embodiment, a compound of Formula (I) is compound I-15 wherein, compound I-15 is a citric acid salt. In some embodiments compound I-15 is a solid. According to another aspect, compound I-15 has an X-Ray diffraction pattern substantially similar to that depicted in FIG. 15A. According to another aspect, compound I-15 has an X-Ray diffraction pattern substantially similar to that depicted in FIG. 15B. Compound I-15 can be characterized by substantial similarity to two of these figures simultaneously.

Figure 16A:
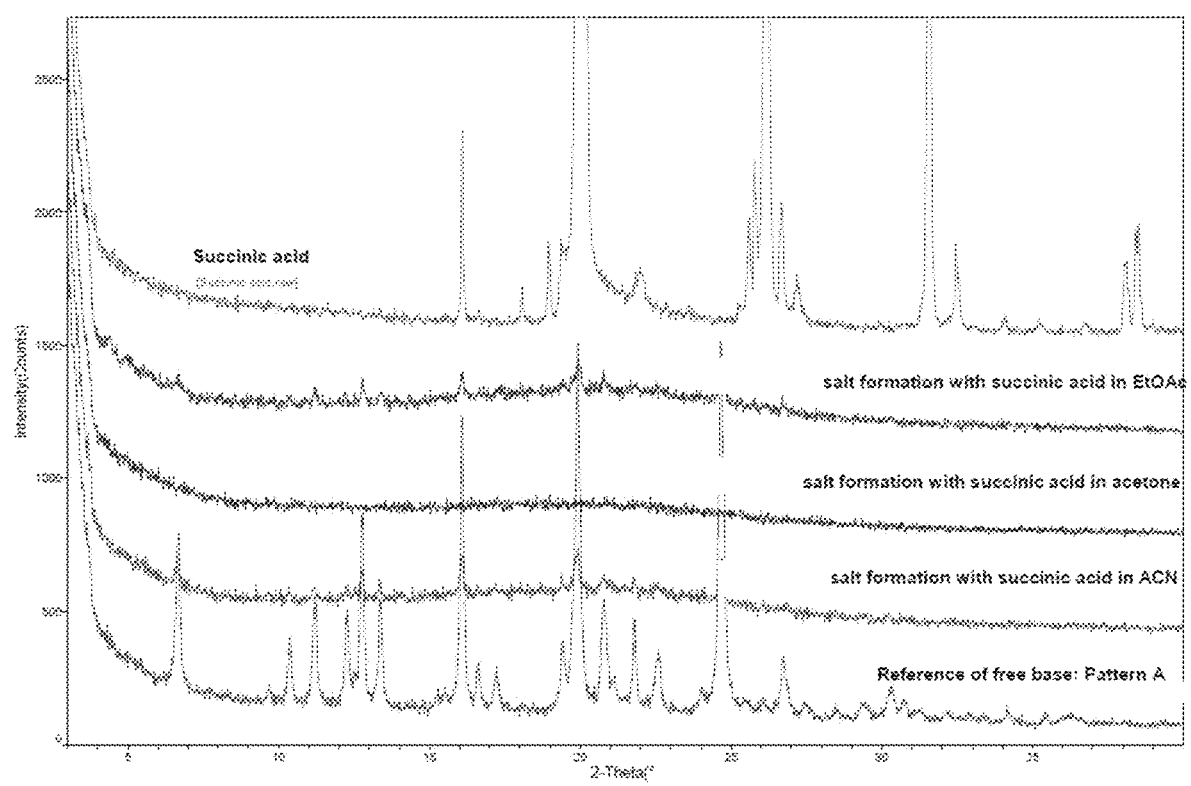
FIG. 16A depicts the characterization of X-ray diffraction pattern of Compound I-16 compared to the X-ray diffraction pattern of Pattern A of Compound I-1.
Figure 16B:
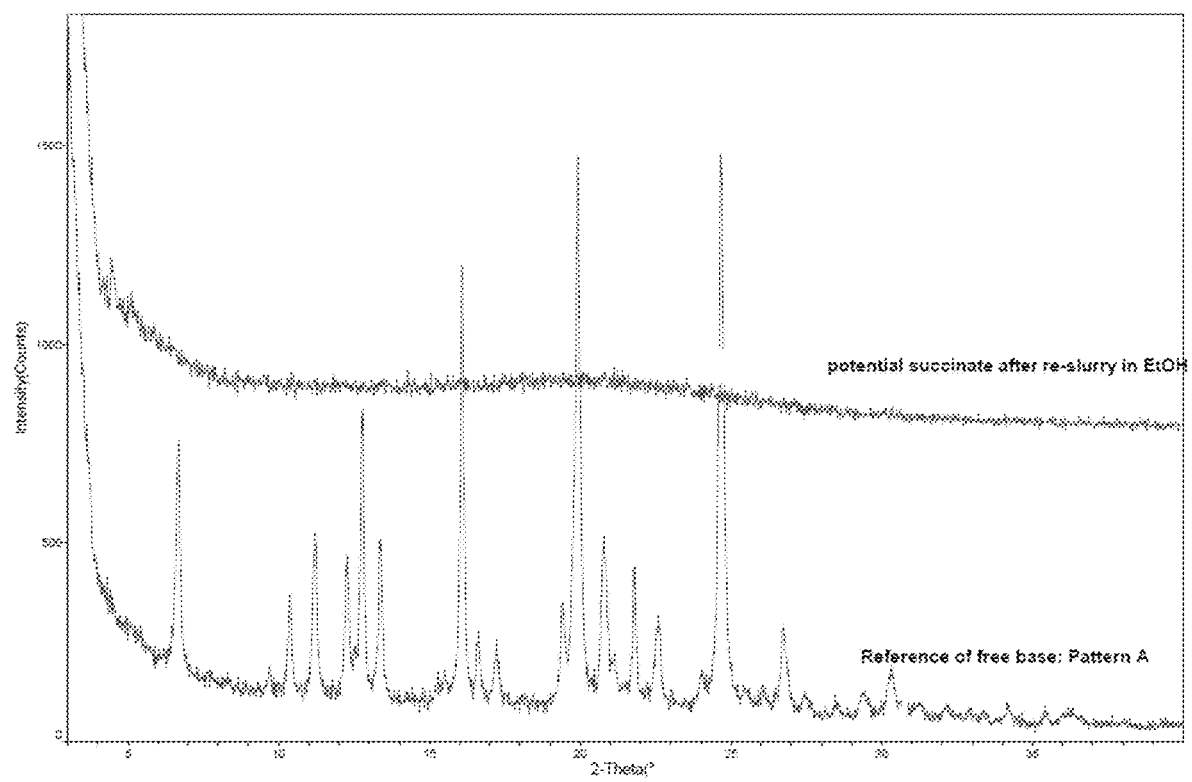
FIG. 16B depicts the characterization of X-ray diffraction pattern of Compound I-16 after re-slurry experiments compared to the X-ray diffraction pattern of Pattern A of Compound I-1.

In another embodiment, a compound of Formula (I) is compound I-16 wherein, compound I-16 is a succinic acid salt. In some embodiments compound I-16 is a solid. According to another aspect, compound I-16 has an X-Ray diffraction pattern substantially similar to that depicted in FIG. 16A. According to another aspect, compound I-17 has an X-Ray diffraction pattern substantially similar to that depicted in FIG. 16B. Compound I-16 can be characterized by substantial similarity to two of these figures simultaneously.

In another embodiment, a compound of Formula (I) is compound I-17 wherein, compound I-17 is a glutaric acid salt. In some embodiments compound I-17 is a solid. In some embodiments compound I-17 is a crystalline solid. In some embodiments, compound I-17 is a crystalline solid and is Pattern S16-I. According to another aspect, compound I-17 has an X-Ray diffraction pattern substantially similar to that depicted in FIG. 17A. According to another aspect, compound I-17 has an X-Ray diffraction pattern substantially similar to that depicted in FIG. 17B. According to another aspect, compound I-17 has an X-Ray diffraction pattern substantially similar to that depicted in FIG. 17C. According to another aspect, compound I-17 has a thermogravimetric analysis pattern substantially similar to that depicted in FIG. 17D. According to yet another aspect, compound I-17 has a differential scanning calorimetry pattern substantially similar to that depicted in FIG. 17D. Compound I-17 can be characterized by substantial similarity to two or more of these figures simultaneously.

Methods

In some embodiments, disclosed herein is a method of inhibiting SHP2 phosphatase activity in a subject in need thereof, comprising administering a therapeutically effective amount of a solid form disclosed herein, a compound disclosed herein, or a disclosed pharmaceutical composition to the subject. In other embodiments, disclosed herein is a method of treating a disorder in a subject in need thereof, comprising administering a therapeutically effective amount of a solid form disclosed herein, a compound disclosed herein, or a disclosed pharmaceutical composition to the subject. In some embodiments, the subject is a human.

In some embodiments, the methods disclosed herein may further comprise administration of a therapeutically effective amount of an antibody, an antibody-drug conjugate, an immunomodulator, or a histone deacetylase inhibitor. In some embodiments, the disorder to be treated is Noonan syndrome. In some embodiments, the disorder to be treated is neutropenia. In some embodiments, the disorder to be treated is diabetes. In some embodiments, the disorder to be treated is neuroblastoma. In some embodiments, the disorder to be treated is melanoma. In some embodiments, the disorder to be treated is acute myeloid leukemia. In some embodiments, the disorder to be treated is juvenile leukemia. In some embodiments, the disorder to be treated is juvenile myelomonocytic leukemia. In some embodiments, the disorder to be treated is breast cancer. In some embodiments, the disorder to be treated is lung cancer. In some embodiments, the disorder to be treated is colorectal cancer.

Disclosed compounds or compositions can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in Nature, 2016, doi:10.1038/nature18621; and references cited therein; each of which hereby incorporated by reference in its entirety.) Inhibition of SHP2 phosphatase also has been found to ameliorate the pathogenesis of systemic lupus erythematosus. (See, e.g., J. Wang et al., in J. Clin. Invest. 2016, 126, 2077-2092; and references cited therein; each of which hereby incorporated by reference in its entirety.)

In some embodiments, compounds or compositions of the disclosure can be useful in suppressing tumor cell growth. In some embodiments, compounds or compositions of the disclosure can be useful in ameliorating the pathogenesis of systemic lupus erythematosus. In some embodiments, compounds or compositions of the disclosure can be useful in the treatment of various other disorders, including Noonan syndrome (NS), LEOPARD syndrome (Noonan syndrome with multiple lentigines), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the disclosure can be used in combination with other treatments and/or cancer therapies. For example, compounds or compositions of the disclosure can be used in combination with, but are not limited to, antibodies, antibody-drug conjugates, kinase inhibitors, immunomodulators, and histone deacetylase inhibitors. The compounds or compositions of the disclosure can also be used in combination with other treatments and/or cancer therapies as disclosed in WO 2015/107495; and references cited therein; each of which is hereby incorporated by reference in its entirety.

For example, the compounds disclosed herein (or pharmaceutical compositions containing them) can be used in the treatment of one or more of the diseases mentioned herein, alone or in combination with another therapeutic agent. For example, a compound of Formula I, Formula II or Formula III can be used in combination with the following agents: BCR-ABL inhibitors: imatinib mesylate; nilotinib hydrochloride; nilotinib; dasatinib; bosutinib; ponatinib; bafetinib; danusertib; saracatinib; N-[2-[(S,4R)-6-[[4-(Cyclobutylamino)-5-(tjifluoromethyl)-2-pyrimidinyl]amino]-1,2,3,4-tetrahydronaphthalen-,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547. FLT3 inhibitors: sunitinib malate; midostaurin; tanutinib; sorafenib, lestaurtinib, quizartinib and crenolanib. KRAS inhibitors: MRTX849, AMG510. MEK Inhibitors—trametinib, combimetinib, binimetinib, selumetinib. VEGF receptor inhibitors: bevacizumab, axitinib, Aflibercept, (N-methyl-2-[[3-[(E)-2-pyridin-2-ylethenyl]-1H-indazol-6-yl]sulfanyl]benzamide, brivanib alaninate ((S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, motesanib (N-(2,3-dihydro-3,3-dimethyl-1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: Gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: Filgrastim. Immunomodulators: Afutuzumab, lenalidomide, thalidomide. CD40 inhibitors: Dacetuzumab. Pro-apoptotic receptor agonists (PARAs): Dulanermin. Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(1H-Indazol-4-yl)-6-[[4-(methylsulfonyl)piperazin-1-yl]methyl]thieno[3,2-d]pyrimidin-4-yl]mo choline, 2-Methyl-2-[4-[3-methyl-2-oxo-8-(quinolin-3-yl)-2,3-dihydroimidazo[4,5-c]quinolin-1-yl]phenyl]propiocyano, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl] methyl]-1-piperazinyl]-N-[[4-[[(1R)-3-(4-morpholinyl)-1-[(phenylthio)methyl]propyl] amino]-3-[(trifluoromethyl)sulfonyl]phenyl]sulfonyl]benzamide. Mitogen-activated protein kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostain analogs: octreotide. Synthetic Interleukin-11 (IL-11): oprelvekin. Synthetic erythropoietin: Darbepoetin alfa. Receptor Activator for Nuclear Factor x B (RANK) inhibitors: Denosumab. Thrombopoietin mimetic peptides: Romiplostim. Cell growth stimulators: Palifermin. Anti-Insulin-like Growth Factor-1 receptor (IGF-1R) antibodies: Figitumumab. Anti-CS1 antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL1 inhibitors: MSB0010718C; YW243.55.S70, MPDL3280A; MEDI-4736, MSB-0010718C, or MDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: *bacillus* calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists:

Eltrombopag. Anti-mitotic agents: Docetaxel. Adrenal steroid inhibitors: aminoglutethimide. Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK inhibitors: Alvocidib, palbociclib, ribociclib, trilaciclib, abemaciclib. TRK inhibitors: entrectinib, larotrectinib. RET inhibitors: BLU-667, LOXO-292. Gonadotropin-releasing hormone (GnRH) receptor agonists: Leuprolide or leuprolide acetate. Taxane anti-neoplastic agents: Cabazitaxel (1-hydroxy, 10-dimethoxy-9-oxo-5,20-epoxytax-11-ene-2a,4,13a-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate). 5HT1a receptor agonists: Xaliproden (also known as SR57746, 1-[2-(2-naphthyl)ethyl]-4-[3-(trifluoromethyl)phenyl]-1,2,3,6-tetrahydropyridine.

HPC vaccines: Cervarix® sold by GlaxoSmithKline, Gardasil® sold by Merck;

Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine.

Plant Alkaloids: Paclitaxel protein-bound; vinblastine, vincristine, vinorelbine, paclitaxel.

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Claras®, Decutan®, Isotane®, Izotech®, Oratane®, Isotret®, and Sotret®), bexarotene (sold under the tradename Targretin®). Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13 S,14S,16R,17R)-9-fluoro-11,17-dihydroxy-17-(2-hydroxy acetyl)-10,13,16-trimethyl-6,7,8,9,10,11,12, 13, 14,15, 16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®). Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®). Estrogen receptor downregulators: Fulvestrant (sold under the tradename Faslodex®). Anti-estrogens: tamoxifen (sold under the tradename Novaldex®). Toremifene (sold under the tradename Fareston®). Selective estrogen receptor modulators (SERMs): Raloxifene (sold under the tradename Evista®). Leutinizing hormone releasing hormone (LHRH) agonists: Goserelin (sold under the tradename Zoladex®);

Progesterones: megestrol (also known as megestrol acetate, sold under the tradename Megace®); Miscellaneous cytotoxic agents: Arsenic trioxide (sold under the tradename Trisenox®), asparaginase (also known as L-asparaginase, *Erwinia* L-asparaginase, sold under the tradenames Elspar® and Kidrolase®). Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid). Immune checkpoint inhibitors: The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta.

Compounds described herein can function, in certain embodiments, as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the disclosure can be used in combination with an antibody. In some embodiments, compounds or compositions of the disclosure can be used in combination with an antibody-drug conjugate. In some embodiments, compounds or compositions of the disclosure can be used in combination with a kinase inhibitor. In some embodiments, compounds or compositions of the disclosure can be used in combination with an immunomodulator. In some embodiments, compounds or compositions of the disclosure can be used in combination with a histone deacetylase inhibitor.

In some embodiments, disclosed compounds can be administered to a subject in need of treatment at dosages ranging from about 0.0001 mg to about 100 mg/kg body weight of the subject to be treated per day, such as from about 1.0 to 10 mg/kg. However, additional variations are within the scope of the disclosure.

A disclosed compound can be administered alone or in combination with pharmaceutically acceptable carriers, such as diluents, fillers, aqueous solution, and even organic solvents. The compound and/or compositions of the disclosure can be administered as a tablet, powder, lozenge, syrup, injectable solution, and the like. Additional ingredients, such as flavoring, binder, excipients, and the like are within the scope of the disclosure.

In some embodiments, the present disclosure provides for the use of pharmaceutical compositions and/or medicaments comprised of a compound disclosed herein, or a pharmaceutically acceptable salt thereof, in a method of treating a disease state, and/or condition caused by or related to SHP2 phosphatase. For example, provided herein are methods of treating subjects in need thereof (e.g., subjects suffering from cancer (e.g., leukemia, breast, lung and/or colorectal cancer) an effective amount of a disclosed compound, and optionally an effective amount of an additional compound (e.g., therapeutic agent) such as disclosed herein.

In some embodiments, a method of treatment comprises the steps of: i) identifying a subject in need of such treatment; (ii) providing a compound disclosed herein, or a pharmaceutically acceptable salt thereof; and (iii) administering said compound in a therapeutically effective amount to treat, suppress and/or prevent the disease state or condition in a subject in need of such treatment.

In some embodiments, a method of treatment comprises the steps of: i) identifying a subject in need of such treatment; (ii) providing a composition comprising a compound disclosed herein, or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the method of treatment, prevention and/or suppression of a condition related to SHP2 phosphatase comprises the steps of: i) identifying a subject in need of such treatment; (ii) providing a compound disclosed herein or a pharmaceutically acceptable salt thereof; or a composition comprising a compound disclosed herein, or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In accordance with the methods of the present disclosure, the compounds of the disclosure are administered to the subject in a therapeutically effective amount, e.g., to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range and may be combined with any other dosage to constitute a dosage range comprising an upper and lower limit.

Compositions

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, topical, buccal, ocular, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral, subcutaneous or intravenous administration.

Exemplary pharmaceutical compositions of this disclosure may be used in the form of a pharmaceutical preparation, for example, in solid, semisolid or liquid form, which contains one or more of the compounds of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments, pharmaceutically acceptable compositions can contain a disclosed compound and/or a pharmaceutically acceptable salt thereof at a concentration ranging from about 0.01 to about 2.0 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, 5$^{th}$ Ed. (Alexander T. Florence, Juergen Siepmann, CRC Press (2009)); Handbook of Pharmaceutical Excipients, 7$^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the compounds of the disclosure are formulated into pharmaceutical compositions for administration to subjects in a biologically compatible form suitable for administration in vivo. According to another aspect, the present disclosure provides a pharmaceutical composition comprising a disclosed compound in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium acetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the disclosed compound and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present disclosure are administered to a human or animal subject by known procedures including oral administration, sublingual or buccal administration. In some embodiments, the compound and/or composition is administered orally.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

For oral administration, a formulation of the compounds of the disclosure may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A nonaqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. For example, crystalline forms provided herein may be milled to obtain a particular particle size, and in at least some embodiments, such crystalline forms may remain substantially stable upon milling.

For example, provided herein is a composition suitable for subcutaneous administration, comprising a suspension of the disclosed crystalline form. Subcutaneous administration can be advantageous over intravenous administration, which typically requires a doctor visit, and can be more painful and invasive. A typical dose of the crystalline compound, when administered to a patient, may be about 1 mg to about 8 mg of compound. In an embodiment, disclosed herein is a pharmaceutically acceptable composition formed from a disclosed crystalline form, e.g. by mixing a crystalline form with an excipient and/or a solvent.

In an embodiment, provided herein is a composition comprising a disclosed crystalline form suitable for subcutaneous administration at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.001 mg/kg to about 4 mg/kg, from about 0.1 mg/kg to about 10 mg/kg, from about 1 mg/kg to about 25 mg/kg, of subject body weight, administered daily, one or more times a day, every other day, every third or fourth day, every week, every two weeks, every three weeks, or every four weeks. In certain embodiments, the desired dosage may be delivered using multiple administrations (e.g., two, three, four, five, six, seven, eight, nine, or ten administrations). In certain embodiments, administration may occur once, twice, or thrice weekly.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. lower dose sufficient to weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

For example, provided herein is a drug substance comprising at least a detectable amount of a disclosed crystalline form, e.g., a crystalline form of a compound of Formula (I). In certain embodiments, a contemplated drug substance may comprise at least about, e.g., 10%; at least about, e.g., 50%; or at least about, e.g., at least about 90% of a disclosed crystalline form, e.g., a crystalline form of a compound of Formula (I). In certain embodiments, a contemplated drug substance may comprise a substantially pure crystalline form of a compound of Formula (I).

Kits

In one embodiment, a kit for treating or mitigating a contemplated disease of disorder is provided. For example, a disclosed kit comprises a disclosed crystalline compound, e.g. a crystalline form of a compound of Formula (I), disposed in an e.g. first container. In some embodiments, a kit may further include a pharmaceutically acceptable excipient, disposed in e.g. a second container. Such contemplated kits may include written instructions describing preparation of a pharmaceutical composition suitable for administration to a patient from the crystalline form. For example, the written instructions may describe preparing a pharmaceutically acceptable form for patient administration by e.g. mixing an excipient and a crystalline compound disclosed herein. Disclosed kits may further comprise written instructions describing how to administer the resulting composition to the patient.

Processes

In some embodiments, a process for preparing a disclosed, crystalline form of a compound of Formula (I), e.g., compound I-1, is contemplated herein, comprising: a) preparing a solution of compound I-1 in a solvent comprising at least one of EtOH, ACN, MEK, EtOAc, IPAc, THF, MtBE, Toluene, 1,4 dioxane and water; b) heating the solution to completely dissolve the compound I-1; c) adjusting the temperature so that solid precipitates out of the solution; and d) isolating the crystalline form of compound I-1.

In some embodiments, the solvent is EtOH. In some embodiments, the solvent comprises CAN. In some embodiments, the solvent comprises EtOAc. In some embodiments, the solvent comprises IPAc. In some embodiments, the solvent comprises THF. In some embodiments, the solvent comprises MtBE. In some embodiments, the solvent comprises Toluene. In some embodiments, the solvent comprises 1,4 dioxane. In some embodiments, the solvent comprises EtOH and water (9v/1v). In some embodiments, heating the solution comprises heating the solution to about 50° C. In some embodiments, adjusting the temperature comprises cooling the solution to about 5° C.

Further disclosed herein is a process for preparing a compound of Formula I-1, the process comprising the step of neutralizing a compound of Formula I-3 with NaOH, thereby forming the compound of Formula I-1:

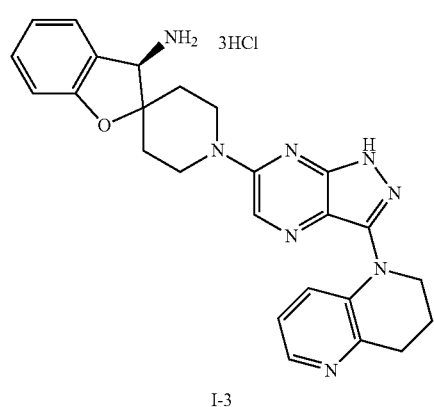

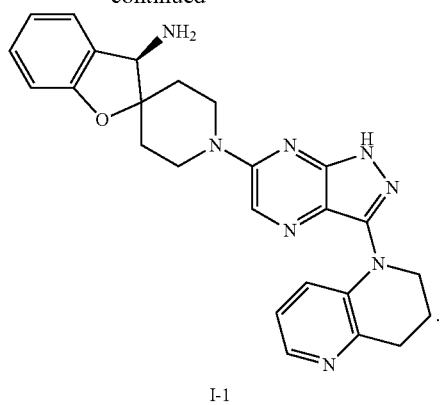

I-1

In some embodiments, a disclosed process further comprises the step of reacting a compound of Formula 18 with HCl, thereby forming the compound of Formula I-3:

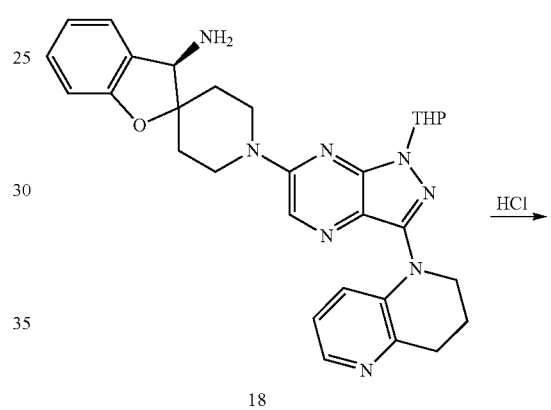

18

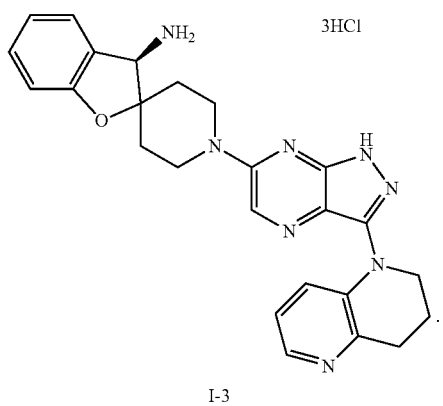

I-3

In other embodiments, a disclosed process further comprises the step of coupling a compound of Formula 17 with compound of Formula 9, thereby forming the compound of Formula 18:

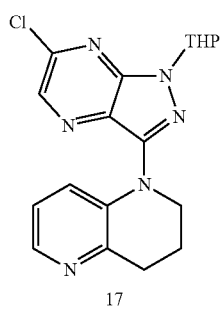

17

+

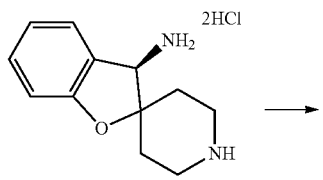

9

→

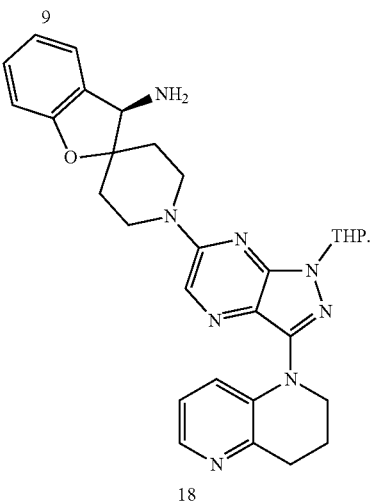

18

EXAMPLES

The compounds described herein can be prepared in a number of ways based on the teachings contained herein and synthetic procedures known in the art. The following non-limiting examples illustrate the disclosed disclosures.

X-ray Powder Diffraction (XRPD): XRPD analysis was carried out on a Bruker D8 Advance. Samples were run on XRPD using below method:

Tube: Cu: K-Alpha ($\lambda$=1.54179 Å).
Generator: Voltage: 40 kV; Current: 40 mA.
Scan Scope: 3 to 40 deg;
Sample rotation speed: 15 rpm.
Scanning rate: 10 deg./min.

Differential Scanning Calorimetry (DSC): DSC analysis was carried out on a TA Instruments Q2000. Details of DSC method used in the tests are mentioned as below:

Heating from 30° C. to 250° C. at 10° C./min
Cycle DSC method used:
Cycle1: Heating from 30° C. to 300° C. at 10° C./min
Cycle2: cooling from 300° C. to 30° C. at 10° C./min
Cycle3: heating from 30° C. to 300° C. at 10° C./min Thermal Gravimetric Analysis (TGA): TGA was carried out on a TA Instruments Q5000 IR. Details of TGA method used in the characterization are mentioned below:

Heat from 30° C. to 300° C. at 10° C./min

Dynamic Vapour Sorption (DVS): Around 10-20 mg sample was used to test its moisture sorption/desorption profiles at 25° C. under 0%~90%~0% relative humidity (RH) cycle with the following parameters:

Equilibrium: dm/dt: 0.01%/min. (for min: 10 min and max: 180 min).
Drying: 0% RH for 120 min.
RH (%) measurement step:10%
RH (%) measurement step scope: 0~90~0%

| Hygroscopicity Classification | Water Sorption Criterion* |
|---|---|
| Deliquescent | Sufficient water is absorbed to form a liquid |
| Very Hygroscopic | W % ≥ 15% |
| Hygroscopic | W % ≥ 2% |
| Slightly Hygroscopic | W % ≥ 0.2% |
| Non-hygroscopic | W % ≤ 0.2% |

*At 25 = 1° C. and 80 ± 2% RH (European Pharmacopoeia 6.0)

Example 1—Synthesis of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine (Compound I-1)

Step 1. Preparation of Compound 1

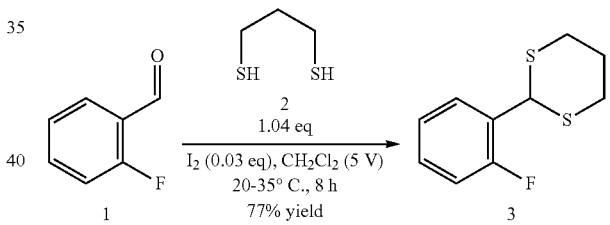

75.0 L of DCM was charged into a 200 L enamel reactor and stirred by strong magnetic stirrer. 15.0 kg of compound 1 was added in one portion. 0.931 kg of 12 was added in one portion. 13.5 kg of compound 2 was added drop-wise at 25-35° C. The reaction mixture was stirred at 20~25° C. for 8 hrs. TLC analysis (petroleum ether=1) indicated compound 1 ($R_f$=0.7) was consumed and one new spot was observed. To the reaction mixture was added $Na_2SO_3$ solution (6.00 kg $Na_2SO_3$ in 60.0 L $H_2O$), and the mixture was stirred for 0.5 hr at 25-30° C. The organic layer was separated and washed with brine (40.0 L). The organic layer was dried with $Na_2SO_4$ (10.0 kg), filtered and the filtrate was concentrated under reduced pressure at 40° C. When ~90% of DCM was removed, petroleum ether was added to the mixture and stirred for 2 hrs at 25-30° C. The mixture was filtered and the solid was dried in a drying oven at 40° C. for 8 hrs. Compound 3 (20.0 kg, yield: 77%) was obtained as a white solid, which was confirmed by $^1$H NMR. $^1$H NMR: (400 MHz CDCl$_3$) δ 7.66-7.62 (m, 1H), 7.32-7.26 (m, 1H), 7.19-7.15 (m, 1H), 7.09-7.04 (m, 1H), 5.57 (s, 1H), 3.17-3.10 (m, 2H), 2.96-2.91 (m, 2H), 2.23-2.16 (m, 1H), 2.04-1.89 (m, 1H)

Step 2. Preparation of Compound 5

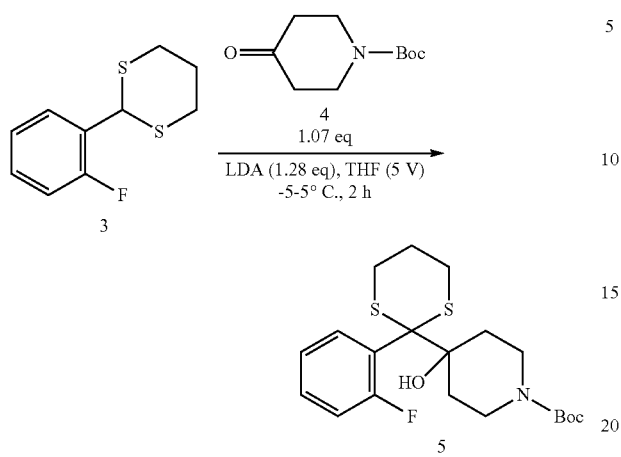

60.0 L THF was charged into a 500 L enamel reactor and stirred by strong magnetic stirrer. 20.0 kg of compound 3 was added in one portion. 60.0 L of LDA (1.28 equivalents) was added drop-wise at −5° C. to 5° C. under $N_2$. The mixture was stirred for 1 hr at −5° C. to 5° C. under $N_2$. 20.0 kg of compound of 4 in 40.0 L TH was added drop-wise at −5° C. to 5° C. under $N_2$. The mixture was stirred for 1 hr at −5° C. to 5° C. under $N_2$. TLC analysis (petroleum ether/ethyl acetate=5/1) indicated ~10% of compound 3 ($R_f$=0.7) was retained and one new spot ($R_f$=0.3) was observed. Sat. aqueous $NH_4Cl$ (250 L) was charged into a 500 L enamel reactor and stirred by strong magnetic stirrer. The reaction mixture was added and stirred for 0.5 hr. The organic layer was separated and washed with sat. aqueous $NH_4Cl$ (250 L). The organic layer was dried with $Na_2SO_4$ (15.0 kg), filtered and the filtrate was concentrated under reduced pressure at 40° C. When ~90% of THF was removed, petroleum ether (50.0 L) was added and the mixture was stirred for 1 hr at 25° C. The mixture was filtered, and the white solid was dried under reduced pressure at 45° C. Compound 5 (28.0 kg, yield: 72.5%) was obtained as white solid.

Step 3. Preparation of Compound 6

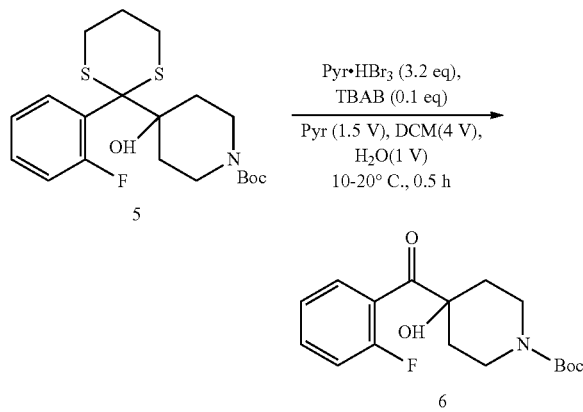

112 L of DCM, 41.0 kg of Py and 28.0 kg of H2O were charged into a 500 L enamel reactor and stirred by strong magnetic stirrer. 28.0 kg of compound 5 and 2.20 kg of TBAB was added in one portion. 70.0 kg of Py·$HBr_3$ was added portion-wise at 10-20° C. The reaction mixture was stirred for 0.5 hr at 10-20° C. TLC analysis (petroleum ether/ethyl acetate=3/1) indicated compound 5 ($R_f$=0.3) was can consumed and one new spot ($R_f$=0.3) was observed. To the reaction mixture was added 90.0 L of $H_2O$, and the mixture was stirred for 1 hr. The organic layer was separated and washed with citric acid solution (10.0 kg citric acid in 100 L $H_2O$). The organic layer was washed with sat. $NaHCO_3$ (100 L). The organic layer was dried with $Na_2SO_4$ (15.0 kg), filtered and the filtrate was concentrated under reduced pressure at 45° C. Compound 6 was obtained as red oil, which was used directly in the next step.

Step 4. Preparation of Compound 7

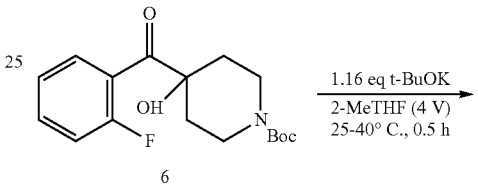

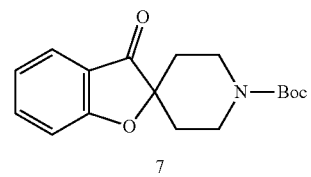

Compound 6 (21.9 kg) was dissolved in 80.0 L of 2-MeTHF, and the mixture was charged into a 200 L enamel reactor and stirred by strong magnetic stirrer. 8.80 kg of t-BuOK was added portion-wise at 25-40° C. The reaction mixture was stirred for 1 hr at 40° C. TLC analysis (petroleum ether/ethyl acetate=3/1) indicated compound 6 was consumed and one new spot ($R_f$=0.6) was observed. The reaction mixture was cooled to 25° C. 80.0 L of $H_2O$ was added slowly to the mixture at 20-25° C. and stirred for 0.5 hr. The organic layer was separated and dried with $Na_2SO_4$ (10.0 kg), filtered and the filtrate was concentrated under reduced pressure at 45° C. MTBE (30.0 L) was added when 90% of 2-MeTHF was removed. The mixture was stirred for 1 hr at 20° C. The mixture was filtered, and the white solid was obtained. The white solid was dried under reduced pressure at 45° C. Compound 7 (8.20 kg) was obtained as white solid, which was confirmed by $^1H$ NMR. $^1H$ NMR: (400 MHz $CDCl_3$) δ 7.64-7.54 (m, 2H), 7.09-6.99 (m, 2H), 4.08 (br s, 2H), 3.34-3.01 (m, 2H), 1.92-1.84 (m, 2H), 1.51 (br d, J=16.0 Hz, 2H), 1.42 (s, 9H).

Step 5. Preparation of Compound 8

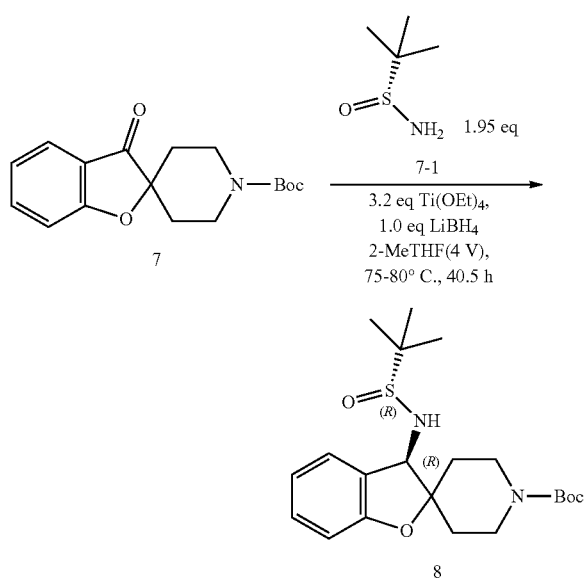

(The reaction disclosed in Step 5 was performed in 2 parallel batches.)

16.0 L of 2-MeTHF was charged into a 50 L reaction still and stirred by strong magnetic stirrer. 4.10 kg of compound 7, 3.28 kg of compound 7-1 and 10.2 kg of Ti(OEt)$_4$ were added in one portion. The reaction mixture was heated to 75° C. and stirred for 40 hrs at 75-80° C. under N$_2$. TLC analysis (petroleum ether/ethyl acetate=3/1) indicated a small amount of compound 7 ($R_f$=0.7) was retained and one new spot ($R_f$=0.5) was observed. The reaction mixture was cooled to 0° C. 300 g of LiBH$_4$ was added portion-wise at 0-10° C. under N$_2$. The reaction mixture was stirred for 0.5 hr at 0-10° C. under N$_2$. TLC analysis (petroleum ether/ethyl acetate=3/1) indicated the spot ($R_f$=0.5) was consumed and one new spot ($R_f$=0.3) was observed. To the reaction mixture was added MeOH (4.00 L) slowly at 25-30° C. About 80.0 L of mixture was obtained. 8.00 kg of EDTE was added to the mixture and stirred for 1 hr. 10.0 L of the mixture was added to citric acid (20.0 L, 10% water solution) and ethyl acetate (10.0 L). The organic layer was separated and washed with NaHCO$_3$ (10.0 L, 10% water solution). Eight batches of organic layers were obtained and dried with Na$_2$SO$_4$ (10.0 kg), filtered and the filtrate was concentrated under reduced pressure at 45° C. To the crude product was added MTBE (20.0 L) and the mixture was stirred for 1 hr. The mixture was filtered, and the cake was obtained. To the filter cake was added DCM (40.0 L) and filtered with silica gel (3.00 kg). The filtrate was concentrated under reduce pressure at 45° C. Then MTBE (15.0 L) was added to the crude product and stirred for 1 hr. The mixture was filtered, and a white solid was obtained. The white solid was dried under reduce pressure at 40° C. Compound 8 (5.40 kg, yield: 50%) was obtained, which was confirmed by HPLC and $^1$H NMR. $^1$H NMR: (400 MHz CDCl$_3$) δ 7.26-7.12 (m, 2H), 6.86-6.83 (m, 1H), 6.74 (d, J=8.0 Hz, 1H), 4.56 (br d, J=8.0 Hz, 1H), 4.01 (br s, 2H), 3.61 (br d, J=8.0 Hz, 1H), 3.2-2.90 (m, 2H), 2.03-1.57 (m, 4H), 1.39 (s, 9H), 1.18 (s, 9H).

Step 6. Preparation of Compound 9

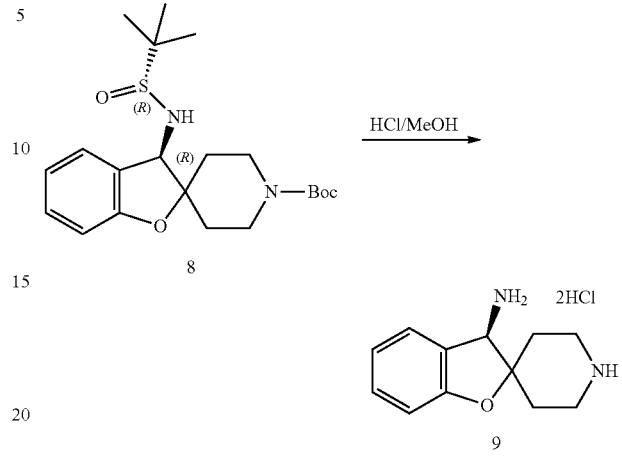

6.00 L of MeOH was charged into a 50 L reaction still and stirred by strong magnetic stirrer. 5.40 kg of compound 8 was added in one portion. HCl/MeOH (22.0 L) was added slowly to the mixture at 20-25° C. The mixture was stirred for 4 hrs at 20-25° C. TLC analysis (ethyl acetate=1) indicated compound 8 was consumed and one new spot ($R_f$=0) was observed. The reaction mixture was concentrated under reduced pressure at 45° C. Then MTBE (20.0 L) was added when most of the MeOH was removed. The mixture was stirred for 0.5 hr. The mixture was filtered, and a white solid was obtained. The white solid was dried under reduced pressure at 45° C. Compound 9 (3.30 kg, yield: 91%) was obtained as a white solid, which was confirmed by $^1$H NMR, LCMS, HPLC, and SFC. $^1$H NMR: (400 MHz DMSO_d$_6$) δ 9.69-9.27 (m, 2H), 9.03 (br s, 3H), 7.76 (d, J=8.0 Hz, 1H), 7.43-7.29 (m, 1H), 7.09-6.89 (m, 2H), 4.73 (br s, 1H), 3.44 (br d, J=12.0 Hz, 1H), 3.22 (br d, J=12.0 Hz, 1H), 3.16 (s, 1H), 3.14-2.95 (m, 2H), 2.42 (dt, J=4.0, 13.4 Hz, 1H), 2.15 (br d, J=12.0 Hz, 1H), 2.08-1.94 (m, 1H), 1.85 (br d, J=12.0 Hz, 1H)

Step 7. Preparation of Compound 11

This procedure was performed over fifteen batches. To a solution of n-BuLi (2.5 M in hexane, 6.50 L, 1.21 eq) in 2-methyltetrahydrofuran (10.0 L) was added TMP (2.87 kg, 20.3 mol, 3.45 L, 1.51 eq) at −30° C. under N$_2$ over 0.5 h.

The reaction mixture was warmed to 0° C. to 10° C. and stirred for additional 0.5 h. The reaction mixture was cooled to −75° C., and a solution of compound 10 (2.00 kg, 13.4 mol, 1.00 eq) in 2-methyltetrahydrofuran (10.0 L) was added dropwise to the mixture at −75° C. to −70° C. over 2 h. After the mixture was stirred for 0.5 h, ethyl formate (1.52 kg, 20.5 mol, 1.65 L, 1.53 eq) was cooled to −70° C. to −60° C., then poured into the reaction mixture in one portion at −75° C. The reaction mixture was stirred for an additional 0.5 h. TLC analysis (Petroleum ether/Ethyl acetate=5/1) showed compound 1 ($R_f$=0.80) was consumed and a new spot ($R_f$=0.50) was observed. Acetic acid (4.00 L) was poured into the reaction mixture in one portion at −75° C. to −30° C., was warmed to 25° C. and stirred for 0.5 h. The mixture was poured into 30.0 L water and extracted with ethyl acetate (5.00 L×3). The combined organic layers were washed with brine (5.00 L×3), dried with $Na_2SO_4$, then filtered. The filtrate was concentrated under reduced pressure to give a black brown liquid. The crude product was used into the next step without further purification. 15 batches were carried in parallel to give compound 11 (52.5 kg, crude) as black brown liquid, which was confirmed by $^1H$ NMR. $^1H$ NMR: 400 MHz, DMSO-$d_6$ 10.12 (s, 1H), 9.05 (s, 1H).

Step 8. Preparation of Compound 12

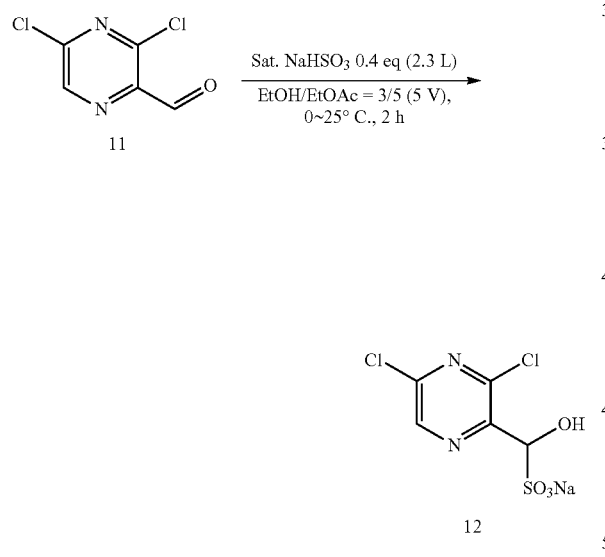

This procedure was performed over eight batches. To a solution of compound 11 (6.56 kg, 37.1 mol, 1.00 eq) in EtOAc (22.0 L) and EtOH (13.0 L) was added $NaHSO_3$ (1.54 kg, 14.8 mol, 0.40 eq) in water (2.30 L) at 0° C., and the reaction mixture was stirred at 25° C. for 12 h. TLC analysis (Petroleum ether/Ethyl acetate=5/1) showed compound 11 ($R_f$=0.15) was consumed and a new spot ($R_f$=0) was observed. The reaction mixture was filtered at 25° C., and the filter cake was dried under reduced pressure to give the crude product. The crude product was used into the next step without further purification. 8 batches were prepared in parallel to give compound 12 (35.6 kg, crude) as a gray solid which was confirmed by $^1H$ NMR. $^1H$ NMR: 400 MHz, DMSO-$d_6$ (Note: residual DMF was observed in the $^1H$ NMR spectrum for quantitative test.) 8.63 (s, 1H), 5.67 (s, 1H).

Step 9. Preparation of Compound 13

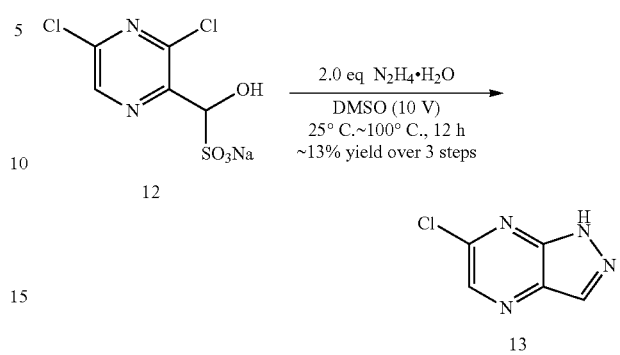

This procedure was performed over thirteen batches. To a solution of compound 12 (3.0 kg, 10.7 mol, 1.00 eq) in DMSO (30.0 L) was added $N_2H_4·H_2O$ (1.26 kg, 21.4 mol, 1.22 L, 85.0% purity, 2.00 eq) dropwise at 10° C., and the reaction mixture was stirred at 25° C. for 1 h. HPLC analysis of the reaction mixture showed compound 12 (Rt=1.003 min) was consumed. The reaction mixture was warmed to 100° C. and stirred at 100° C. for 12 h. TLC analysis (Petroleum ether:Ethyl acetate=2:1) showed a major new spot ($R_f$=0.6) was detected. HPLC of the reaction mixture showed the reaction intermediate (Rt=1.488 min, Rt=1.662 min) was consumed and a new peak (Rt=1.555 min was observed. The mixture was cooled to 25° C., ethyl acetate (10.0 L) was poured into the reaction mixture and stirred at 25° C. for 1 h. The mixture was poured into water (60.0 L) and filtered through celatom. The filtrate was extracted with EtOAc (30.0 L*2). The combined organic layers were washed with brine (30.0 L*2), dried over $Na_2SO_4$ and filtered. The filtrate was concentrated to give a crude residue. The residue was triturated by EtOAc:Petroleum ether=1:4 (1.00 L) at 25° C. for 1 h. 13 batches were prepared in parallel to give compound 13 (5.5 kg, 90% purity) as a gray solid which was confirmed by $^1H$ NMR. $^1H$ NMR: 400 MHz, DMSO-$d_6$ 14.30 (s, 1H), 8.66 (s, 1H), 8.49 (s, 1H).

Step 10. Preparation of Compound 14

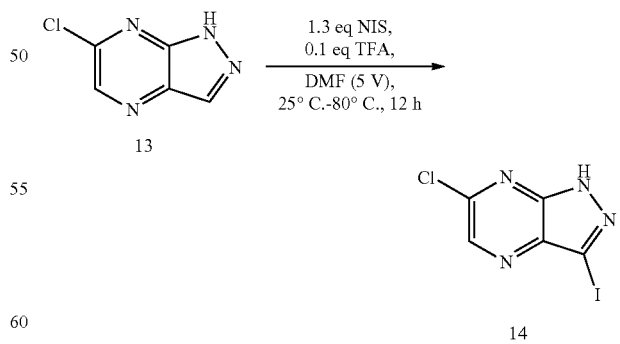

This procedure was performed in two batches. To a solution of compound 13 (2.50 kg, 14.1 mol, 1.00 eq) in DMF (12.5 L) was added NIS (4.12 kg, 18.3 mol, 1.30 eq) and TFA (160 g, 1.41 mol, 104 mL, 0.10 eq) at 25° C. The mixture was heated to 80° C. and stirred at 80° C. for 14 h.

TLC analysis (Petroleum ether:Ethyl acetate=3:1) showed compound 13 (R$_f$=0.3) was consumed and a new spot (R$_f$=0.4) was observed. HPLC analysis also showed compound 13 (Rt=1.487 min) was consumed and a new peak (Rt=2.080 min) was observed. The reaction mixture was poured into 5% Na$_2$SO$_3$ ice water (10.0 L), stirred at 0° C. to 5° C. for 1 h, then diluted with water (30.0 L), filtered, and the filter cake washed with water (5.00 L) and dried to give a crude product. The crude product was triturated with H$_2$O:ACN=2:1 (15.0 L). 2 batches were carried in parallel to give compound 14 (6.2 kg, 100% purity) as a gray solid which was confirmed by $^1$H NMR and LCMS. $^1$H NMR: 400 MHz, DMSO-d$_6$ 14.66 (s, 1H), 8.66 (s, 1H).

Step 11. Preparation of Compound 15

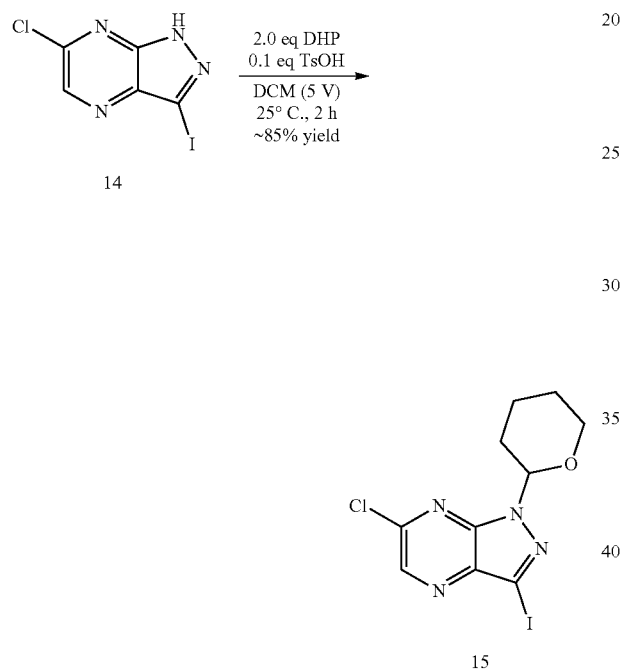

To a solution of compound 14 (6.38 kg, 22.8 mol, 1.00 eq) in DCM (30.0 L) was added TsOH·H$_2$O (433 g, 2.27 mol, 0.10 eq) at 0° C., then DHP (3.83 kg, 45.5 mol, 4.16 L, 2.00 eq) was added dropwise to the mixture at 0° C. The mixture was stirred at 25° C. for 2 h. TLC analysis (Petroleum ether:Ethyl acetate=3:1) showed compound 14 (R$_f$=0.6) was consumed and a new spot (R$_f$=0.7) was observed. HPLC analysis also showed compound 14 (Rt=2.059 min) was consumed and a new peak (Rt=2.927 min) was observed. The reaction mixture was poured into saturated aqueous NaHCO$_3$ (30.0 L), and the organic layer was washed with brine (30.0 L), dried over Na$_2$SO$_4$, filtered and concentrated. The residue was triturated by MTBE (10.0 L), the mixture was stirred at 25° C. for 2 h, filtered, the filter cake was washed with MTBE (3.0 L) and dried to afford compound 15 (5.1 kg, 97.9% purity) as a gray solid which was confirmed by $^1$H NMR and LCMS. $^1$H NMR: 400 MHz, CDCl$_3$ 8.56 (s, 1H), 5.98 (dd, J=10.5, 2.5 Hz, 1H), 4.27-4.10 (m, 1H), 3.83-3.65 (m, 1H), 2.70-2.64 (m, 1H), 2.19-2.18 (m, 1H), 2.01-1.97 (m, 1H), 1.81-1.78 (m, 2H), 1.66-1.63 (m, 1H).

Step 12. Preparation of Compound 17

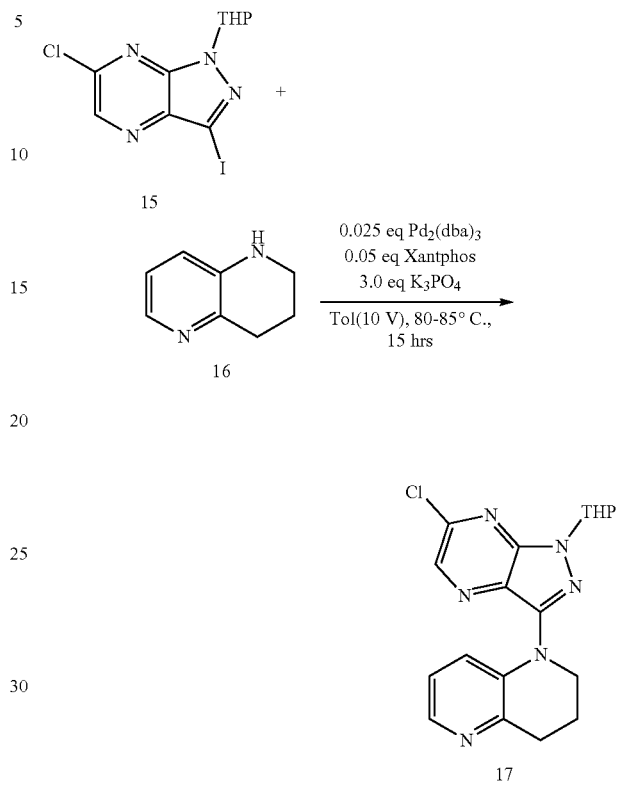

To a 50 L jacketed reactor under nitrogen was added compound 15 (2000 g, 5.206 mol), compound 16 (700 g, 5.206 mol), K$_3$PO$_4$ (3320 g, 15.64 mol), Xantphos (151 g, 262.41 mmol), Pd$_2$(dba)$_3$ (119 g, 130.16 mmol) and toluene (20 L). The reaction mixture was stirred at 80° C. to 85° C. for 15 h until the reaction was complete. The reaction mixture was cooled to 20° C. to 30° C. and washed twice with H$_2$O (10 kg). The organic layer was passed through 2 kg silicathiol and 8 kg silica gel column, eluent with EA. Concentration and crystallization with THF:heptanes=1:3 afforded a wet cake. The wet cake was dried at 45° C. to 50° C. under vacuum for 20-24 h to afford 1.25 kg of compound 17.

Step 13. Preparation of Compound 18

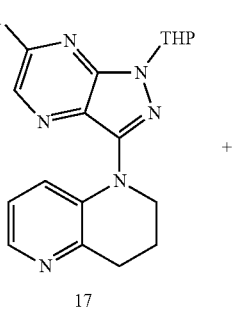

-continued

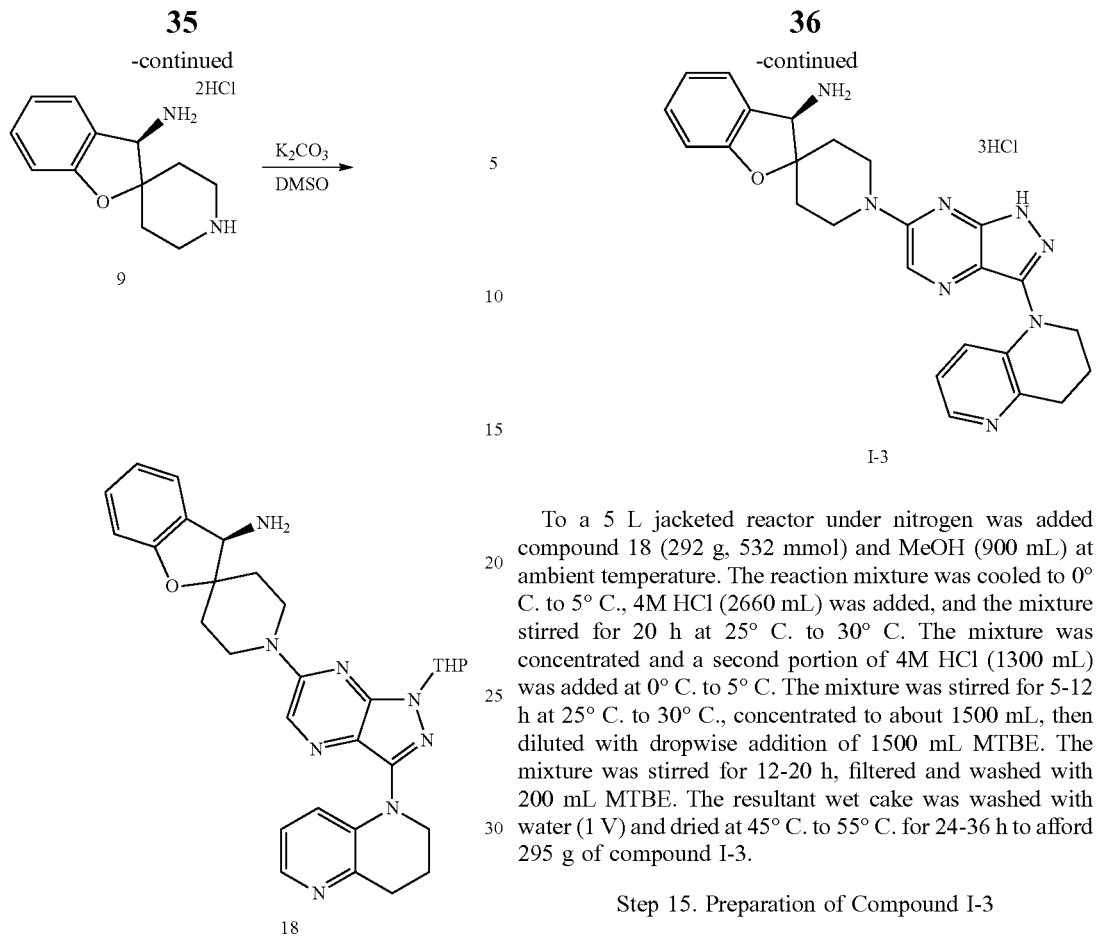

To a 5 L jacketed reactor under nitrogen was added compound 17 (217 g, 586 mmol), compound 9 (192 g, 704 mmol), K₂CO₃ 324 g, 2.35 mol), DMSO (900 mL). The reaction mixture was stirred at 60° C. to 65° C. for 3-4 h until the reaction was complete. The reaction mixture was cooled to 20° C. to 30° C. DMSO (900 mL) was added, then H₂O (1800 g) was drop wise. The reaction mixture was stirred at 20° C. to 30° C. for 2-5 hours. The resultant slurry was filtered, and the wet cake washed with H₂O (1200 g). The cake was dried at 45° C. to 50° C. under vacuum for 36-40 h to afford compound 18.

Step 14. Preparation of 1-3

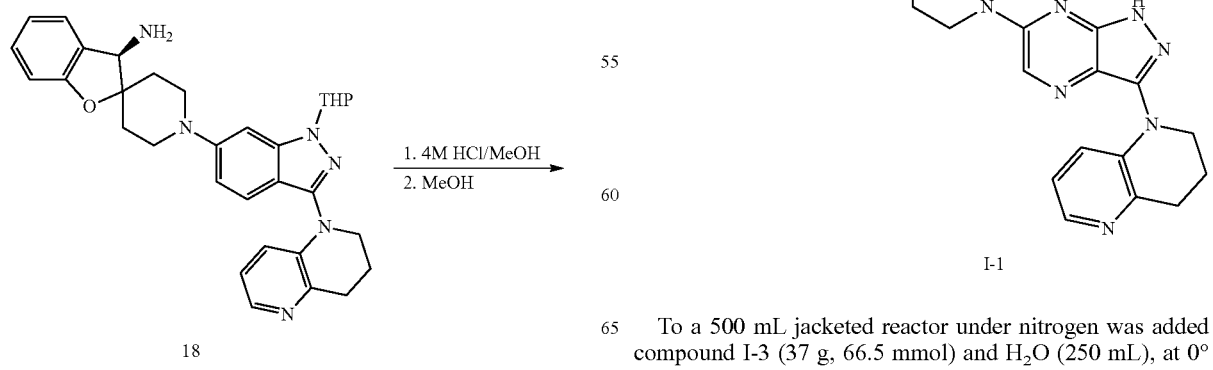

To a 5 L jacketed reactor under nitrogen was added compound 18 (292 g, 532 mmol) and MeOH (900 mL) at ambient temperature. The reaction mixture was cooled to 0° C. to 5° C., 4M HCl (2660 mL) was added, and the mixture stirred for 20 h at 25° C. to 30° C. The mixture was concentrated and a second portion of 4M HCl (1300 mL) was added at 0° C. to 5° C. The mixture was stirred for 5-12 h at 25° C. to 30° C., concentrated to about 1500 mL, then diluted with dropwise addition of 1500 mL MTBE. The mixture was stirred for 12-20 h, filtered and washed with 200 mL MTBE. The resultant wet cake was washed with water (1 V) and dried at 45° C. to 55° C. for 24-36 h to afford 295 g of compound I-3.

Step 15. Preparation of Compound I-3

To a 500 mL jacketed reactor under nitrogen was added compound I-3 (37 g, 66.5 mmol) and H₂O (250 mL), at 0° C. to 5° C. The reaction mixture was stirred at 0° C. to 5°

C. for 0.5-1 h. The mixture was diluted with 220 mL 1M NaOH solution and stirred for 1-2 h at 0° C. to 5° C. 2-MeTHF (800 mL) was then added and the mixture stirred for 0.5-1 h. The organic layer was separated and washed with water (500 mL*2). The organic layer was concentrated via distillation below 45° C. then diluted with MeOH. 0.35 g of compound I-1 seed crystal was added, and the mixture stirred for 2-5 h at 25° C. to 30° C. 500 mL of water was added dropwise, and the mixture stirred stir for 5-12 h at 25° C. to 30° C. The solid was collected by filtration, washed with water and the wet cake dried under vacuum at 60° C. to 70° C. for 48-60 h to afford compound I-1.

Example 2—Polymorph Analysis of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine (Compound I-1)

Polymorph analysis of the compound I-1 (also referred to as (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine) was performed in 12 different solvents by a temperature cycling method. If no suspended solids were observed when the system was cooled to 25° C., then the solution was evaporated. Details of operation procedures were listed as below:

About 50 mg of compound I-1 were weighted into 2.0-mL glass vials and then 0.5-1.0 mL selected solvents were added. Then vials were placed were stirred at a rate of 600 r/min and then heated or cooled according to below temperature programs: heating to 50° C. over 1 hr and then holding at 50° C. for 1 hr; then cooling to 5° C. over 3 hrs and then holding at 5° C. for 1 hr. This temperature program was re-cycled for 4 times for a total of about 24 hrs. Then the system was stirred at 25° C. for another 1 hr. For the samples which resulted in suspensions, the systems were centrifuged at 8000 r/min for 5 mins. Mother liquids were removed, and wet solids were dried in the vacuum oven at 50° C. for 3 hrs. Obtained dry solids were then characterized by XRPD. If a new XRPD pattern was identified, the dry solids with new XRPD patterns were also characterized by PLM, DSC and TGA. For the clear solutions, the vials were then placed in the fume hood at 25° C. to evaporate residual solvents. After 4 days of evaporation, some solids precipitated out. The solids were then dried in the vacuum oven at 30° C. for 21.5 hrs. Obtained dry solids were then characterized by XRPD. If a new XRPD pattern was identified, the dry solids with new XRPD patterns were also characterized by PLM, DSC and TGA.

A summary of the solvents examined can be found in Table 1:

TABLE 1

| | | Appearance | | |
|---|---|---|---|---|
| # | Solvents | Temperature cycling | Evaporation | XRPD Results |
| 1 | MeOH | Clear Solution | Yellow Solids | Amorphous |
| 2 | EtOH | Suspension | N/A | Pattern A |
| 3 | ACN | Suspension | N/A | Pattern A |
| 4 | Acetone | Clear Solution | Oil | N/A |
| 5 | MEK | Suspension | N/A | Pattern A |
| 6 | EtOAc | Suspension | N/A | Pattern A |
| 7 | IPAc | Suspension | N/A | Pattern A |
| 8 | THF | Suspension | N/A | Pattern A |
| 9 | MtBE | Suspension | N/A | Pattern A |
| 10 | Toluene | Suspension | N/A | Pattern A |

TABLE 1-continued

| | | Appearance | | |
|---|---|---|---|---|
| # | Solvents | Temperature cycling | Evaporation | XRPD Results |
| 11 | 1,4 dioxane | Suspension | N/A | Pattern A |
| 12 | EtOH/water (9v/1v) | Suspension | N/A | Pattern A |

Initial material of compound I-1 was in crystalline form, but the crystallinity was very low. After polymorph screening experiments, obtained solids all showed the same XRPD pattern, and this pattern was named as Pattern A. Pattern A of compound I-1 was then characterized by PLM, DSC, TGA and $^1$H-NMR. DSC scan of Pattern A in FIG. 1B showed a single endothermic peak at the onset of 196.2° C. (enthalpy: 75.0 J/g). TGA scan (FIG. 1B) showed a weight loss of 1.08% from 30° C. to 200° C. In summary, pattern A is a pure crystalline form of compound I-1.

The XRPD of Pattern A of compound I-1 is shown in FIG. 1A. The TGA and DSC analysis of Pattern A of compound I-1 is shown in FIG. 1B.

Table 2 below sets out the X-Ray diffraction peaks observed for Pattern A of compound I-1, wherein each value is in degrees 2θ:

TABLE 2

| Angle (2θ)° | Intensity % |
|---|---|
| 6.7 | 34.5 |
| 9.7 | 2.9 |
| 10.3 | 8.4 |
| 11.2 | 15.6 |
| 12.2 | 18.4 |
| 12.8 | 30.3 |
| 13.4 | 24.9 |
| 15.2 | 3.4 |
| 15.5 | 3.1 |
| 16.0 | 45.6 |
| 16.6 | 9.3 |
| 17.2 | 10.9 |
| 19.3 | 14.4 |
| 19.9 | 74.8 |
| 20.3 | 3.0 |
| 20.7 | 28.9 |
| 21.1 | 8.3 |
| 21.4 | 4.4 |
| 21.7 | 16.4 |
| 22.5 | 14.4 |
| 23.0 | 3.1 |
| 24.0 | 7.2 |
| 24.6 | 100.0 |
| 25.4 | 4.4 |
| 26.0 | 6.0 |
| 26.7 | 19.7 |
| 26.8 | 6.9 |
| 27.4 | 4.6 |
| 28.4 | 3.8 |
| 29.4 | 6.3 |
| 30.2 | 12.8 |
| 30.7 | 6.8 |
| 31.1 | 5.6 |
| 31.3 | 3.6 |
| 32.0 | 3.3 |
| 32.2 | 3.3 |
| 32.8 | 2.7 |
| 33.3 | 2.9 |
| 34.1 | 4.5 |
| 35.4 | 3.3 |

Example 3—Preparation of Salt Forms of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine To identify salts for compound I-1, the salt experiments were performed with 16 different counter-ions (acids) in 3 selected solvents (ACN, acetone and EtOAc). If no solids were obtained when the system was cooled to 25° C., the solution was subject to an evaporation method. Details of operation procedures were listed as below:

For the salt formation with solid acids, about 50 mg of compound I-1 and 1.1 e.q. of the respective solid acids were weighted into 2.0-mL glass vials. Then 1.0 mL of the selected solvent was added into the vials with API and acid.

For the salt formation with liquid acids, about 50 mg starting of compound I-1 was weighed into 2.0-mL glass vials and 760 μL of the selected solvent was added. Then 1.1 e.q. of the respective acid solution (242 μL, 0.5 mmol/mL) was added into the vials with API and solvent.

Separately, about 50 mg of compound I-1 was weighted into 2.0-mL glass vials and then 1.0 mL of the selected solvent was added as a control system.

Then all the vials were stirred at a speed of 600 r/min and then heated and cooled according to below temperature programs: heating to 50° C. in 1 hr and then holding at 50° C. for 1 hr; then cooling to 5° C. in 3 hrs and then holding at 5° C. for 1 hr. This temperature program was re-cycled for 4 times for a total of about 24 hrs. Then the system was stirred at 25° C. for another 40 hrs. For samples which resulted in suspensions, the systems were centrifuged at 8000 r/min for 5 mins, and then the mother liquids were removed. The wet solids were dried in the vacuum oven at 30° C. for 17-21.5 hrs. Obtained dry solids were then characterized by XRPD. If a new XRPD pattern was identified, the dry solids with new XRPD patterns were also characterized by PLM, DSC and TGA. For the clear solutions, the vials were then placed in the fume hood at 25° C. to evaporate residual solvents. After evaporation, if solids were generated, obtained solids were then characterized by XRPD. If a new XRPD pattern was identified, the dry solids with new XRPD patterns were also characterized by PLM, DSC and TGA.

The salt results are listed in Table 3.

In salt formation experiments, 5 new XRPD patterns were found with four different counter ions, including hydrobromic acid (Pattern S1-I), p-toluene sulfonic acid (Pattern S6-I), benzene sulfonic acid (Pattern S7-I and S7-II) and glutaric acid (Pattern S16-I). Most of obtained solids were amorphous or crystalline with low crystallinity. From the results, we could see that the salts with glutaric acid showed high crystallinity among all the systems.

TABLE 3

| # | Counter-ions | Solvents | | |
|---|---|---|---|---|
| | | A-ACN | B-Acetone | C-EtOAc |
| 1 | Hydrobromic acid | Amorphous | S1-I(LC) | Amorphous |
| 2 | Hydrochloric acid | Amorphous | Amorphous | Amorphous |
| 3 | Sulfuric acid | Amorphous | Amorphous* | Amorphous* |
| 4 | Methane Sulfonic acid | Amorphous | Amorphous* | Amorphous* |
| 5 | Phosphoric Acid | Pattern A (LC) | Amorphous | Pattern A (LC) |
| 6 | p-Toluene sulfonic acid | S6-I (LC) | S6-I (LC) | S6-I (LC) |
| 7 | Benzene sulfonic acid | S7-I (LC) | S7-I (LC) | S7-I (LC) |
| 8 | Oxalic acid | Amorphous + trace Pattern A | Amorphous | Amorphous |
| 9 | L-Aspartic acid | Pattern A + L-Aspartic acid | L-Aspartic acid | Pattern A + L-Aspartic acid |
| 10 | Maleic acid | Amorphous + trace Pattern A* | Amorphous* | Amorphous + Pattern A |
| 11 | Malonic acid | Amorphous | Amorphous | Oil |
| 12 | L-Tartaric acid | Pattern A (LC) | Amorphous | Pattern A (LC) |
| 13 | Fumaric acid | Pattern A | Amorphous | Amorphous |
| 14 | Citric acid | Pattern A | Amorphous | Amorphous + Citric acid |
| 15 | Succinic acid | Amorphous + trace Pattern A | Amorphous | Amorphous + Pattern A |
| 16 | Glutaric acid | S16-I | S16-I | S16-I |
| 17 | Control | Pattern A | N/A | Pattern A |

*The obtains solids were very inclined to absorb moisture in the air and then formed liquid in the XRPD analysis procedure.
Note:
1. Roman numbers mean the different XRPD patters of the salt.
"A" means the XRPD pattern of starting free base.
2. LC is an abbreviation for "low crystallinity"

Figure 2A:
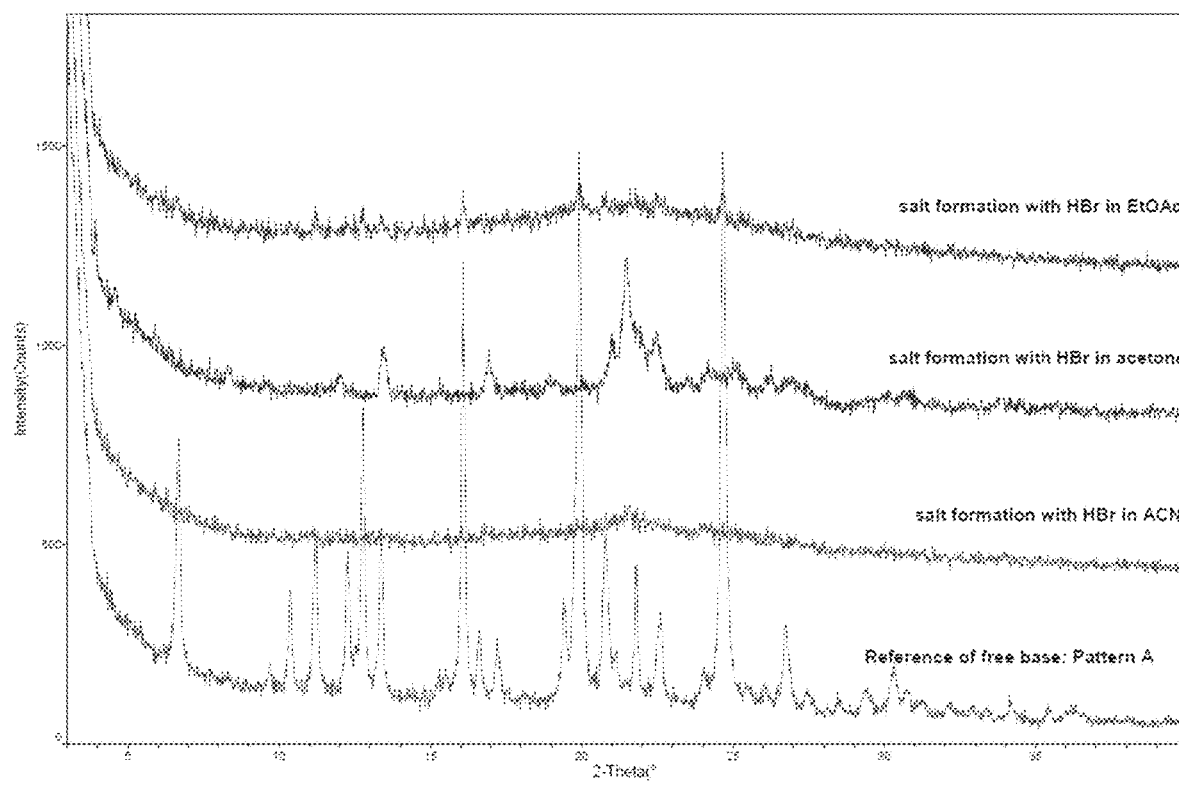
FIG. 2A depicts the characterization of X-ray diffraction pattern of Compound I-2 compared to the X-ray diffraction pattern of Pattern A of Compound I-1.
Figure 2B:
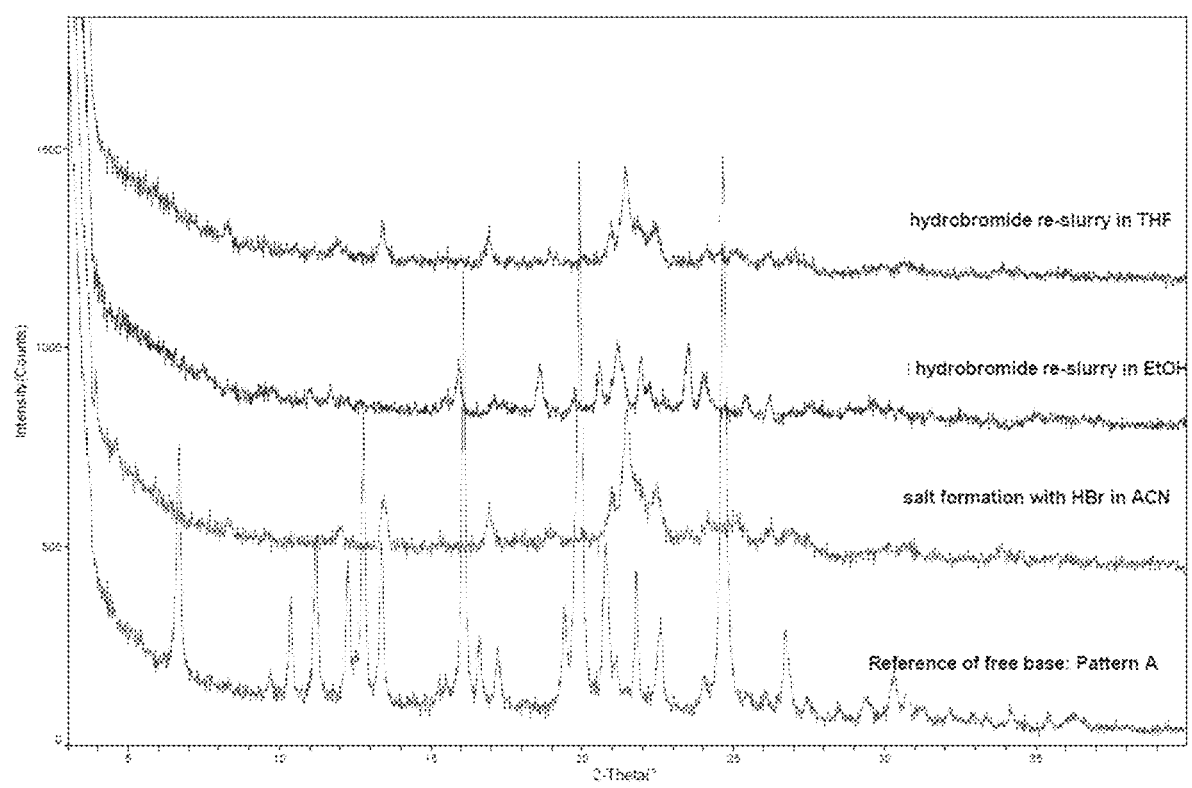
FIG. 2B depicts the characterization of X-ray diffraction pattern of Compound I-2 after re-slurry experiments compared to the X-ray diffraction pattern of Pattern A of Compound I-1.
Figure 2C:
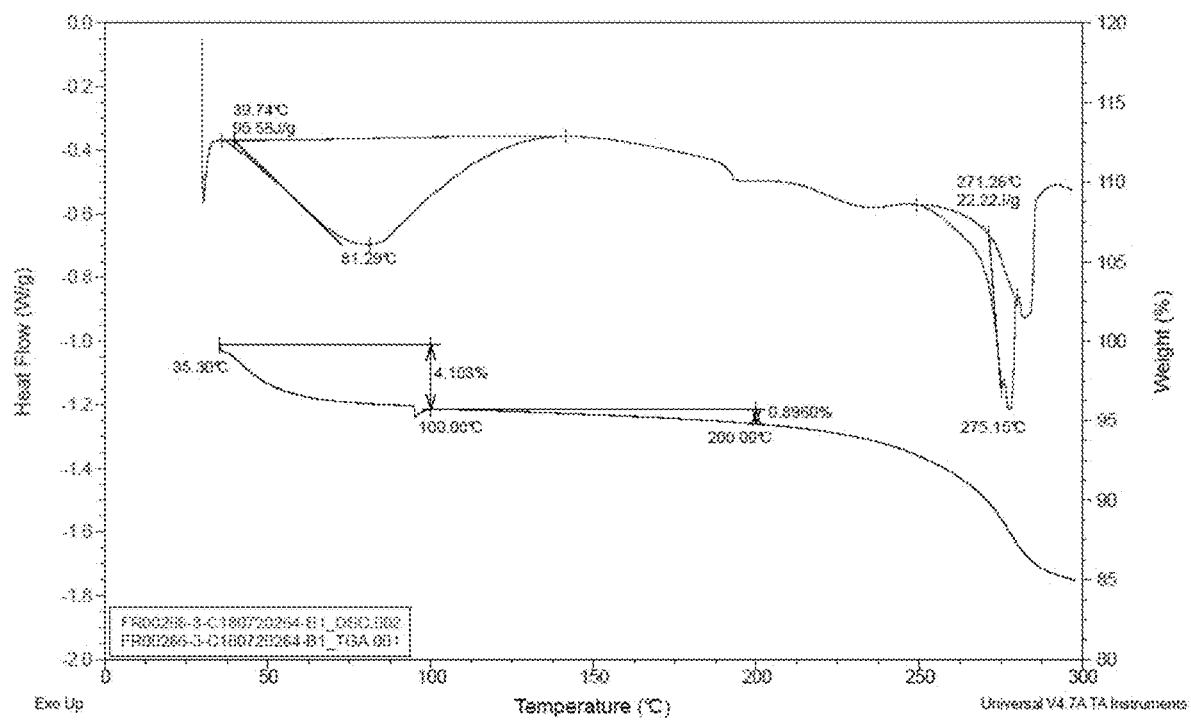
FIG. 2C depicts the characterization of Pattern S1-I of Compound I-2 by differential scanning calorimetry (DSC) (green) and thermogravimetric analysis (TGA) (blue).

The XRPD of Pattern S1-I of compound I-2 is shown in FIG. 2A. The TGA and DSC analysis of Pattern S1-I of compound I-2 is shown in FIG. 2C.

Figure 7A:
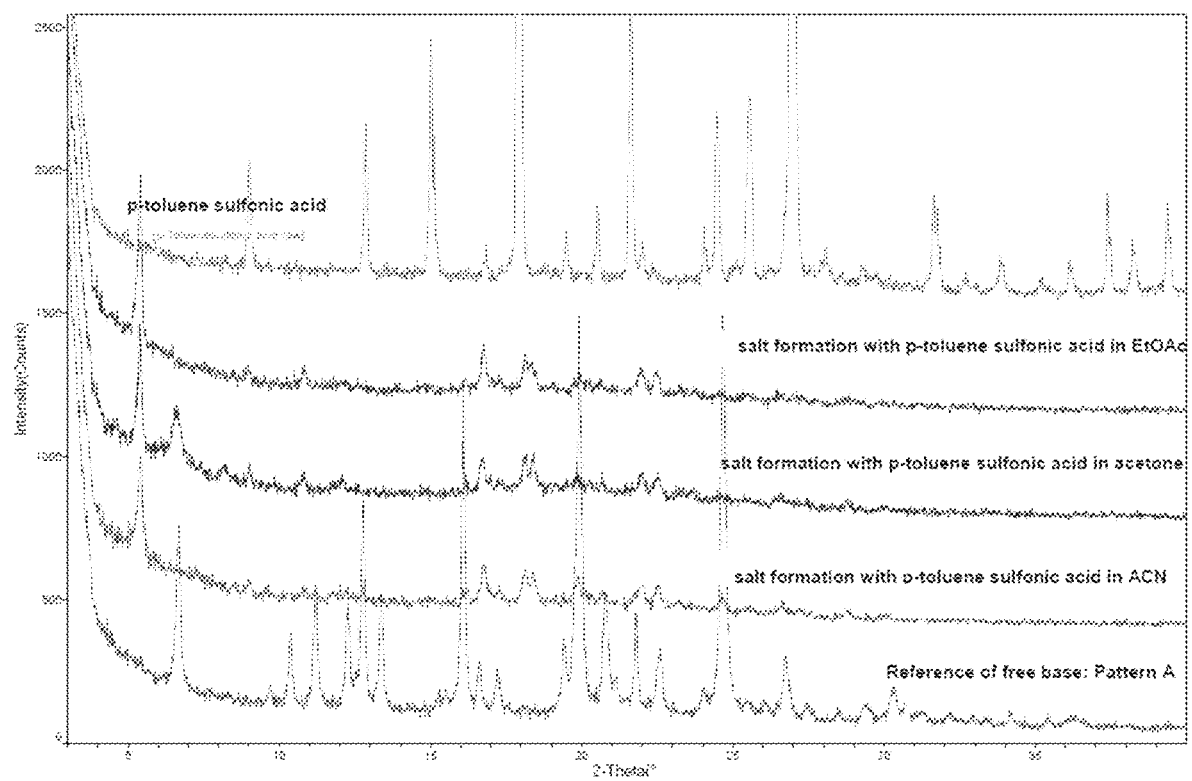
FIG. 7A depicts the characterization of X-ray diffraction pattern of Compound I-7 compared to the X-ray diffraction pattern of Pattern A of Compound I-1.
Figure 7B:
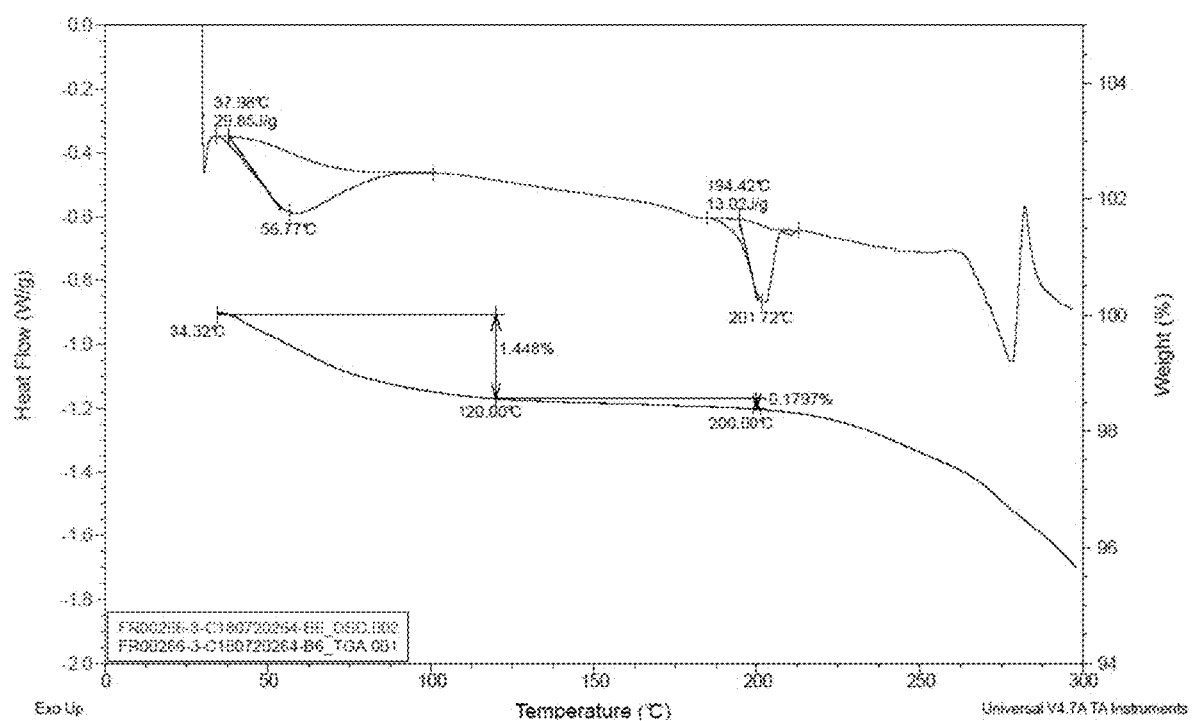
FIG. 7B depicts the characterization of Pattern S6-I Compound I-7 by differential scanning calorimetry (DSC) (green) and thermogravimetric analysis (TGA) (blue).

The XRPD of Pattern S6-I of compound I-7 is shown in FIG. 7A. The TGA and DSC analysis of Pattern S6-I of compound I-7 is shown in FIG. 7B.

Figure 8A:
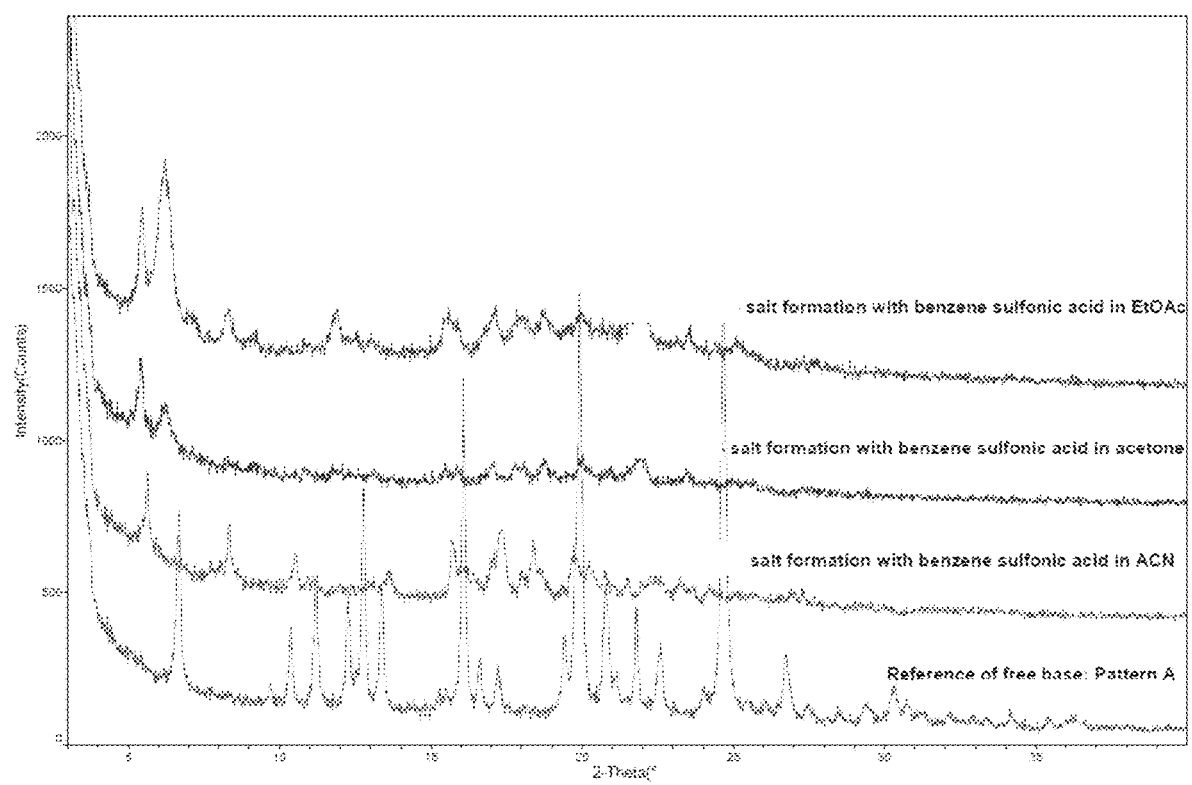
FIG. 8A depicts the characterization of X-ray diffraction pattern of Compound I-8 compared to the X-ray diffraction pattern of Pattern A of Compound I-1.
Figure 8B:
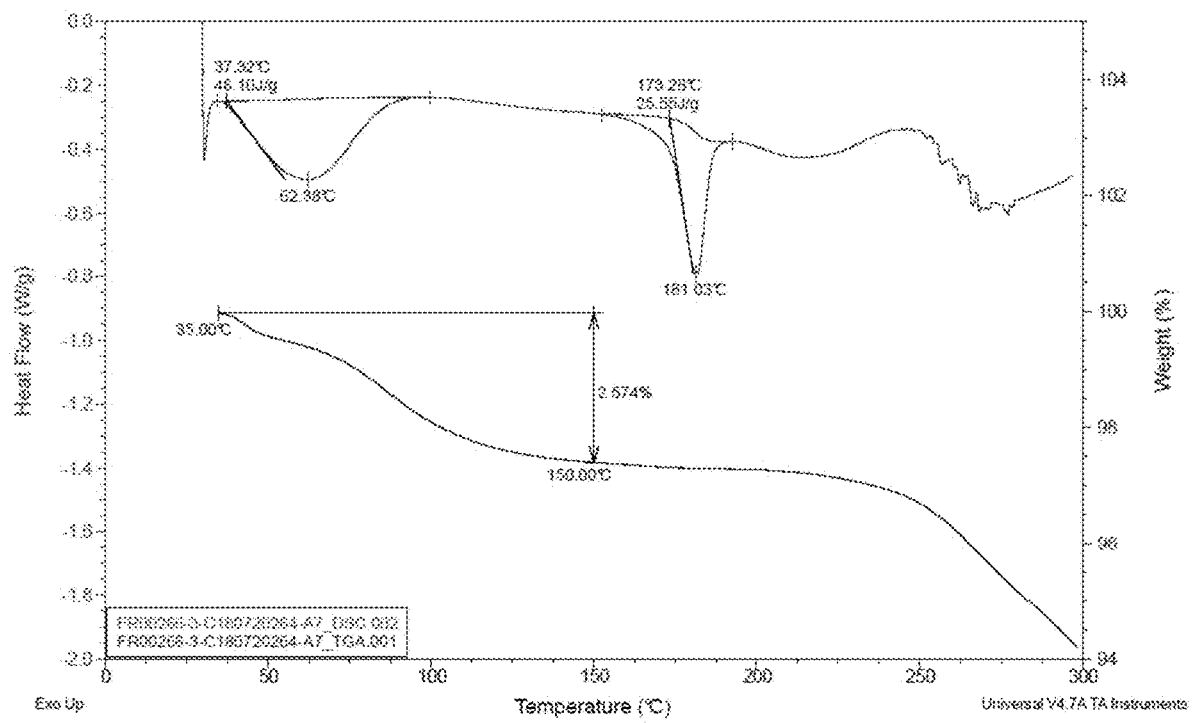
FIG. 8B depicts the characterization of Pattern S7-I of Compound I-8 by differential scanning calorimetry (DSC) (green) and thermogravimetric analysis (TGA) (blue).
Figure 8C:
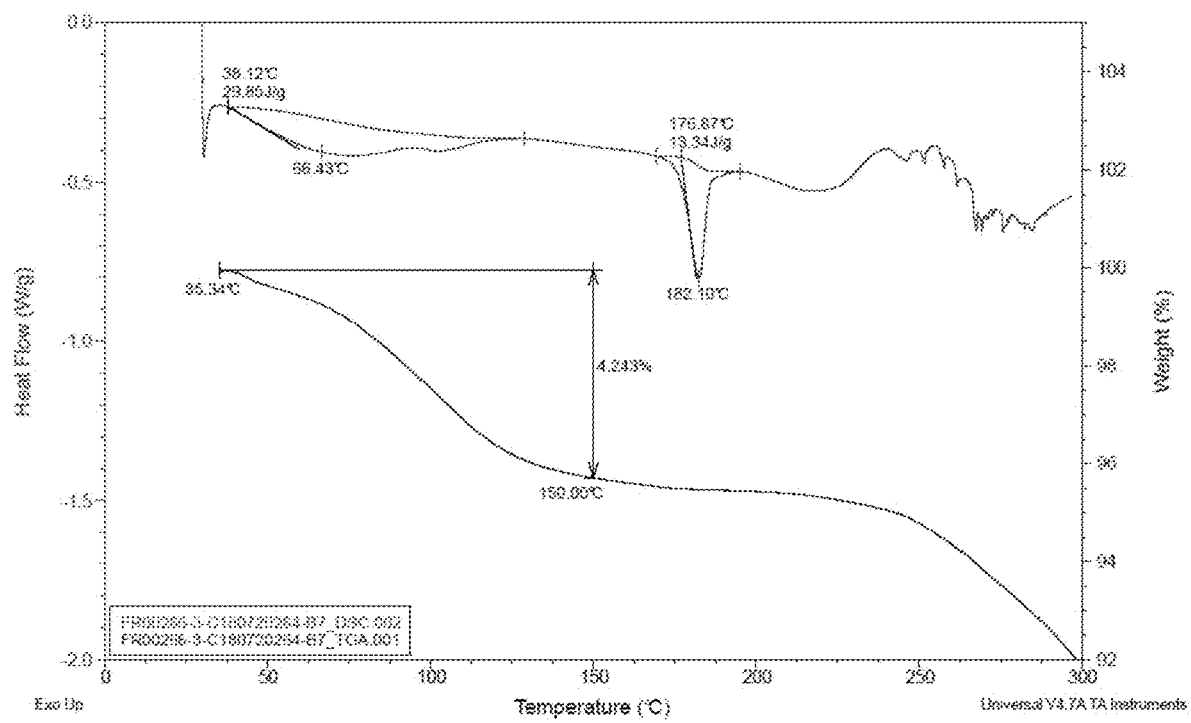
FIG. 8C depicts the characterization of Pattern S7-II of Compound I-8 by differential scanning calorimetry (DSC) (green) and thermogravimetric analysis (TGA) (blue).

The XRPD of Patterns S7-I and S7-II of compound I-8 is shown in FIG. 8A. The TGA and DSC analysis of Pattern S7-I of compound I-8 is shown in FIG. 8B. The TGA and DSC analysis of Pattern S7-II of compound I-8 is shown in FIG. 8C.

Figure 17A:
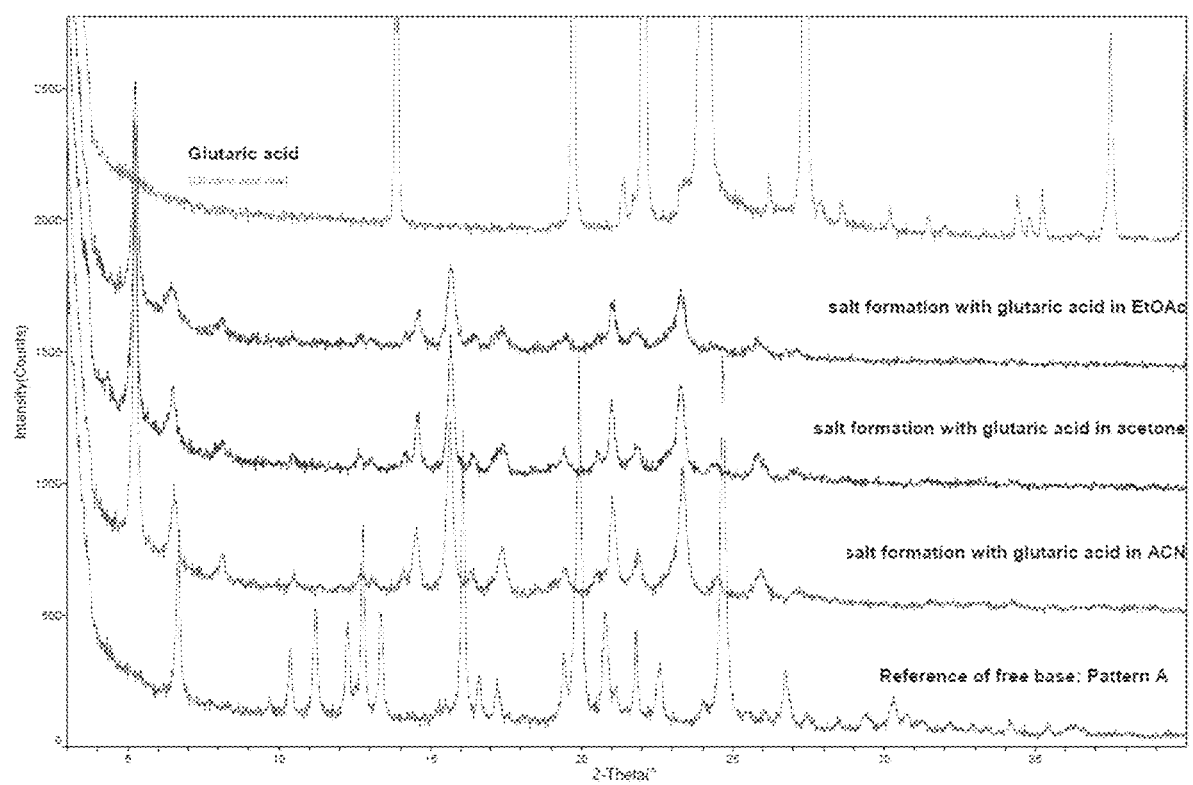
FIG. 17A depicts the characterization of X-ray diffraction pattern of Compound I-17 compared to the X-ray diffraction pattern of Pattern A of Compound I-1.
Figure 17B:
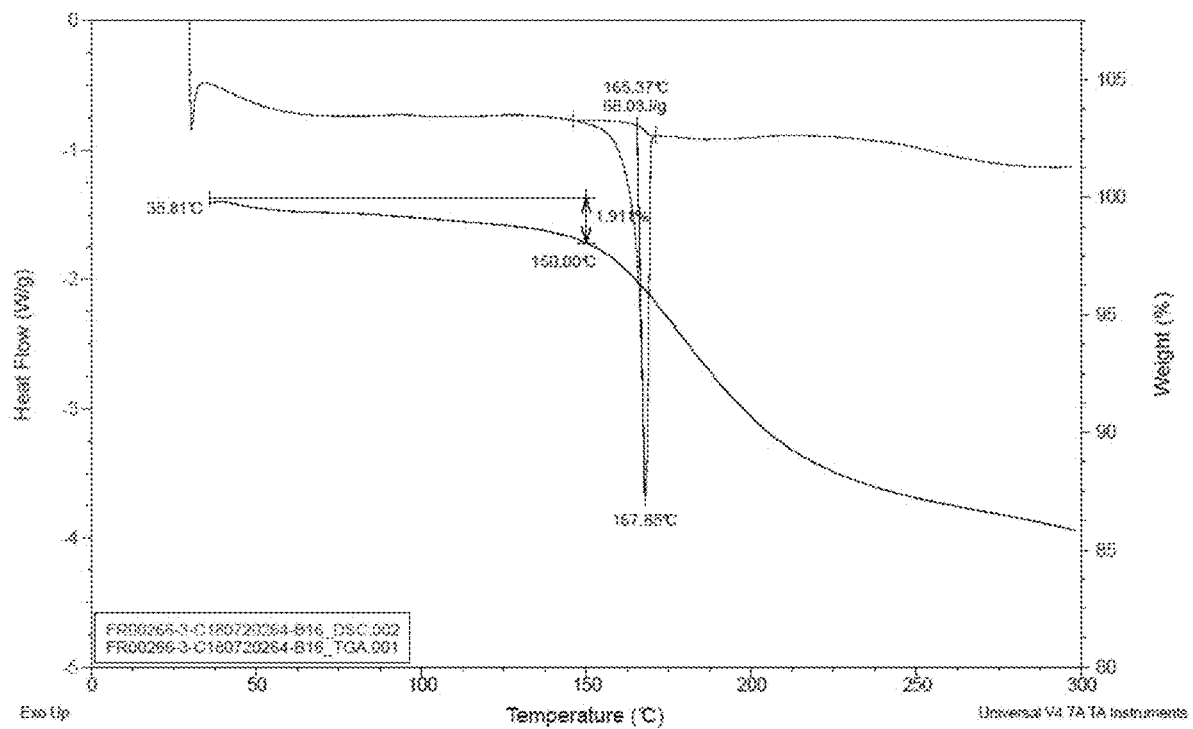
FIG. 17B depicts the characterization of Pattern A of Compound I-17 by differential scanning calorimetry (DSC) (green) and thermogravimetric analysis (TGA) (blue).

The XRPD of Pattern S16-I of compound I-17 is shown in FIG. 17A. The TGA and DSC analysis of Pattern S16-I of compound I-17 is shown in FIG. 17B.

Example 4—Auxiliary Preparation of Salt Forms of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine Amorphous solids obtained from Example 3 were re-slurried in more solvents (EtOH, THF or 95% IPA in water)

to try to find more crystalline salts. Details of operation procedures were listed as below:

The amorphous solids were re-slurried in 500 L selected solvents (EtOH, THF or 95% IPA in water) in 2.0-mL vials. All the slurries were stirred at a speed of 700 r/min and then heated and cooled according to below temperature programs: heating to 50° C. in 1 hr and then holding at 50° C. for 1 hr; then cooling to 5° C. in 3 hrs and then holding at 5° C. for 1 hr. This temperature program was re-cycled for 8 times for a total time of about 48 hrs. For samples that resulted in suspensions, the systems were centrifuged at 8000 r/min for 5 mins, mother liquids were removed, and wet solids were dried in the vacuum oven at 60° C. for 4 hrs. Obtained dry solids were then characterized by XRPD. If a new XRPD pattern was identified, the dry solids with new XRPD patterns were also characterized by PLM, DSC and TGA. For the clear solutions, the vials were then placed in the fume hood at 25° C. to evaporate residual solvents. After evaporation, if solids were generated, obtained solids were then characterized by XRPD. If a new XRPD pattern was identified, the dry solids with new XRPD patterns were also characterized by PLM, DSC and TGA.

The salt results are listed in Table 4.

TABLE 4

| # | Counter-ions | Solvents | | |
|---|---|---|---|---|
| | | D-EtOH | E-THF | F-95% IPA |
| 1 | Hydrobromic acid | S1-II (LC) | S1-I (LC) | N/A |
| 2 | Hydrochloric acid | Oil | Amorphous | Oil |
| 3 | Sulfuric acid | Amorphous | Amorphous | S3-I (LC) |
| 4 | Methane Sulfonic acid | Oil | Amorphous | Oil |
| 5 | Phosphoric Acid | Amorphous | N/A | N/A |
| 6 | p-Toluene sulfonic acid | N/A | N/A | N/A |
| 7 | Benzene sulfonic acid | N/A | N/A | N/A |
| 8 | Oxalic acid | S8-I (LC) | Amorphous | S8-II (LC) |
| 9 | L-Aspartic acid | N/A | N/A | N/A |
| 10 | Maleic acid | Oil | Amorphous | N/A |
| 11 | Malonic acid | S11-I | S11-I (LC) | N/A |
| 12 | L-Tartaric acid | Amorphous | N/A | N/A |
| 13 | Fumaric acid | Amorphous | Amorphous | N/A |
| 14 | Citric acid | Amorphous | N/A | N/A |
| 15 | Succinic acid | Amorphous | Oil | N/A |
| 16 | Glutaric Acid | N/A | N/A | N/A |

Note:
1. Roman numbers mean the different XRPD patters of the salt.
2. LC is an abbreviation for "low crystallinity."
3. For clear solutions, an evaporation crystallization procedure was carried out.

Figure 12B:
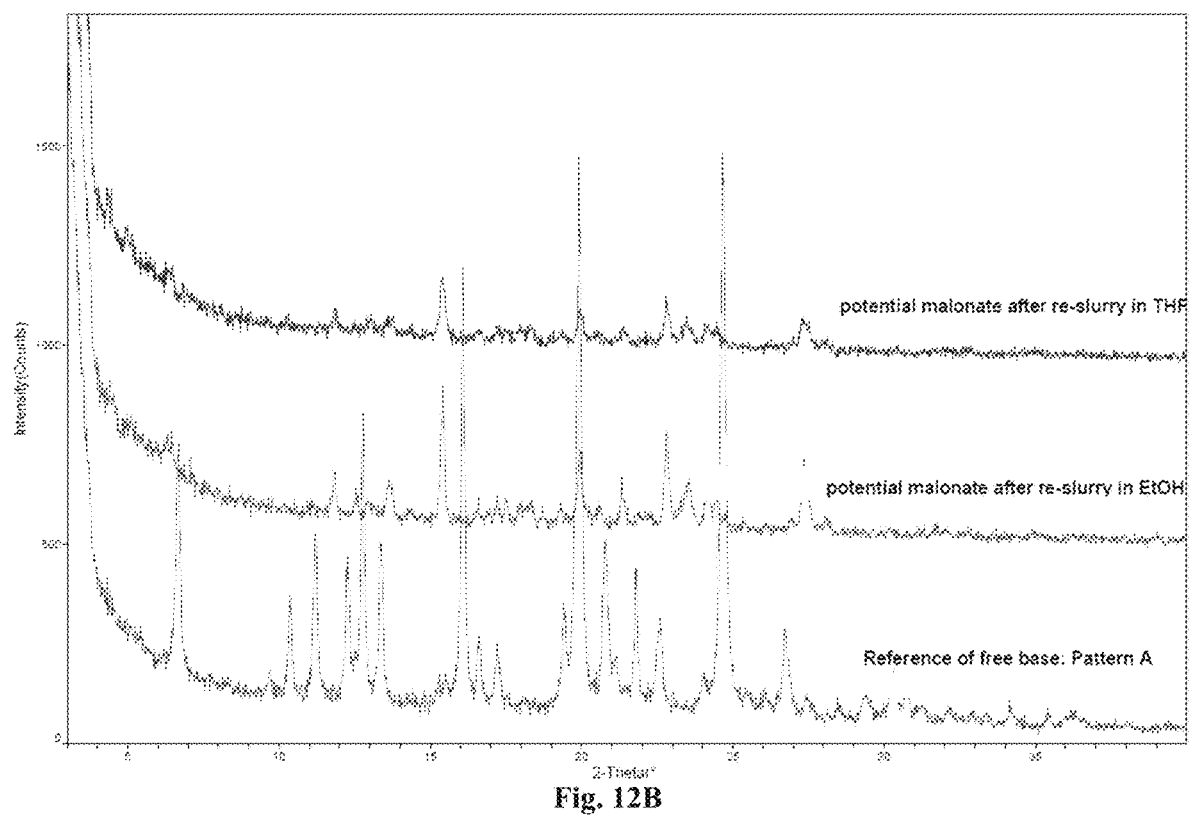
FIG. 12B depicts the characterization of X-ray diffraction pattern of Compound I-12 after re-slurry experiments compared to the X-ray diffraction pattern of Pattern A of Compound I-1.
Figure 12C:
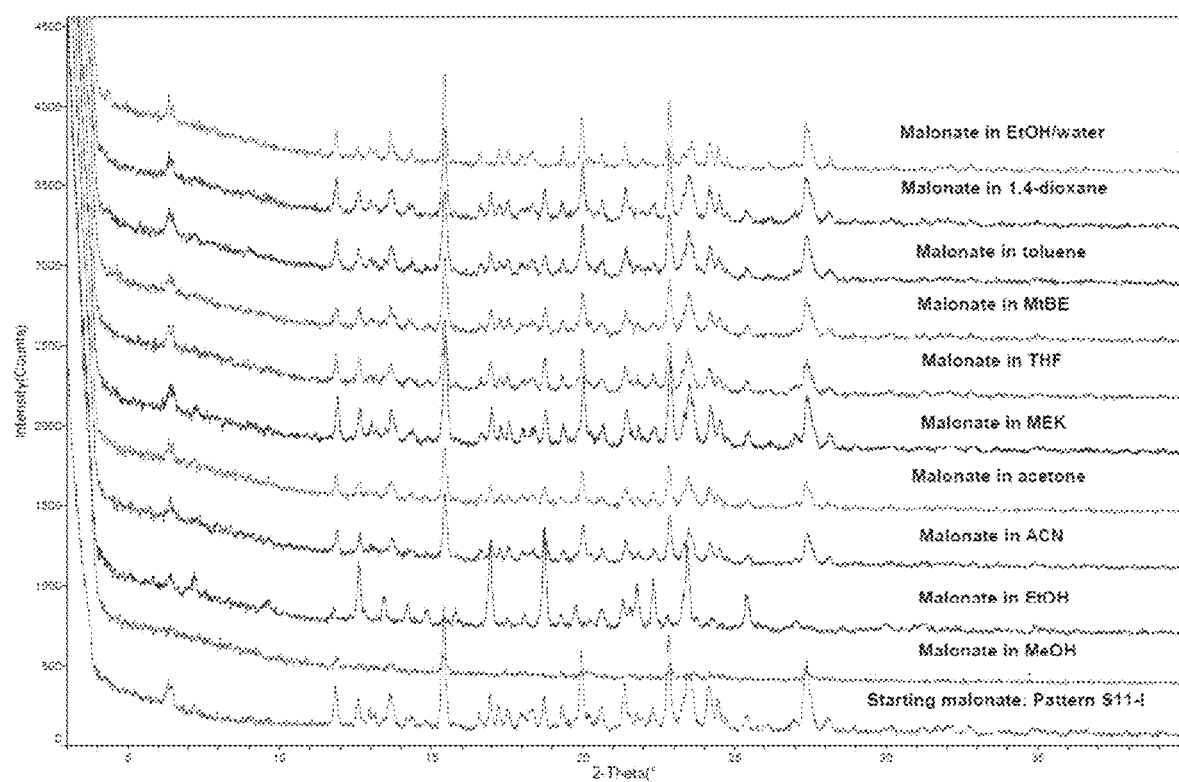
FIG. 12C depicts the characterization of X-ray diffraction pattern of Compound I-12 after polymorph screen experiments.
Figure 12D:
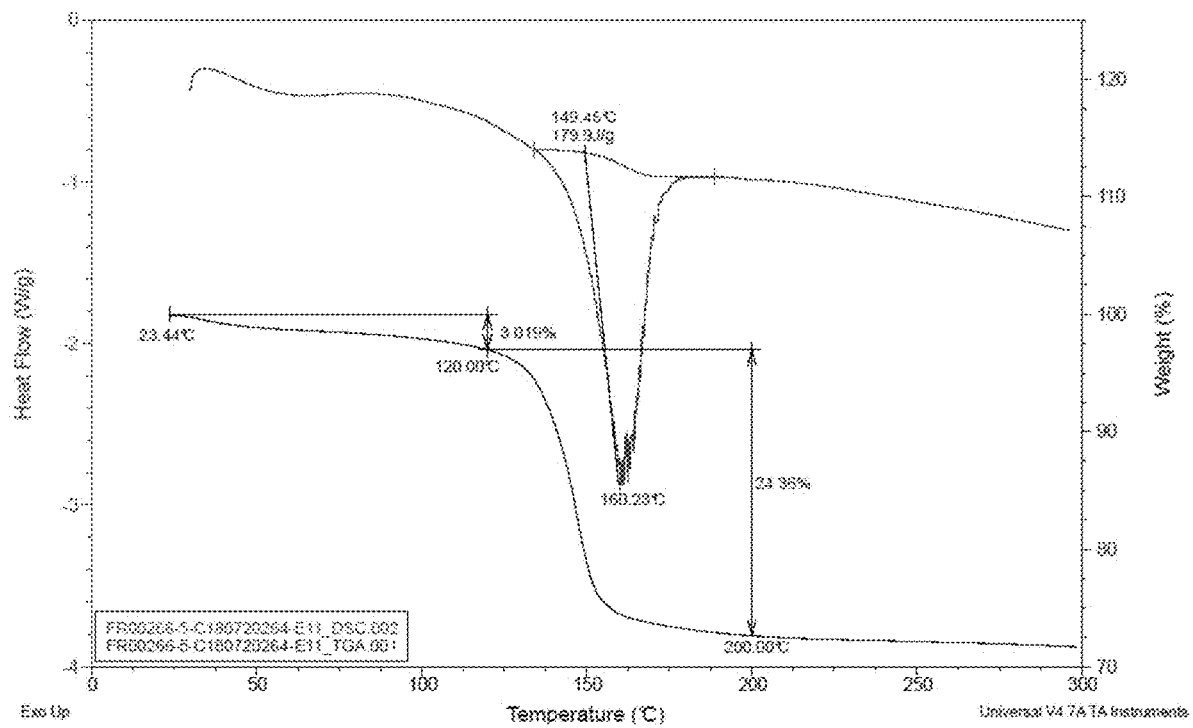
FIG. 12D depicts the characterization of Pattern A of Compound I-12 by differential scanning calorimetry (DSC) (green) and thermogravimetric analysis (TGA) (blue).

In the re-slurry experiments, t 5 additional, new XRPD patterns were found with four different counter-ions, including hydrobromic acid (Pattern S1-II) (see FIG. 2B), sulfonic acid (Pattern S3-I) (see FIG. 4B), oxalic acid (Pattern S8-I and S8-II) (see FIG. 9B) and malonic acid (Pattern S11-I) (see FIG. 12B). Only pattern S11-I shows relatively high crystallinity, for others, the crystallinity is low.

Considering the crystallinity of prepared p-toluene sulfate and glutarate were somewhat low, reslurry experiment was performed in ethanol and 95% IPA with 5% water solvents.

About 30 mg p-toluene sulfate and glutarate were suspended into 0.5 mL EtOH or 95% IPA with 5% water, respectively. The suspensions were stirred at 25° C. for 18 hrs with the speed of 500 r/min. Then few solids were taken out and characterized by XRPD after dried in the vacuum oven at 60° C. for 5 hrs.

Figure 7C:
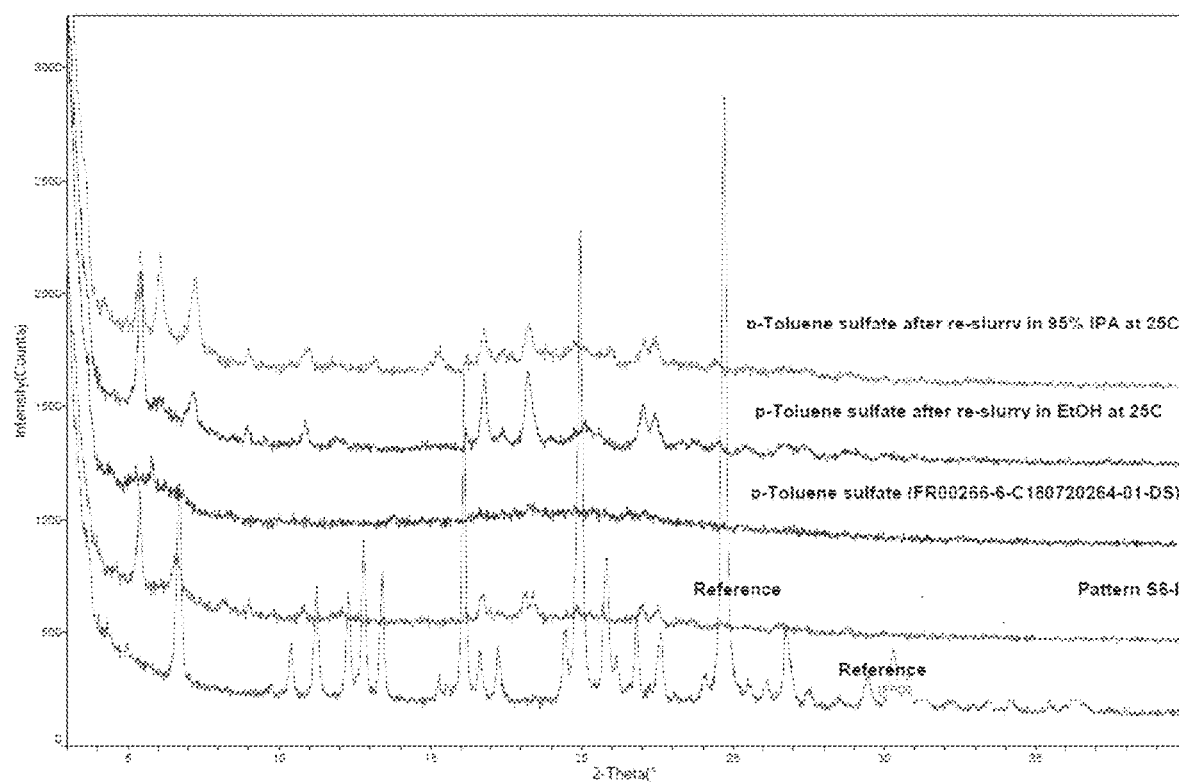
FIG. 7C depicts the characterization of X-ray diffraction pattern of Compound I-7 after re-slurry experiments compared to the X-ray diffraction pattern of Pattern A of Compound I-1.
Figure 17C:
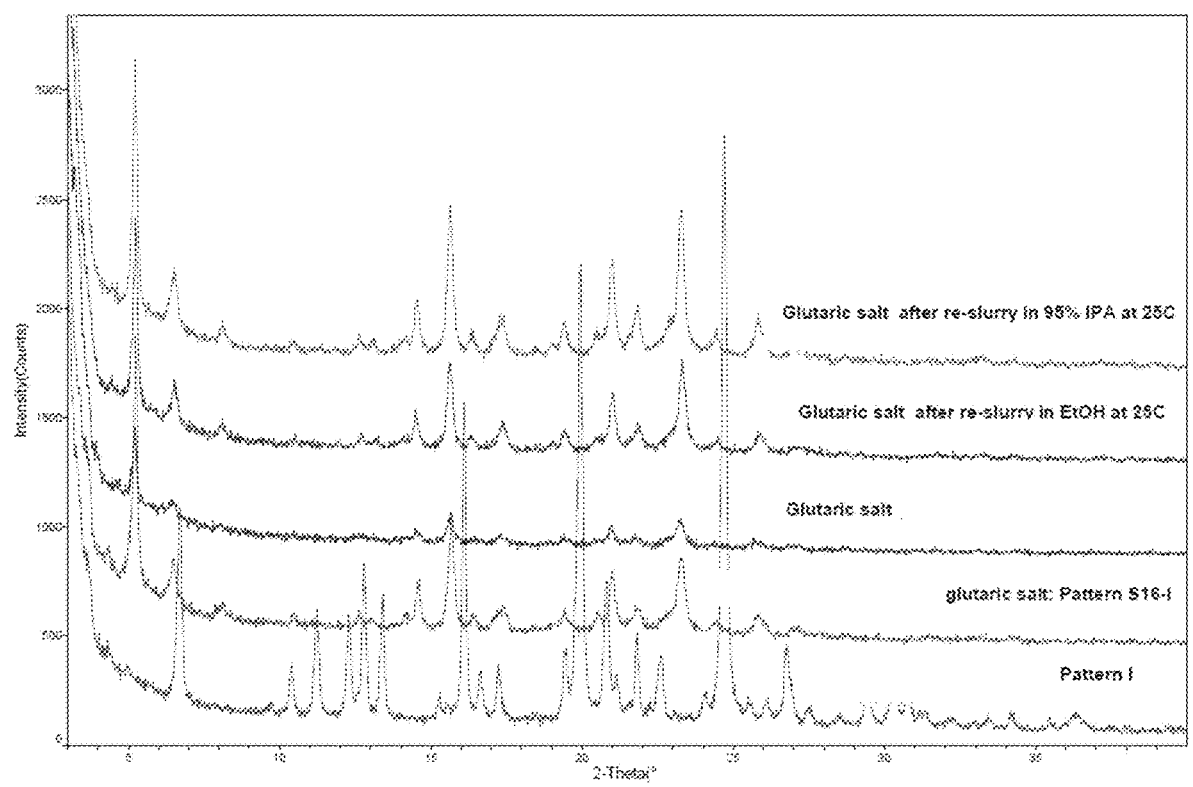
FIG. 17C depicts the characterization of X-ray diffraction pattern of Compound I-17 after re-slurry experiments compared to the X-ray diffraction pattern of Pattern A of Compound I-1.
Figure 17D:
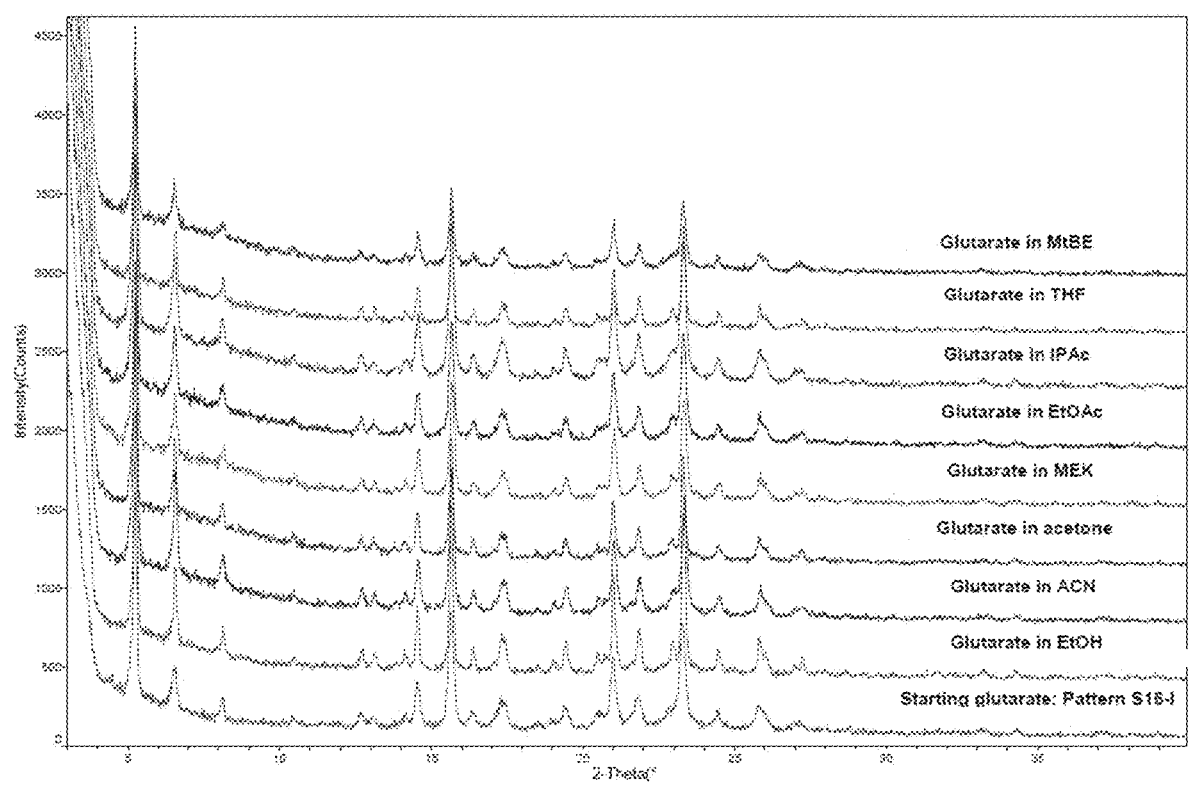
FIG. 17D depicts the characterization of X-ray diffraction pattern of Compound I-17 after polymorph screen experiments.

As shown in XRPD results of obtained solids in FIG. 7C for compound I-7 and FIG. 17C for compound I-17, the crystallinity of the product was enhanced after re-slurry experiments.

Example 5—Polymorph Investigation of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine hydroglutarate (Compound I-17) and (R)-1'-(3-(3,4-dihydro-1,5-naphthyridin-1(2H)-yl)-1H-pyrazolo[3,4-b]pyrazin-6-Yl)-3H-spiro[benzofuran-2,4'-piperidin]-3-amine hydromalonate (Compound I-12)

Polymorph investigation of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine glutarate and malonate salts was performed in 12 different solvents by temperature cycling method. If a suspension was not observed when the system was cooled to 25° C., then the solution was evaporated. Details of operation procedures were listed as below:

About 50 mg of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine glutarate or malonate were weighted into 2.0-mL glass vials and then 0.5 mL selected solvents were added. The samples were stirred at a speed of 700 r/min and then heated or cooled according to below temperature programs: heating to 50° C. in 1 hr and then holding at 50° C. for 1 hr; then cooling to 5° C. in 3 hrs and then holding at 5° C. for 1 hr. This temperature program was re-cycled for 8 times for a total of about 48 hrs. For samples which resulted in suspensions, the systems were centrifuged at 8000 r/min for 5 mins. Mother liquids were removed, and wet solids were dried in the vacuum oven at 30° C. for 17 hrs. Obtained dry solids were then characterized by XRPD. For the clear solutions, the vials were then placed in the fume hood at 25° C. to evaporate residual solvents.

Initial glutarate of (R)-1'-(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine was in crystalline form and this form was named as Pattern S16-I. After polymorph screening experiments, obtained solids all showed the same XRPD pattern as initial glutarate salt.

TABLE 5

| | | Appearance | | |
|---|---|---|---|---|
| # | Solvents | Temperature cycling | Evaporation | XRPD Results |
| 1 | MeOH | Clear Solution | Yes | S16-I |
| 2 | EtOH | Suspension | N/A | S16-I |
| 3 | ACN | Suspension | N/A | S16-I |
| 4 | Acetone | Suspension | N/A | S16-I |
| 5 | MEK | Suspension | N/A | S16-I |
| 6 | EtOAc | Suspension | N/A | S16-I |
| 7 | IPAc | Suspension | N/A | S16-I |
| 8 | THF | Suspension | N/A | S16-I |
| 9 | MtBE | Suspension | N/A | S16-I |
| 10 | Toluene | Suspension | N/A | S16-I |
| 11 | 1,4 dioxane | Clear Solution | Yes | S16-I |
| 12 | EtOH/water (9v/1v) | Clear Solution | Yes | S16-I |

Initial malonate of (R)-1'(3-(3,4-dihydro-1,5-naphthyridin-1(2H)-yl)-1H-pyrazolo[3,4-b]pyrazin-6-yl)-3H-spiro[benzofuran-2,4'-piperidin]-3-amine was also in crystalline form and this form was named as Pattern S11-I. After polymorph screening experiments, obtained solids all showed the same XRPD pattern as initial malonate salt.

TABLE 6

| # | Solvents | Appearance Temperature cycling | Evaporation | XRPD Results |
|---|---|---|---|---|
| 1 | MeOH | Suspension | N/A | S11-I |
| 2 | EtOH | Suspension | N/A | S11-I* |
| 3 | ACN | Suspension | N/A | S11-I |
| 4 | Acetone | Suspension | N/A | S11-I |
| 5 | MEK | Suspension | N/A | S11-I |
| 6 | EtOAc | Suspension | N/A | S11-I |
| 7 | IPAc | Suspension | N/A | S11-I |
| 8 | THF | Suspension | N/A | S11-I |
| 9 | MtBE | Suspension | N/A | S11-I |
| 10 | Toluene | Suspension | N/A | S11-I |
| 11 | 1,4 dioxane | Suspension | N/A | S11-I |
| 12 | EtOH/water (9v/1v) | Suspension | N/A | S11-I |

*The pattern from EtOH system showed some difference with initial form.

Note:
A small amount of malonate solids were observed when MeOH was used as a solvent.

For the malonate system, it was observed that the XRPD pattern from ethanol system showed some difference with that of initial malonate (Pattern S11-I). This pattern was named as Pattern S11-I* temporarily. Pattern S11-I* was further characterized by PLM, DSC, TGA and 1H-NMR.

Figure 12E:
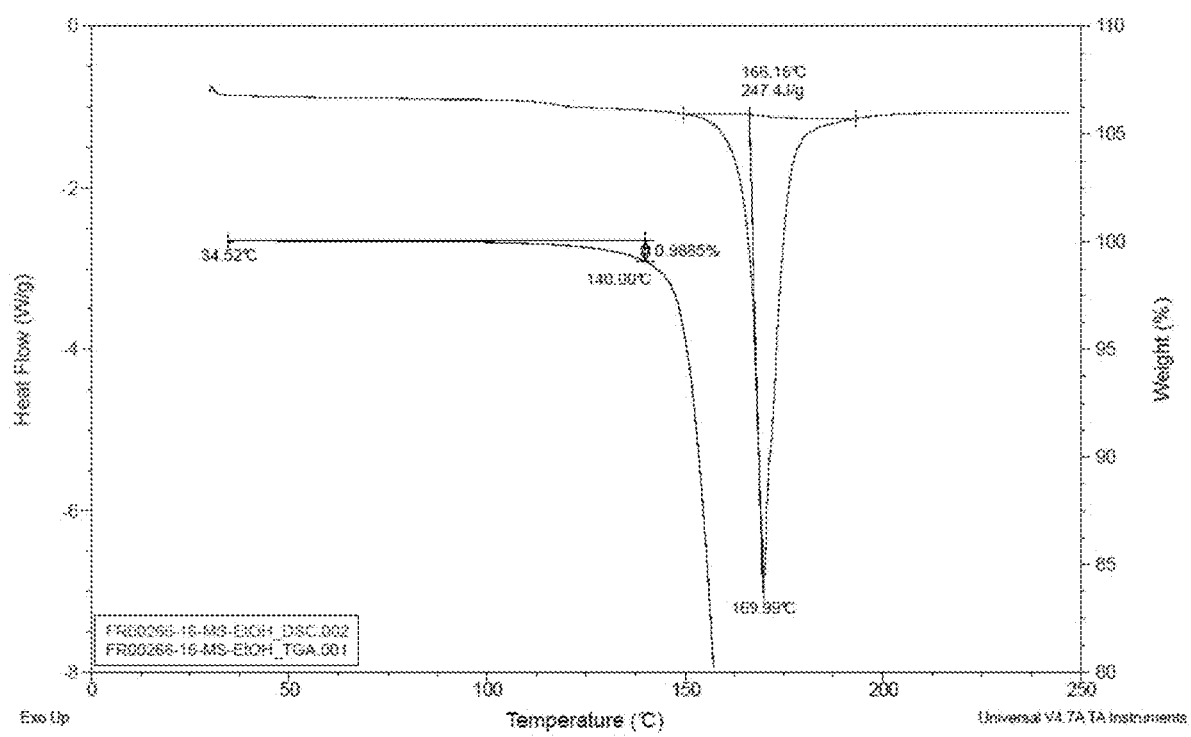
FIG. 12E depicts the characterization of Pattern S11-I* of Compound I-12 by 12 by differential scanning calorimetry (DSC) (green) and thermogravimetric analysis (TGA) (blue).

The DSC scan of Pattern S11-I* in FIG. 12E showed a large endothermic peak with the onset 166.16° C. (247.4 J/g). While the TGA scan showed a 0.99% weight loss from 35° C. to 140° C. Meanwhile, according to 1H-NMR results of Pattern S11-I*, few residual ethanol (0.45%) was observed in the final product. It was indicated that Pattern S11-I* should be a polymorph of malonate, not a solvate. The difference between S11-I and S11-I* may be resulted from the preferred orientation effect.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed:
1. A solid form of Compound I-1:

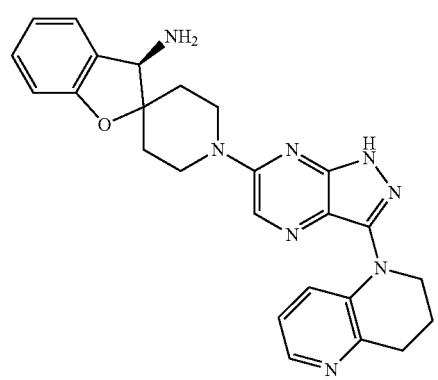

or a pharmaceutically acceptable salt thereof,
characterized by an X-ray powder diffraction (XRPD) pattern having at least two peaks, in degrees 2θ, each peak selected from the group consisting of about 24.6, about 19.9, about 16.0, about 6.7, about 12.8, about 13.4, and about 20.7.

2. The solid form of claim 1, wherein the solid form is crystalline.

3. The solid form of claim 2, wherein the solid form is characterized by an XRPD pattern having peaks, in degrees 2θ, at about 24.6, about 19.9, about 16.0, about 6.7, about 12.8, about 13.4, and about 20.7.

4. The solid form of claim 2, characterized by a differential scanning calorimetry (DSC) profile showing an endotherm with an onset of about 196° C., and a peak of about 197° C.

5. A compound of Formula (I)

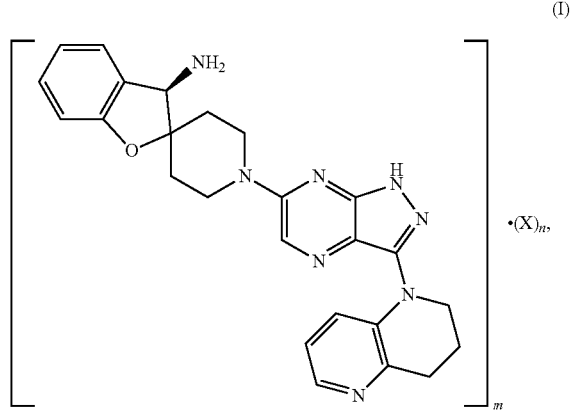

wherein,
m is 1-9;
n is 1-3; and
X is selected from the group consisting of hydrochloric acid, hydrobromic acid, sulfuric acid, methane sulfonic acid, phosphoric acid, p-toluene sulfonic acid, benzene sulfonic acid, oxalic acid, L-aspartic acid, maleic acid, malonic acid, L-tartaric acid, fumaric acid, citric acid, succinic acid, and glutaric acid, wherein the compound is in solid form.

6. The compound of claim 5, wherein the compound is amorphous.

7. The compound of claim 5, wherein the compound is crystalline.

8. The compound of claim 7, wherein the compound is characterized by an XRPD pattern substantially similar to that depicted in FIG. 2A or FIG. 2B.

9. The compound of claim 7, wherein the compound is characterized by an XRPD pattern substantially similar to that depicted in FIG. 4B.

10. The compound of claim 7, wherein the compound is characterized by an XRPD pattern substantially similar to that depicted in FIG. 8A.

11. The compound of claim 7, wherein the compound is characterized by an XRPD pattern substantially similar to that depicted in FIG. 12B.

12. The compound of claim 7, wherein the compound is characterized by an XRPD pattern substantially similar to that depicted in FIG. 17A, FIG. 17C, or FIG. 17D.

13. A pharmaceutical composition comprising a solid form of claim 1, or a pharmaceutically acceptable salt thereof, and a pharmaceutically acceptable carrier.

14. A method of inhibiting SHP2 phosphatase activity in a subject in need thereof, comprising administering a therapeutically effective amount of a solid form of claim 1, or a pharmaceutically acceptable salt thereof, to the subject.

15. The method of claim 14, wherein the subject is a human.

16. A method of treating a disorder mediated by SHP2 in a subject in need thereof, comprising administering a therapeutically effective amount of a solid form of claim 1, or a pharmaceutically acceptable salt thereof, to the subject.

17. The method of claim 16, further comprising administration of a therapeutically effective amount of an antibody, an antibody-drug conjugate, an immunomodulator, or a histone deacetylase inhibitor.

18. The method of claim 16, wherein the disorder is Noonan syndrome, neutropenia, diabetes, or neuroblastoma.

19. The method of claim 16, wherein the disorder is melanoma, acute myeloid leukemia, juvenile leukemia, or juvenile myelomonocytic leukemia.

20. The method of claim 16, wherein the disorder is breast cancer, lung cancer, or colorectal cancer.

21. A kit comprising the solid form of claim 1, or a pharmaceutically acceptable salt thereof, and written instructions describing how to administer a pharmaceutical composition prepared using the solid form to a patient.

22. A process for preparing the crystalline form of claim 2, comprising: a) preparing a solution of compound I-1 in a solvent comprising at least one of EtOH, ACN, MEK, EtOAc, IPAc, THF, MtBE, Toluene, 1,4 dioxane, and water; b) heating the solution to completely dissolve the compound I-1; c) adjusting the temperature so that solid precipitates out of the solution; and d) isolating the crystalline form of compound I-1.

23. The process of claim 22, wherein heating the solution comprises heating the solution to about 50° C.

24. The process of claim 22, wherein adjusting the temperature comprises cooling the solution to about 5° C.

25. A process for preparing a compound of Formula I-1, the process comprising the step of neutralizing a compound of Formula I-3 with NaOH, thereby forming the compound of Formula I-1:

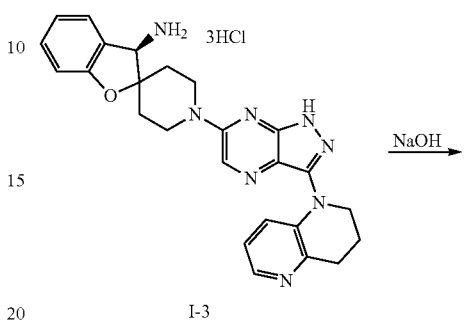

I-3

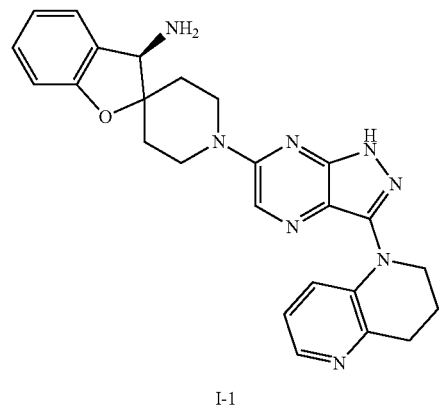

I-1

26. The process of claim 25, further comprising the step of reacting a compound of Formula 18 with HCl, thereby forming the compound of Formula 1-3:

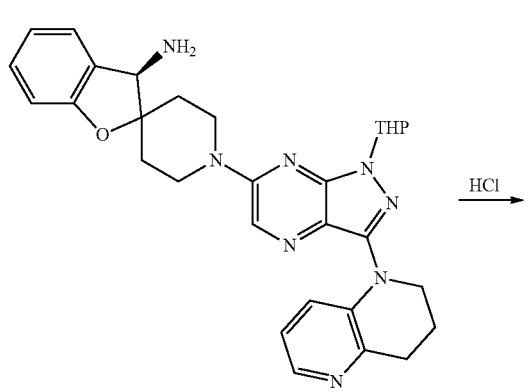

18

47
-continued
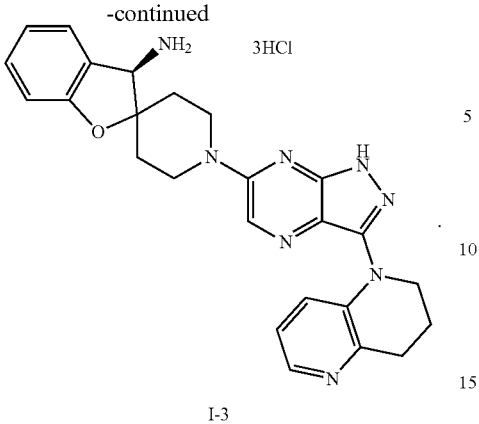
I-3
27. The process of claim 26, further comprising the step of coupling a compound of Formula 17 with a compound of Formula 9, thereby forming the compound of Formula 18:
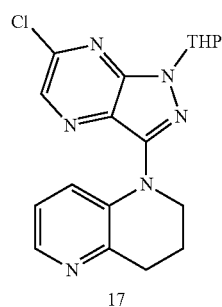
17
+
48
-continued
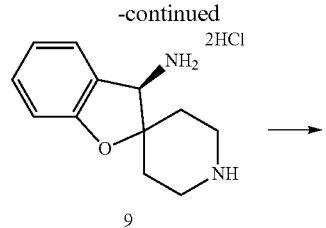
9
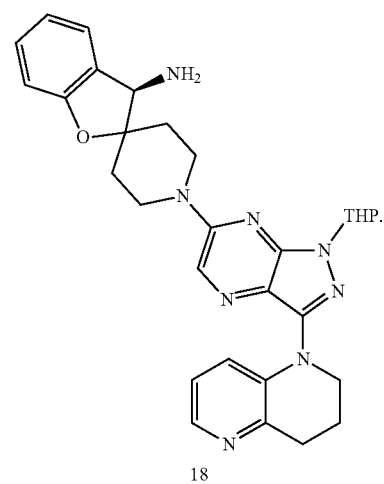
18
* * * * *